(12) United States Patent
Applewhite et al.

(10) Patent No.: US 9,066,917 B2
(45) Date of Patent: Jun. 30, 2015

(54) MIXED METAL COMPOUND

(71) Applicant: CYTOCHROMA DEVELOPMENT, INC., St. Michael (BB)

(72) Inventors: Richard Jonathan Applewhite, Cheshire (GB); James David Morrison, Norwich (GB); Maurice Sydney Newton, Sandbacj (GB); Nigel Peter Rhodes, Warrington (GB); Christopher John Rickard, Sandiway Northwich (GB)

(73) Assignee: CYTOCHROMA DEVELOPMENT INC., St. Michael (BB)

( * ) Notice: Subject to any disclaimer, the term of this patent is extended or adjusted under 35 U.S.C. 154(b) by 0 days.

(21) Appl. No.: 14/224,040

(22) Filed: Mar. 24, 2014

(65) Prior Publication Data

US 2014/0205667 A1    Jul. 24, 2014

Related U.S. Application Data

(62) Division of application No. 13/388,476, filed as application No. PCT/GB2010/051271 on Aug. 2, 2010.

(30) Foreign Application Priority Data

Aug. 3, 2009  (GB) ..................................... 913525.2

(51) Int. Cl.
*A61K 9/00*   (2006.01)
*A61K 33/26*  (2006.01)
(Continued)

(52) U.S. Cl.
CPC . *A61K 33/26* (2013.01); *A61K 6/04* (2013.01); *A61K 9/143* (2013.01); *A61K 9/1611* (2013.01);
(Continued)

(58) Field of Classification Search
CPC ....................................................... A61K 6/04
See application file for complete search history.

(56) References Cited

U.S. PATENT DOCUMENTS 2,222,924 A   11/1940  Weiss
2,812,344 A   11/1957  Oroshnik
(Continued)

FOREIGN PATENT DOCUMENTS

CA   1198674 A1   12/1985
DE   2061136 A1   7/1971
(Continued)

OTHER PUBLICATIONS

Abramowitz et al., Serum alkaline phosphatase and phosphate and risk of mortality and hospitalization, Clin. J. Am. Soc. Nephrol., 1:1064-71 (2010).
(Continued)

*Primary Examiner* — Paul Dickinson
(74) *Attorney, Agent, or Firm* — Marshall, Gerstein & Borun LLP

(57) ABSTRACT

There is provided a method of producing a mixed metal compound comprising at least $Mg^{2+}$ and at least $Fe^{3+}$ having an aluminum content of less than 10000 ppm, having an average crystal size of less than 20 nm (200 A) comprising the steps of: (a) combining a $Mg^{2+}$ salt and a $Fe^{3+}$ salt with $Na_2CO_3$ and NaOH to produce a slurry, wherein the pH of the slurry is maintained at from 9 5 to 1 1, and wherein the $Na_2CO_3$ is provided at an excess of 0 to 4.0 moles than is required to complete the reaction (b) subjecting the slurry to mixing under conditions providing a power per unit volume of 0 03 to 1.6 $kW/m^3$ (c) separating the mixed metal compound from the slurry, to obtain a crude product having a dry solid content of at least 10 wt % (d) drying the crude product either by (i) heating the crude product to a temperature of no greater than 150° C. and sufficient to provide a water evaporation rate of 0.05 to 1 5 kg water per hour per kg of dry product, or (H) exposing the crude product to rapid drying at a water evaporation rate of 500 to 50000 kg water per hour per kg of dry product.

37 Claims, 1 Drawing Sheet

Graphical representation of data from Table 3 demonstrating preferred range between 2-5 wt% interlayer sulphate wherein phosphate binding is high and wash time low

(51) Int. Cl.
- *A61K 6/04* (2006.01)
- *A61K 9/14* (2006.01)
- *A61K 9/16* (2006.01)
- *A61K 33/06* (2006.01)
- *A61K 33/10* (2006.01)
- *A61K 45/06* (2006.01)
- *B82Y 30/00* (2011.01)
- *C01G 49/00* (2006.01)

(52) U.S. Cl.
CPC ............. *A61K 9/1682* (2013.01); *A61K 33/06* (2013.01); *A61K 33/10* (2013.01); *A61K 45/06* (2013.01); *B82Y 30/00* (2013.01); *C01G 49/009* (2013.01); *C01P 2002/22* (2013.01); *C01P 2002/72* (2013.01); *C01P 2004/61* (2013.01); *C01P 2004/64* (2013.01); *C01P 2006/11* (2013.01); *C01P 2006/12* (2013.01); *C01P 2006/14* (2013.01); *C01P 2006/80* (2013.01); *C01P 2006/82* (2013.01)

(56) References Cited

U.S. PATENT DOCUMENTS

| | | |
|---|---|---|
| 3,101,270 A | 8/1963 | Evans et al. |
| 3,395,211 A | 7/1968 | Wielich |
| 3,650,704 A | 3/1972 | Kumura et al. |
| 3,743,098 A | 7/1973 | Martinez |
| 3,796,792 A | 3/1974 | Miyata et al. |
| 3,879,523 A | 4/1975 | Miyata et al. |
| 3,984,392 A | 10/1976 | van der Veen et al. |
| 4,192,900 A | 3/1980 | Cheng |
| 4,254,099 A | 3/1981 | Asmussen et al. |
| 4,351,814 A | 9/1982 | Miyata et al. |
| 4,370,280 A | 1/1983 | Oediger et al. |
| 4,415,555 A | 11/1983 | Anabuki et al. |
| 4,458,026 A | 7/1984 | Reichle |
| 4,514,389 A | 4/1985 | Miyata |
| 4,566,986 A | 1/1986 | Waldmann |
| 4,582,705 A | 4/1986 | Primes et al. |
| 4,609,543 A | 9/1986 | Morris et al. |
| 4,629,626 A | 12/1986 | Miyata et al. |
| 4,661,330 A | 4/1987 | Chane-Ching et al. |
| 4,689,219 A | 8/1987 | Sugden |
| 4,735,629 A | 4/1988 | Glemser et al. |
| 4,786,510 A | 11/1988 | Nakel et al. |
| 4,801,454 A | 1/1989 | Coveney |
| 4,970,079 A | 11/1990 | Hem et al. |
| 4,994,283 A | 2/1991 | Mehansho et al. |
| 5,002,747 A | 3/1991 | Le Loarer |
| 5,085,869 A | 2/1992 | Olthoff et al. |
| 5,112,604 A | 5/1992 | Beaurline et al. |
| 5,153,156 A | 10/1992 | Schutz et al. |
| 5,173,284 A | 12/1992 | Moisset et al. |
| 5,185,093 A | 2/1993 | Ichikawa et al. |
| 5,213,794 A | 5/1993 | Fritsch et al. |
| 5,246,899 A | 9/1993 | Bhattacharyya |
| 5,273,767 A | 12/1993 | Burgum |
| 5,300,302 A | 4/1994 | Tachon et al. |
| 5,506,248 A | 4/1996 | Nikfar et al. |
| 5,514,281 A | 5/1996 | Boos et al. |
| 5,525,305 A | 6/1996 | Minekus et al. |
| 5,571,336 A | 11/1996 | Wurzburger et al. |
| 5,651,997 A | 7/1997 | Makino et al. |
| 5,654,011 A | 8/1997 | Jackson et al. |
| 5,656,080 A | 8/1997 | Staniforth et al. |
| 5,817,340 A | 10/1998 | Roche et al. |
| 5,846,426 A | 12/1998 | Boos et al. |
| 5,968,976 A | 10/1999 | Murrer et al. |
| 6,028,023 A | 2/2000 | Vierheilig |
| 6,039,981 A | 3/2000 | Woo et al. |
| 6,103,126 A | 8/2000 | Boos et al. |
| 6,174,442 B1 | 1/2001 | Geisser et al. |
| 6,287,596 B1 | 9/2001 | Murakami et al. |
| 6,448,323 B1 | 9/2002 | Jordan et al. |
| 6,576,255 B1 | 6/2003 | Petereit et al. |
| 6,576,665 B2 | 6/2003 | Dennett, Jr. et al. |
| 6,596,311 B1 | 7/2003 | Dobetti |
| 6,696,087 B2 | 2/2004 | Matsuda et al. |
| 6,720,005 B1 | 4/2004 | Ayres |
| 6,733,780 B1 | 5/2004 | Tyler et al. |
| 6,749,864 B2 | 6/2004 | Makino et al. |
| 6,790,895 B2 | 9/2004 | Stelandre et al. |
| 6,794,367 B1 | 9/2004 | Tanida et al. |
| 6,926,912 B1 | 8/2005 | Roberts et al. |
| 7,259,192 B2 | 8/2007 | Liu et al. |
| 7,300,670 B2 | 11/2007 | Venus et al. |
| 7,799,351 B2 | 9/2010 | Roberts et al. |
| 1,001,430 A1 | 1/2011 | Roberts et al. |
| 2002/0122786 A1 | 9/2002 | Matsuda et al. |
| 2003/0150249 A1 | 8/2003 | Gillman et al. |
| 2003/0185886 A1 | 10/2003 | Lee et al. |
| 2004/0022872 A1 | 2/2004 | Sofue et al. |
| 2004/0105896 A1 | 6/2004 | Roberts et al. |
| 2004/0247696 A1 | 12/2004 | Antelman |
| 2005/0260271 A1 | 11/2005 | Bringley |
| 2005/0266071 A1 | 12/2005 | Olmstead et al. |
| 2006/0177415 A1 | 8/2006 | Burke |
| 2008/0187602 A1 | 8/2008 | Ferdinando et al. |
| 2009/0175959 A1 | 7/2009 | Bando et al. |
| 2009/0317459 A1 | 12/2009 | Pennel et al. |
| 2010/0215770 A1 | 8/2010 | Newton et al. |
| 2012/0093943 A1 | 4/2012 | Newton et al. |
| 2012/0201864 A1 | 8/2012 | Applewhite et al. |
| 2013/0323325 A1 | 12/2013 | Applewhite et al. |

FOREIGN PATENT DOCUMENTS

| | | |
|---|---|---|
| DE | 3346943 A1 | 7/1985 |
| DE | 3402878 A1 | 8/1985 |
| DE | 3801382 A1 | 8/1989 |
| EP | 0050792 A1 | 5/1982 |
| EP | 0134936 A1 | 3/1985 |
| EP | 0146410 A2 | 6/1985 |
| EP | 0150792 A2 | 8/1985 |
| EP | 0368420 A2 | 5/1990 |
| EP | 0577294 A2 | 1/1994 |
| EP | 0638313 A1 | 2/1995 |
| EP | 1304104 A2 | 4/2003 |
| EP | 1413197 A2 | 4/2004 |
| EP | 1707178 A1 | 10/2006 |
| EP | 1932808 A1 | 6/2008 |
| EP | 1946750 A1 | 7/2008 |
| ES | 2018952 A6 | 5/1991 |
| FR | 1214473 A | 4/1960 |
| FR | 2254556 A1 | 7/1975 |
| GB | 1336866 A | 11/1973 |
| GB | 1378830 A | 12/1974 |
| GB | 2031395 A | 4/1980 |
| GB | 2254556 A | 10/1992 |
| HU | 173556 B | 6/1979 |
| HU | 201880 B | 1/1991 |
| IE | 63343 B1 | 4/1995 |
| IN | 192168 A1 | 3/2004 |
| JP | 61036222 A | 2/1986 |
| JP | 62145024 A | 6/1987 |
| JP | 05155776 A | 6/1993 |
| JP | 05208816 A | 8/1993 |
| JP | 10059842 A | 3/1998 |
| JP | 10101569 A | 4/1998 |
| JP | 10236960 A | 9/1998 |
| JP | 3001114 B2 | 1/2000 |
| JP | 2000086537 A | 3/2000 |
| JP | 2001517633 A | 10/2001 |
| JP | 2004089760 A | 3/2004 |
| PL | 189716 B1 | 6/1997 |
| PL | 200957 B1 | 11/1999 |
| SU | 414849 A1 | 9/1977 |
| WO | WO-91/18835 A1 | 12/1991 |
| WO | WO-92/01458 A1 | 2/1992 |
| WO | WO-93/22237 A1 | 11/1993 |
| WO | WO-94/09798 A1 | 5/1994 |
| WO | WO-95/11033 A1 | 4/1995 |
| WO | WO-95/29679 A1 | 11/1995 |

(56) References Cited

FOREIGN PATENT DOCUMENTS

| WO | WO-96/30029 A1 | 10/1996 |
|---|---|---|
| WO | WO-97/11166 A1 | 3/1997 |
| WO | WO-97/22266 A1 | 6/1997 |
| WO | WO-97/48380 A1 | 12/1997 |
| WO | WO-99/15189 A1 | 4/1999 |
| WO | WO-99/44580 A1 | 9/1999 |
| WO | WO-0032189 A1 | 6/2000 |
| WO | WO-01/27069 A1 | 4/2001 |
| WO | WO-0149301 A1 | 7/2001 |
| WO | WO-03/013473 A1 | 2/2003 |
| WO | WO-03017980 A1 | 3/2003 |
| WO | WO-03028706 A1 | 4/2003 |
| WO | WO-03072084 A1 | 9/2003 |
| WO | WO-03092658 A1 | 11/2003 |
| WO | WO-2004/016553 A2 | 2/2004 |
| WO | WO-2004018094 A1 | 3/2004 |
| WO | WO-2005/009381 A2 | 2/2005 |
| WO | WO-2005/012194 A1 | 2/2005 |
| WO | WO-2005/018651 A1 | 3/2005 |
| WO | WO-2005/027876 A1 | 3/2005 |
| WO | WO-2006/085079 A2 | 8/2006 |
| WO | WO-2007/074909 A1 | 7/2007 |
| WO | WO-2007/088343 A2 | 8/2007 |
| WO | WO-2007/135362 A2 | 11/2007 |
| WO | WO-2008/071747 A1 | 6/2008 |
| WO | WO-2008/129034 A1 | 10/2008 |
| WO | WO-2009/016349 A1 | 2/2009 |
| WO | WO-2009/050468 A1 | 4/2009 |

OTHER PUBLICATIONS

Adachi-Pagano et al., Synthesis of Al-rich hydrotalcite-like compounds by using the urea hydrolysis reaction-control of size and morphology, J. Mater. Chem., 13(8):1988-93 (2003).
Adams et al., Formulation of a sterile surgical lubricant, J. Pharm. Pharmacol., 24 Suppl:178P (1972).
Albaaj et al., Hyperphosphataemia in renal failure: causes, consequences and current management, Drugs, 63(6):577-96 (2003).
Ambrogi et al., Intercalation compounds of hydrotalcite-like anionic clays with anti-inflammatory agents, II: Uptake of diclofenac for a controlled release formulation, AAPS PharmSciTech., 3(3):E26 (2002).
Ansel et al., Pharmaceutical Dosage Forms and Drug Delivery Systems, Chapter 1-8 (pp. 1-243) Lippincott, Williams & Wilkins (1999).
Aoshima et al., Glycerin fatty acids esters as a new lubricant of tablets, Int. J. Pharm., 293:25-34 (2005).
Autissier et al., Relative in vitro efficacy of the phosphate binders lanthanum carbonate and sevelamer hydrochloride, J. Pharm. Sci., 96(10):2816-27 (2007).
Badawy et al., Effect of drug substance particle size on the characteristics of granulation manufactured in a high-shear mixer, AAPS PharmSciTech., 1(4):E33 (2000).
Badreddine et al.,Ion exchange of different phosphate ions into the zinc-aluminium-chloride layered double hydroxide, Materials Lett., 38(6): 391-5 (1999).
Barriga et al., Hydrotalcites as sorbent for 2,4,6-trinitrophenol: influence of the layer composition and interlayer anion, J. Mater. Chem., 12:1027-34 (2002).
Bejoy, Hydrotalcite: The Clay that Cures, Springer; Resonance, vol. 6 No. 2, pp. 57-61 (2001).
Bolhuis et al., Interaction of tablet disintegrants and magnesium strearate during mixing I: effect on tablet disintegration, J. Pharm. Sci., 70(12):1328-30 (1981).
Bolognini et al., Mg/Al mixed oxides prepared by coprecipitation and sol-gel routes: a comparison of their physico-chemical features and performances in m-cresol methylation, Microporous and Mesoporous Materials, 66:77-89 (2003).
Bothwell, Overview and mechanisms of iron regulation, Nutrition Rev., 53:237-45 (Sep. 1995).

Brauner, Das atomgewicht des lanthans, Zeitschrift fur Anorganische Chemie, 33(1):317-21 (1902).
Brouwers et al., Biopharmaceutical tests on antacids: in vitro and in vivo studies, Drugs Under Experiment. Clin. Res., 5:55-61 (1997).
Brouwers et al., De invioed van de toedieningsvorm op de weringsduur en op het pH-Bereik bij antacida: een in-vitro en in-vivo studie,Pharmaceutisch Weekblad, 111:1244-8 (1976) (abstract only).
Brouwers, Liquid Antacids, Pharmaceutisch Weekblad, 110:337-51 (1975) (abstract only).
Budavari et al. (eds.), The Merck Index, pp. 277, 331, and 917, Merck & Co. (1996).
Carlino, Chemistry between the sheets, Chemistry in Britain, pp. 59-62 (Sep. 1997).
Chatelet et al., Competition between monovalent and divalent anions for calcined and uncalcined hydrotalcite: anion exchange and adsorption sites, Colloids and Surfaces A: Physiochemical and Engineering Aspects, 111:167-75 (1996).
Chitrakar et al., Adsorption of phosphate from seawater on calcined MgMn-layered double hydroxides, J. Colloid Interface Sci., 290(1): 45-51 (2005).
Cook, Adaptation in iron metabolism, Am. J. Clin. Nutr., 51(2):301-8 (1990).
Das et al., Adsorption of phosphate by layered double hydroxides in aqueous solutions, Appl. Clay Sci., 32(3-4):252-60 (2006).
de Roy et al., Antionic Clays: Trends in Pillaring Chemistry, chapter 7, pp. 108-169 IN: Synthesis of Microporous Mateirals (1992).
de Roy et al., Layered double hydroxides: synthesis and post-synthesis modification, Chapter I, pp. 33-34 IN: Rives (ed.), Layered Double Hydroxides: Present and Future, Nova Science Publishers, Inc. (2001).
de Roy et al., Surface Text and Electron Microscopy Studies, pp. 243-244 IN: Rives (ed.), Layered Double Hydroxides: Present and Future, Nova Science Publishers, Inc. (2001).
del Arco et al., Effect of the Mg:Al ratio on borate (or silicate)/nitrate exchange in hydrotalcite, J. Solid State Chem., 151(2):272-80 (2000).
del Arco et al., Surface and textural properties of hydrotalcite-like materials and their decomposition products, IN: Rouquerol et al. (eds.), Characterization of Porous Solids III, Studies in Surface Science and Catalysis, vol. 87, pp. 507-515 (1994).
Dewberry et al., "Lanthanum carbonate: A novel non-calcium containing phosphate binder", J Am Soc Nephrol, 8:A2610 (1997).
Drueke, Lanthanum carbonate as a first-line phosphate binder: the "cons", Semin. Dial., 20(4):329-32 (2007).
Emmett, A comparison of clinically useful phosphorus binders for patients with chronic kidney failure, Kidney Int.,66:S25-S32 (2004).
Entry for "obtainable", Collins English Dictionary, retrieved from the Internet at <http://www.collinsdictionary.com> on May 15, 2013.
Erickson et al., A study of structural memory effects in synthetic hydrotalcites using environmental SEM, Materials Lett., 59:226-9 (2005).
Evans et al., "Structural Aspects of Layered Double Hydroxides" pp. 1-12, IN: Duan et al. (eds.), Layered Double Hydroxides, vol. 119, Springer (2006).
Evonik Industries AG, product information for Eudragit® E100, Eudragit® E POA and Eudragit® E 12,5; pp. 1-6 (Oct. 2011).
Fernandez et al., The effect of iron on the crystalline phases formed upon thermal decomposition of Mg-Al-Fe hydrotalcites, RCS Publishing: Journal of Materials Chemistry, 8(11):2507-14 (1998).
Ferreira et al., Thermal decomposition and structural reconstruction effect on Mg Fe based hydrocalcite compounds, J. Solid State Chem., 177:3058-69 (2004).
Forano, Environmental remediationinvolving layered double hydroxides, pp. 426-458, vol. 1, Elsevier Interface Science and Technology (2004).
Frost et al., Thermal decomposition of synthetic hydrotalcites reevesite and pyroaurite, J. Therm. Analysis Calorimetry, 76:217-25 (2004).
Goh et al., Application of layered double hydroxides for removal of oxyanions: a review, Water Res., 42:1343-68 (2008).
Grant et al. (eds.), Grant & Hackh's Chemical Dictionary, 5th edition, McGraw Hill, pp. 571 (1987).

(56) References Cited

OTHER PUBLICATIONS

Grubel et al., Interaction of an aluminum-magnesium containing antacid and gastric mucus: possible contribution to the cytoprotective function of antacids, Aliment. Pharmacol. Ther., 11(1):139-45 (1997).
Guillot et al., The use of magnesium-containing phosphate binders in patients with end-stage renal disease on maintenance hemodialysis, Nephron., 30(2):144-7 (1982).
Hansen et al., Formation of synthetic analogues of double metal-hydroxy carbonate minerals under controlled pH conditions: I. The synthesis of pyroaurite and reevesite, Clay Minerals, 25:161-79 (1990).
Hansen et al., Reduction of nitrate to ammonium by sulphate green rust: activation energy and reaction mechanism, Clay Minerals, 33:87-101 (1998).
Hansen et al., Synthesis and characterization of pyroaurite, Appl. Clay Sci., 10(1-2):5-19 (1995).
Hansen et al., The use of glycerol intercalates in the exchange of $CO_3^{2-}$ with $SO_4^{2-}$, $NO^{3-}$, or $C_L$-in pyroaurite-type compounds, Clay Minerals, 26:311-27 (1991).
Hashi et al., Preparation and properties of pyroaurite-like hydroxy minerals, Clays and Clay Minerals, 31(2):152-4 (1983).
He et al., Hydrothermal Methods, p. 108 IN: Duan et al. (eds.), Layered Double Hydroxides, Springer-Verlag Berlin Heidelberg (2006).
He et al., Preparation of Layered Double Hydroxides, Struct. Bond., 119:89-119 (2006).
Hibino et al., Calcination and rehydration behavior of Mg-Fe-CO3 hydrotalcite-like compounds, J. Materials Sci. Lett., 19(16):1403-5 (2000).
Hirahara et al., Synthesis and antacid property of Mg-Fe layered double hydroxide, Nendo Kagaku—J. Clay Sci. Soc. of Japan, 42(2):70-6 (2002).
Hollander et al., Antacids vs. placebos in peptic ulcer therapy: a controlled double-blind investigation, JAMA, 226(10):1181-5 (1973).
Hudson et al., Thermal conversion of a layered (Mg/Al) double hydroxide to the oxide, J. Mater. Chem., 5(2):323-9 (1995).
International Preliminary Report on Patentability for corresponding international application No. PCT/GB2010/051271, issuance date Feb. 7, 2012.
International Search Report and Written Opinion for corresponding international application No. PCT/GB2010/051271, mailing date Oct. 26, 2010.
International Specialty Products, Pharmaceuticals Solid Dosage Forms (2004).
Iranloye et al., Effects of compression force, particle size and lubricants on dissolution rate, J. Pharm. Sci., 67(4):535-9 (1978).
Ishimura et al., "Hyper- and Hypophosphataemia" pp. 149-158, IN: Morii et al. (eds.), Calcium in Internal Medicine, Springer (2002).
Kaplan et al., A preference study: calcium acetate tablets versus gelcaps in hemodialysis patients, Nephrol. Nurs. J., 29(4):363-5 (2002).
Kokot et al., A rotating disk study on the rates of hydrotalcite dissolution at 25°C, Pharmazie, 48 (H4):287-9 (1993).
Konorev et al., Selection of the optimal antacid drug in clinical practice, Consilium Medicum, vol. 5, issue 10 (2003).
Kostura et al., Rehydration of calcined Mg-Al hydrotalcite in acidified chloride-containing aqueous solution, Collect. Czech. Chem. Commun., 72:1284-94 (2007).
Kovanda et al., Thermal behavior of Ni-Mn layered double hydroxide and characterization of formed oxides, Solid State Sci., 5:1019-26 (2003).
Labajos et al., New layered double hydroxides with hydrotalcite structure containing Ni(II) and V(III), J. Materials Chem., 9:1033-9 (1999).
Larsson et al., Estimation of the bioavailability of iron and phosphorous in cereals using a dynamic in vitro gastrointestinal model, J. Sci. Food Agric., 74:99-106 (1997).
Lazaridis et al., Flotation of metal loaded clay anion exchangers, Part II: the case of arsenates, Chemosphere, 47:319-24 (2002).
Lazaridis et al., Flotation of metal loaded clay anion exchangers, Part II: the case of chromates, Chemosphere, 42:373-8 (2001).
Lazaridis, Sorption removal of anions and cations in single batch systems by uncalcined and calcined Mg-Al-CO3 hydrotalcite, Water Air Soil Pollution, 146:127-39 (2003).
Leinonen et al., Physical and lubrication properties of magnesium stearate, J. Pharm. Sci., 81(12):1194-8 (1992).
Li et al., Enteric-coated layered double hydroxides as a controlled release drug delivery system, Int. J. Pharm., 287(1-2):89-95 (2004).
Li et al., Stoichiometric Synthesis of Pure MFe2O4 (M = Mg, Co, and Ni) Spinel Ferrites from Tailored Layered Double Hydroxide (Hydrotalcite-Like) Precursors, Chem. Mater., 16(8):1597-602 (2004).
Lin et al., Evaluation of buffering capacity and acid neutralizing-pH time profile of antacids, J. Formos. Med. Assoc., 97:704-10 (1998).
Linares et al., The influence of hydrotalcite and cancrinite type zeolite in acidic aspirin solutions, Microporous and Mesoporous Materials, 74:105-10 (2004).
Llewellyn et al., The binding of bile acids by hydrocalcite and other antacid preparations, Pharmaceutica Acta Helvetiae, 52(1/2):1-5 (1977).
Logham-Adham, Safety of new phosphate binders for chronic renal failure, Drug Safety, 26(15):1093-1115 (2003).
MacCara, Acid neutralization capacity of Canadian antacid formulations, Can. Med. Assoc. J., 132:523-7 (1985).
Marchi et al., Impregnation-induced memory effect of thermally activated layered double hydroxide, Appl. Clay Sci., 13:35-48 (1998).
McCance et al., Absorption and excretion of iron, The Lancet, pp. 680-684 (Sep. 18, 1937).
McIntyre et al., Iron-magnesium hydroxycarbonate (Alpharen): a novel non calcium containing phosphate binder for the treatment of hyperphosphataemia in chronic haemodialysis patients, Nephrol. Dial. Transplant., 22 (suppl 6): vi171, FP452 Poster Session Abstract (Jun. 22, 2007).
Meng et al., Preparation and thermal decomposition of magnesium/iron (III) layered double hydroxide intercalated by hexacyanoferrate (III) ions, J. Mater. Sci., 39:4655-7 (2004).
Meng et al., Preparation of magnetic material containing MgFe2O4 spinel ferrite from a Mg-Fe(III) layered double hydroxide intercalated by hexacyanoferrate(III) ions, Mater.Chem. Phys., 86:1-4 (2004).
Merck Index, p. 969, entries 5694-707 (1996).
Merck Index, p. 969, entries 5694-707.
Merriam-Webster's Collegiate Dictionary—11th edition, entry for "prophylaxis" on p. 996 (2004).
Mesh to Micron Conversion chart, retrieved from the Internet at <http:///www.shomegold.org/news/Mesh.htm>, accessed Sep. 27, 2012.
Miederer et al., Acid neutralization and bile acid binding capacity of hydrocalcite compared with other antacids: an in-vitro study, Chinese J. Digestive Diseases, 4(3):140-6 (2003).
Miyata et al., Physiochemical properties of synthetic hydrotalcites in relation to composition, Clays and Clay Minerals, 28(1):50-6 (1980).
Murthy et al., Effect of shear mixing on in vitro drug release of capsule formulations containing lubricants, J. Pharm. Sci., 66(9):1215-9 (1977).
Naylor et al., Use of gastrointestinal model and gastroplus for the prediction of in vivo performance, Industrial Pharmacy, 12:9-12 (2006).
Newman et al., Comparative study of some layered hydroxide salts containing exchangable interlayer anions, J. Solid State Chem., 148:26-40 (1999).
O'Donovan et al., Substitution of aluminium salts by magnesium salts in control of dialysis hyperphosphataemia, The Lancet, pp. 880-881 (Apr. 19, 1986).
Oe et al., Long-term use of magnesium hydroxide as a phosphate binder in patients on hemodialysis, Clin. Nephrol., 28(4)180-5 (1987).
Ookubo et al., Hydrotalcites as potential adsorbents of intestinal phosphate, J. Pharm. Sci., 81(11):1139-40 (1992).

(56) References Cited

OTHER PUBLICATIONS

Ookubo et al., Preparation and phosphate ion-exchange properties of a hydrotalcite-like compound, Langmuir, 9(5):1418-22 (1993).
Pesic et al., Thermal characteristics of a synthetic hydrotalcite like material, J. Mater. Chem., 2(10):1069-72 (1992).
Playle et al., The in-vitro antacid and anti-pepsin activity of hydrotalcite, Pharm. Acta Helv., 49(9/10):298-302 (1974).
Powell et al., The chemistry between aluminum in the gastrointestinal lumen and its uptake and absorption, Proc. Nutrition Soc., 52:241-53 (1993).
Rajamathi et al., Reversable thermal behaviour of the layered double hydroxide of Mg with Al: mechanistic studies, J. Mater. Chem., 10:2754-7 (2000).
Raki et al., Preparation, Characterization, and Moessbauer Spectroscopy of Organic Anion Intercalated Pyroaurite-like Layered Double Hydroxides, Chem. Mater., 7(1):221-4 (1995).
Rankin et al., The development and in-vitro evaluation of novel mixed metal hydroxy-carbonate compounds as phosphate binders, J. Pharm. Pharmacol., 53:361-9 (2001).
Reichle, Synthesis of anionic clay minerals (mixed metal hydroxides, hydrotalcite), Solid State Ionics, 22(1):135-41 (1986).
Remuzzi et al., Hematologic consequences of renal failure, The Kidney, vol. II, 5th ed. pp. 2170-2186 (1996).
Rives, Study of Layered Double Hydroxides by Thermal Methods, chapter 4, pp. 116-133 IN: Rives (ed.), Layered Double Hydroxides: Present and Future, Nova Science Pub Inc. (2001).
Robolot et al., Effect of lubricant level and applied copressional pressure on surface friction of tablets, J. Pharm. Sci., 74(6):697-9 (1985).
Rodriguez-Benot et al., Mild hyperphosphatemia and mortality in hemodialysis patients, Am. J. Kidney Dis., 46(1):68-77 (2005).
Rubinstein et al., The effect of granule size on the in vitro and in vivo properties of bendrofluazide tablets 5mg, Pharm. Acta Helv., 52 (1/2): 5-10 (1977).
Rudnic et al., Oral Solid Dosage Forms, chapter 45, pp. 858-890 IN: Gennaro (ed.), Remington: The Science and Practice of Pharmacy, 20th ed., Lippincott Williams & Wilkins (2000).
Sato et al., Adsorption of various anions by magnesium aluminum oxide Mg(0.7)Al(0.3)O(1.15), Ind. Eng. Chem. Prod. Res. Dev., 25:89-92 (1986).
Sato et al., Causticization of sodium carbonate with rock-salt-type magnesium aluminium oxide formed by the thermal decomposition of hydrotalcite-like layered double hydroxide, J. Chem. Tech. Biotechnol., 57:137-40 (1993).
Schwarz et al., Association of disorders in mineral metabolism with progression of chronic kidney disease, Clin. J. Am. Soc. Nephrol., 1:825-31 (2006).
Seida et al., Removal of phosphate by layered double hydroxides containing iron, Water Res., 36:1305-12 (2002).
Sheikh et al., Reduction of dietary phosphorus absorption by phosphorous binders: A theoretical, in vitro, and in vivo study, J. Clin. Invest., 83:66-73 (1989).
Shen et al., Preparation and characterization of Fe/MgO catalysts obtained from hydrotalcite-like compounds, Catalysis Today, 30(1-3):77-82 (1996).
Shin et al., Phosphorus removal by hydrotalcite-like compounds (HTLcs), Water Sci. Technol., 34(1-2):161-8 (1996).
Sigma-Aldrich product information for Iron(III) nitrate nonanhydrate, retrieved from the Internet: <http:www.sigmaaldrich.com> on Jun. 11, 2012 (one page).
Spengler et al., Cross-linked iron dextran is an efficient oral phosphate binder in the rat, Nephrol. Dial. Transplant., 11(5):808-12 (1996).
Stamatakis et al., Influence of pH on in vitro disintegration of phosphate binders, Am. J. Kidney Dis., 32(5):808-12 (1998).
Suren, Evaluation of lubricants in the development of tablet formulation, Dansk TIDSskr. Farm 45, pp. 331-338 (1971).
Tezuka et al, The Synthesis and Phosphate Adsorptive Properties of Mg(II)-Mn(III) Layered Double Hydroxides and Their Heat-Treated Materials, Bull Chem. Soc. Jpn. 2004, 77:2101-7 (2004).
The National Kidney Foundation Kidney Disease Quality Outcomes Initiative, Clinical Practice Guidelines for Bone Metabolism and Disease in Chronic Disease, Guide 5 pp. 1, pt. 5.5 (2003).
Tichit et al., Catalysis by hydrotalcites and related materials, Cattech, 7(6):206-17 (2003).
Titulaer et al., The formation of ice between hydrotalcite particles measured by thermoporometry, Clay Minerals, 31 (2):263-77 (1996).
Toth et al., Nano-scaled inorganic/biopolymer composites: molecular modeling vistas, AIChE Annual Meeting (2005).
Toth et al., Structure and energetics of biocompatible polymer nanocomposite systems: a molecular dynamics study, Biomacromolecules, 7:1714-9 (2006).
Trifiro et al, "Hydrotalcite-like Anionic Clays (Layered Double Hydroxides)", vol. 7, chapter 8, pp. 251-291, IN: Alberti et al. (eds.) Comprehensive Supramolecular Chemistry, Pergamon, Oxford (1996).
Tsuji et al., Hydrotalcites with an extended $Al^{3+}$-substitution: synthesis, simultaneous TG-DTA-MS study, and their $CO_2$ adsorption behaviors, J. Mater. Res., 8(5):1137-42 (1993).
Ulibarri et al., Kinetics of the thermal dehydration of some layered hydroxycarbonates, Thermochimica Acta, 135:231-6 (1998).
USANA Technical Bulletin, Tablet Excipients, Jun. 1999.
Van Der Voet et al., Intestinal absorption of aluminium from antacids: a comparison between hydrotalcite and algeldrate, Clin. Tech., 24(6):545-3 (1986).
Vatier et al., Antacid activity of calcium carbonate and hydrotalcite tablets, Arzneim-Forsch/Drug Res., 44(4):514-8 (1994).
Vitkova et al., The use of some hydrophobic substances in tablet technology, Milan Chilabala, Acta Pharamceutica Hungaria, 68:336-44 (1998).
Written Opinion for PCT/GB2007/000308, Nov. 30, 2007.
Zhang et al., Phosphorous anion exchange characteristic of a pyroaurite-like compound, Inorg. Mater., 4:132-8 (1997).
Zhang et al., Synthesis and characterization of a novel nanoscale magnetic solid base catalyst involving a layered double hydroxide supported on a ferrite core, J. Solid State Chem., 177:772-80 (2004).
Zhang et al., Synthesis of Mg/Fe pyroaurite-like compounds and their anion-exchange characteristics, Inorg. Mater., 2(259):480-5 (1995).
Zhao et al., Preparation of layered double-hydroxide nanomaterials with a uniform crystalite size using a new method involving separate nucleation and aging steps, Chem. Mater., 14(10):4286-91 (2002).
Zhu et al., Adsorption of phosphate by hydrotalcite and its calcined product, Acta Mineralogica Sinica, 25(1):27-32 (2005).
Zhu et al., Different Mg to Fe ratios in the mixed metal MgFe hydroxy-carbonate compounds and the effect on phosphate binding compared with established phosphate binders, J. Pharm. Sci., 91(1):53-66 (2002).
Cargill et al., Chemical reactivity of aluminium-based pharmaceutical compounds used as phosphate-binders, J. Pharm. Pharmacol., 41 :11-16 (1989).

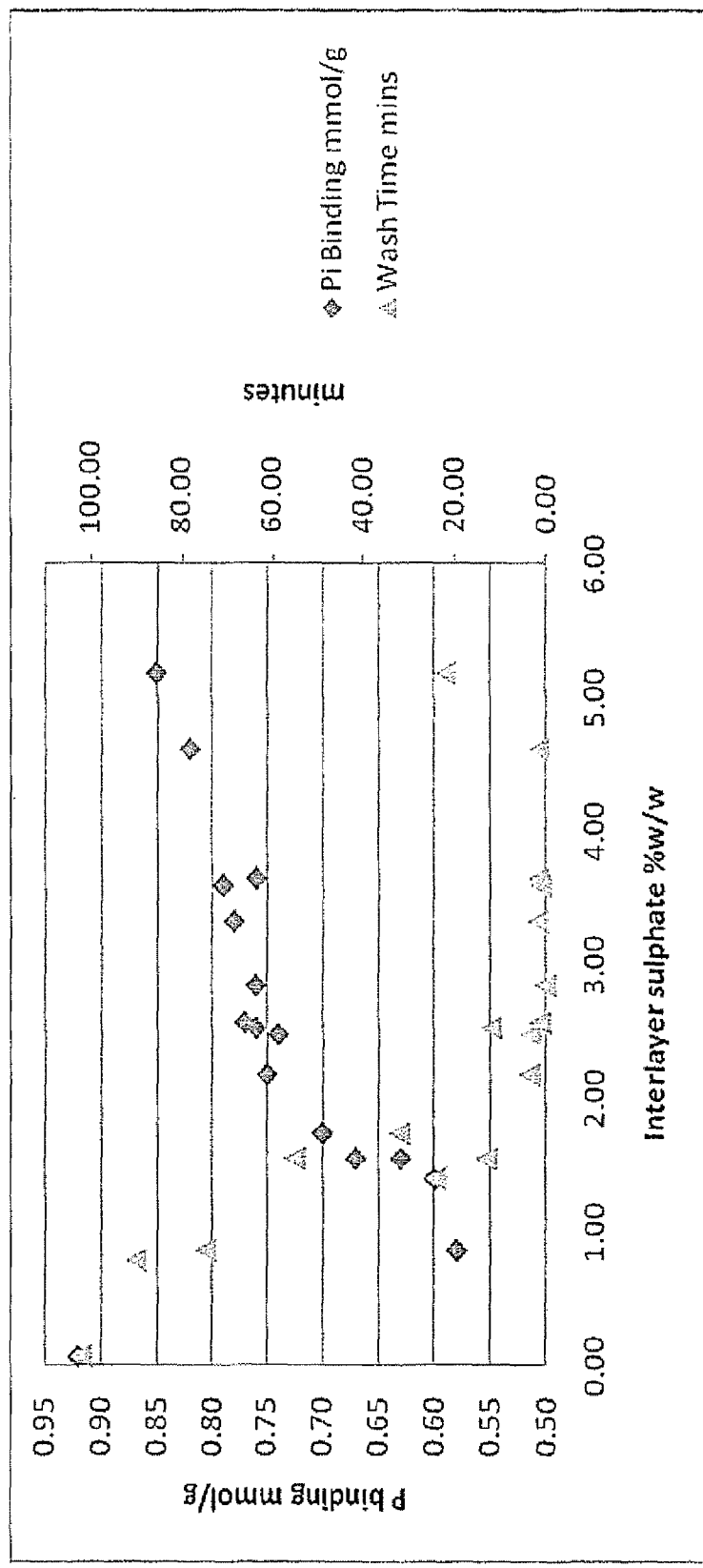
Graphical representation of data from Table 3 demonstrating preferred range between 2-5 wt% interlayer sulphate wherein phosphate binding is high and wash time low

MIXED METAL COMPOUND

This is division of U.S. patent application Ser. No. 13/388,476, which is the U.S. national phase of International Application No. PCT/GB2010/051271, filed Aug. 2, 2010, which claims the benefit of United Kingdom Patent Application Serial No. 0913525.2, filed Aug. 3, 2009, the entire disclosures of which are hereby incorporated herein by reference.

FIELD OF THE INVENTION

The present invention relates to a method for producing mixed metal compounds and to compounds prepared by these methods. These compounds may have pharmaceutical activity, especially as phosphate binders. The present invention further relates to novel mixed metal compounds. Yet further the invention relates to pharmaceutical compositions containing the above compounds and to the pharmaceutical use of the compounds.

BACKGROUND OF THE INVENTION

Hyperphosphataemia

Hyperphosphataemia is an electrolyte disturbance in which there is an abnormally elevated level of phosphate in blood. Hyperphosphataemia is frequently seen in dialysis patients, as standard dialysis regimes are unable to remove the ingested phosphate load even with a low phosphate diet, and is associated with an increased risk of death and the development of vascular calcification. The presence of hyperphosphataemia leads to hypocalcaemia, secondary hyperparathyroidism, reduced 1.25 Vit D3 and progressive metabolic bone disease. Hyperphosphataemia is ultimately responsible for the increase in vascular calcification, but recent studies have also suggested that the process may additionally be influenced by 1.25 Vit D3 and an elevated calcium-phosphate product. Patients who have chronically uncontrolled hyperphosphataemia develop progressively extensive soft tissue calcifications due to the deposit of Calcium/phosphate product into skin, joints, tendons, ligaments. Eye deposits of calcium/phosphate product have also been described.

Control of serum phosphate levels using oral phosphate binders has, therefore, become a key therapeutic target in the management of dialysis patients. These binders, taken with food, render the contained phosphate insoluble and, therefore, non-absorbable.

Phosphate Binders

Historically phosphate binders included aluminium salts. However, use of aluminium salts was found to result in further toxic complications due to aluminium accumulation, e.g., reduction in haemoglobin production, impairment in natural repair and production of bone and possible impairment of neurological/cognitive function. Renal bone disease, osteomalacia and dementia are the most significant toxicities related to the absorption of aluminium. Other aluminium compounds such as microcrystalline aluminium oxide hydroxide (boehmite) and certain hydrotalcites were proposed for this use, such as disclosed in Ookubo et al, Journal Pharmaceutical Sciences (November 1992), 81 (11), 1139-1140. However these suffer from the same drawbacks.

Calcium carbonate or calcium acetate are used as phosphate binders. However these suffer from the drawback that they tend to promote hypocalcaemia through the absorption of high amounts of ingested calcium and are linked to accelerated cardiovascular calcification which can cause serious side effects. Consequently, frequent monitoring of serum calcium levels is required during therapy with calcium-based phosphate binders. The National Kidney Foundation Kidney Disease Quality Outcomes Initiative suggests the limited use of calcium based salts (Clinical Practice Guidelines for Bone Metabolism and Disease in Chronic Kidney Disease, Guide 5, pg 1 pt 5.5). Recent efforts, therefore, have focused on the development of phosphate binders free of calcium. More recently, lanthanum carbonate and sevelamer HCl have been used as calcium-free phosphate binders. Sevelamer hydrochloride is a water-absorbing, non-absorbed hydrogel-crosslinked polyallylamine hydrochloride but because of its structure also binds certain fat-soluble vitamins and bile acids and is therefore reported in V. Autissier et al, Journal of Pharmaceutical Sciences, Vol 96, No 10, October 2007 to require large doses to be effective because it has a higher propensity for the bound phosphate to be displaced by these competing anions. A high pill burden or large tablets are often associated with poor patient compliance and this type of product is also considered relatively expensive to their calcium counter parts. Sevelamer has also been associated with GI adverse effects A. J. Hutchison et al, Drugs 2003; 63 (6), 577-596.

Lanthanum carbonate is a phosphate binder which has been shown to be as effective as calcium carbonate with lower incidence of hypocalcaemia. Long-term administration of lanthanum, a rare earth element, continues to raise safety concerns with regards to the potential accumulation of a rare earth metal in body tissue which can be enhanced in renal failure—Tilman B Druke, Seminars in Dialysis, Volume 20, Issue 4 page 329-332 July/August 2007.

Many known inorganic preparations for treatment of hyperphosphataemia are efficient phosphate binders only over a limited pH range. Moreover, particularly alkaline binders could buffer the stomach pH up to a high level at which they would not have a phosphate binding capacity.

To overcome the drawbacks associated with aluminium and also problems of efficacy over a limited pH range, WO-A-99/15189 discloses use of mixed metal compounds which are free from aluminium and which have a phosphate binding capacity of at least 30% by weight of the total weight of phosphate present, over a pH range of from 2-8.

Mixed Metal Compounds

Mixed metal compounds (mixed metal compounds) exist as so-called "Layered Double Hydroxide" (LDH) which is used to designate synthetic or natural lamellar hydroxides with two kinds of metallic cations in the main layers and interlayer domains containing anionic species. This wide family of compounds is sometimes also referred to as anionic clays, by comparison with the more usual cationic clays whose interlamellar domains contain cationic species. LDHs have also been reported as hydrotalcite-like compounds by reference to one of the polytypes of the corresponding [Mg—Al] based mineral. (See "Layered Double Hydroxides: Present and Future", ed, V Rives, 2001 pub. Nova Science).

By mixed metal compound, it is meant that the atomic structure of the compound includes the cations of at least two different metals distributed uniformly throughout its structure. The term mixed metal compound does not include mixtures of crystals of two salts, where each crystal type only includes one metal cation. Mixed metal compounds are typically the result of coprecipitation from solution of different single metal compounds in contrast to a simple solid physical mixture of two different single metal salts. Mixed metal compounds as used herein include compounds of the same metal type but with the metal in two different valence states e.g. Fe(II) and Fe(III) as well as compounds containing more than two different metal types in one compound.

The mixed metal compound may also comprise amorphous (non-crystalline) material. By the term amorphous is meant either crystalline phases which have crystallite sizes below the detection limits of x-ray diffraction techniques, or crystalline phases which have some degree of ordering, but which do not exhibit a crystalline diffraction pattern and/or true amorphous materials which exhibit short range order, but no long-range order.

Mixed metal compounds provide unique challenges in using inorganic material for pharma use and in particular for phosphate binding and which are free of Al.

For example, use of mixed metal compound for attaining phosphate therapeutic effects (or other pharma functional use) depends on surface processes such as physisorption (ion-exchange) and chemisorption (formation of a chemical bond) which is atypical for a drug; the therapeutic activity of most drugs are based on organic compounds which are typically more soluble.

Yet further, high daily and repeated long-term (chronic) dosages are required for kidney patients but their total daily pill count requires a low tablet burden due to restricted fluid intake. Consequently, high dosage of drug substance is required in final product (e.g. tablet) and the final product is therefore very sensitive to the properties of the mixed metal compound drug substance, unlike normal formulations. This means that the properties of the tablet, including key physical properties, and the tablet manufacturing processes, such as granulation, are often primarily influenced by the properties of the mixed metal compound active substance rather than solely by those of the excipients. In order to be able to manufacture a pharmaceutical product comprising such significant quantities of mixed metal compound with the control and consistency necessary for pharmaceutical use, a means of controlling an array of opposing chemical and physical properties of the mixed metal compound is essential.

Therefore, considering these requirements, manufacture of such materials, particularly at large scale, presents significant problems. A number of these problems are described below.

Ageing

The ageing process (growth of crystallites) generally increases with (unintended) increased processing and handling as well as by the process whereby the crystallites are intentionally grown by a combination of agitation and heat-treatment of the reaction slurry before filtration. Control and prevention of crystal growth can therefore be difficult.

The teachings of MgAl mixed metal compounds which are manufactured in the aged form for medical applications such as antacids, do not address the problems of manufacture of unaged mixed metal compounds (on a larger scale), when the unaged form is required, for example to maintain therapeutic activity of phosphate binding. Furthermore, when replacing Al for Fe we found that the mixed metal compound changes properties such as to becoming more difficult to wash and mill on a commercial scale.

Al-containing mixed metal compounds that are intentionally aged to increase crystal growth have previously been manufactured on a large scale. In contrast, there appear to be no examples of large scale manufacture of unaged Al-free mixed metal compounds.

The method disclosed in WO99/15189 relates to Al free mixed metal compounds and includes examples of unaged and aged materials. However, the products disclosed in this publication are provided at relatively small scale, WO99/15189 does not address the problems of provision of product at significant scale while avoiding aging of the product.

The manufacture of unaged mixed metal Mg:Fe compounds (Mg:Fe defined by molar ratio hereinafter) on a large scale is problematic for a number of reasons. For example, the manufacture of unaged mixed metal Mg:Fe compounds is problematic when using conventional filtration methods. Unaged material results in a high pressure drop through the filter cake during isolation leading to low filtration rates or yield losses during conventional filtration. Furthermore, these types of metal Mg:Fe compounds typically have small slurry particle size and as such it is difficult to carry out isolation whilst minimising ageing. For example, small particles can give rise to increased processing times and/or handling issues.

Furthermore, too much processing and handling (e.g. milling and overdrying) can present changes that are unacceptable in the final mixed metal Mg:Fe compound. In particular with such compounds, it is important to dry the material carefully as it is easy to change the surface area or internal pore volume and hence change the therapeutic activity. These typical morphology properties are important characteristics affecting both the quality of the final mixed metal compound and the downstream manufacturing processes used to produce the final formulated pharmaceutical product containing the mixed metal compound.

If processed incorrectly mixed metal compounds can become unacceptably hard. This can lead to consequent issues of decreased milling rates and higher energy input to achieve a given particle size. This 'knock on' effect to the processing may affect process throughput and result in overworking the material and consequential ageing.

Methods for lab-scale preparations of MgFe LDH's are disclosed in art such as U.S. Pat. No. 4,629,626; Duan X, Evans D. G., Chem. Commun., 2006, 485-496; W. Meng et al, J. Chem. Sci., Vol. 117, No. 6 Nov. 2005, pp. 635-639; Carlino, Chemistry between the sheets, Chemistry in Britain, September 1997, pp 59-62; Hashi et al, Clays and Clay Minerals (1983) pp 152-15; Raki et al, 1995, 7, 221-224; Ookubo et al, Langmuir (1993), 9, pp 1418-1422I; Zhang et al. Inorganic Materials Vol. 4 March 132-138 (1997), Reichle, Solid States tonics, 22, pp 135-141 (1986); Ulibarri et al, Kinetics of the Thermal Dehydration of some layered Hydrocycarbonates, Thermochimica Acta, pp 231-236 (1988); Hansen et al, Applied Clay Science 10 (1995) pp 5-19.

These methods describe lab-scale preparations only. Furthermore, these materials are obtained via a process which includes an ageing step (i.e. a deliberate process of increasing crystal growth which is typically achieved by heating the reaction slurry over a prolonged period of time such as by a hydrothermal process). In general, the compounds of the prior art also contain substantially more than one type of anion in the interlayer region.

Methods for large scale manufacturing of MgAl hydrotalcites are disclosed in art such as U.S. Pat. No. 3,650,704, WO-A-20081129034 and WO-A-93/22237. However, these describe the process for obtaining materials in the aged form resulting in a larger crystallite size (of above 200 Angstrom) and are not free of aluminium.

Aspects of the invention are defined in the appended claims.

SUMMARY ASPECTS OF THE INVENTION

In one aspect the present invention provides a method of producing a mixed metal compound comprising
at least $Mg^{2+}$ and at least $Fe^{3+}$
having an aluminium content of less than 10000 ppm,
having an average crystal size of less than 20 nm (200 Å)
comprising the steps of:

(a) combining a $Mg^{2+}$ salt and a $Fe^{3+}$ salt with $Na_2CO_3$ and NaOH to produce a slurry, wherein the pH of the slurry is maintained at from 9.5 to 11, and wherein the $Na_2CO_3$ is provided at an excess of 0 to 4.0 moles than is required to complete the reaction
(b) subjecting the slurry to mixing under conditions providing a power per unit volume of 0.03 to 1.6 kW/m³
(c) separating the mixed metal compound from the slurry, to obtain a crude product having a dry solid content of at least 10 wt %
(d) drying the crude product either by
  (i) heating the crude product to a temperature of no greater than 150° C. and sufficient to provide a water evaporation rate of 0.05 to 1.5 kg water per hour per kg of dry product, or
  (ii) exposing the crude product to rapid drying at a water evaporation rate of 500 to 50000 kg water per hour per kg of dry product.

In one aspect the present invention provides a method of producing a mixed metal compound comprising
at least $Mg^{2+}$ and at least $Fe^{3+}$
having an aluminium content of less than 10000 ppm,
having an average crystal size of less than 20 nm (200 Å) comprising the steps of:
(a) combining a $Mg^{2+}$ salt and a $Fe^{3+}$ salt with $Na_2CO_3$ and NaOH to produce a slurry, wherein the pH of the slurry is maintained at from 9.5 to 11, and wherein the $Na_2CO_3$ is provided at an excess of 2.0 to 4.0 moles than is required to complete the reaction
(b) subjecting the slurry to mixing under conditions providing a power per unit volume of 0.03 to 1.6 kW/m³
(c) separating the mixed metal compound from the slurry, to obtain a crude product having a dry solid content of at least 10 wt %
(d) drying the crude product either by
  (i) heating the crude product to a temperature of no greater than 150° C. and sufficient to provide a water evaporation rate of 0.05 to 1.5 kg water per hour per kg of dry product, or
  (ii) exposing the crude product to rapid drying at a water evaporation rate of 500 to 50000 kg water per hour per kg of dry product.

In one aspect the present invention provides a method of producing a mixed metal compound comprising
at least $Mg^{2+}$ and at least $Fe^{3+}$
having an aluminium content of less than 10000 ppm,
having an average crystal size of less than 20 nm (200 Å);
the method comprising the step of:
(a) combining a $Mg^{2+}$ salt and a $Fe^{3+}$ salt with $Na_2CO_3$ and NaOH to produce a slurry, wherein the slurry is maintained to a temperature between 15 and 30° C., and:
  (i) wherein the pH of the slurry is maintained at from 9.5 to less than 9.8, and wherein the $Na_2CO_3$ is provided at an excess of greater than 1.0 to no greater than 5.0 moles than is required to complete the reaction; or
  (ii) wherein the pH of the slurry is maintained at from 9.5 to less than 10, and wherein the $Na_2CO_3$ is provided at an excess of greater than 1.0 to no greater than 4.0 moles than is required to complete the reaction; or
  (iii) wherein the pH of the slurry is maintained at from 9.5 to no greater than 10.1, and wherein the $Na_2CO_3$ is provided at an excess of greater than 1.0 to no greater than 2.7 moles than is required to complete the reaction; or
  (iv) wherein the pH of the slurry is maintained at from 9.5 to 10.5, and wherein the $Na_2CO_3$ is provided at an excess of from greater than 1.0 to no greater than 2.0 moles than is required to complete the reaction; or
  (v) wherein the pH of the slurry is maintained at from greater than 9.5 to no greater than 11, and wherein the $Na_2CO_3$ is provided at an excess of from 0.0 to no greater than 1.0 moles than is required to complete the reaction;
or the method comprising the step of:
(b) combining a $Mg^{2+}$ salt and a $Fe^{3+}$ salt with $Na_2CO_3$ and NaOH to produce a slurry, wherein the slurry is maintained to a temperature from 30 to 60° C., and:
  (i) wherein the pH of the slurry is maintained at from greater than 9.5 to less than 11, and wherein the $Na_2CO_3$ is provided at an excess of greater than 0 to less than 2 moles than is required to complete the reaction; or
  (ii) wherein the pH of the slurry is maintained at from greater than 9.5 to less than 10.5, and wherein the $Na_2CO_3$ is provided at an excess of greater than 0 to less than 2.7 moles than is required to complete the reaction; or
  (iii) wherein the pH of the slurry is maintained at from greater than 9.5 to less than 10, and wherein the $Na_2CO_3$ is provided at an excess of greater than 0 to less than 4 moles than is required to complete the reaction.

In one aspect the present invention provides a method of producing a mixed metal compound comprising
at least $Mg^{2+}$ and at least $Fe^{3+}$
having an aluminium content of less than 10000 ppm,
having an average crystal size of less than 20 nm (200 Å),
the method comprising the step of:
(a) combining a $Mg^{2+}$ salt and a $Fe^{3+}$ salt with $Na_2CO_3$ and NaOH to produce a slurry, wherein the slurry is maintained to a temperature between 15 and 30° C., and:
  (i) wherein the pH of the slurry is maintained at from 9.5 to less than 9.8, and wherein the $Na_2CO_3$ is provided at an excess of greater than 2.0 to no greater than 4.0 moles than is required to complete the reaction; or
  (ii) wherein the pH of the slurry is maintained at from 9.5 to less than 10.3, and wherein the $Na_2CO_3$ is provided at an excess of greater than 2.0 to less than 4.0 moles than is required to complete the reaction; or
  (iii) wherein the pH of the slurry is maintained at from greater than 9.8 to no greater than 10.5, and wherein the $Na_2CO_3$ is provided at an excess of greater than 1.0 to less than 2.7 moles than is required to complete the reaction; or
  (iv) wherein the pH of the slurry is maintained at greater than 9.8 to less than 10.3, and wherein the $Na_2CO_3$ is provided at an excess of from 1.0 to less than 4.0 moles than is required to complete the reaction;
or the method comprising the step of:
(b) combining a $Mg^{2+}$ salt and a $Fe^{3+}$ salt with $Na_2CO_3$ and NaOH to produce a slurry, wherein the slurry is maintained to a temperature from 30 to 65° C., and:
  (i) wherein the pH of the slurry is maintained at from 9.5 to no greater than 10.5, and wherein the $Na_2CO_3$ is provided at an excess of greater than 0 to less than 2.7 moles than is required to complete the reaction; or
  (ii) wherein the pH of the slurry is maintained at from 9.5 to less than 10, and wherein the $Na_2CO_3$ is provided at an excess of greater than 0 to less than 4 moles than is required to complete the reaction.

In one aspect the present invention provides a mixed metal compound comprising
at least $Mg^{2+}$ and at least $Fe^{3+}$
having an aluminium content of less than 10000 ppm,
having an average crystal size of less than 20 nm (200 Å),
wherein the compound is obtained or obtainable by a method comprising the steps of
- (a) combining a $Mg^{2+}$ salt and a $Fe^{3+}$ salt with $Na_2CO_3$ and NaOH to produce a slurry, wherein the pH of the slurry is maintained at from 9.5 to 11, and wherein the $Na_2CO_3$ is provided at an excess of 0 to 4.0 moles than is required to complete the reaction
- (b) subjecting the slurry to mixing under conditions providing a power per unit volume of 0.03 to 1.6 kW/m³
- (c) separating the mixed metal compound from the slurry, to obtain a crude product having a dry solid content of at least 10 wt %
- (d) drying the crude product either by
  - (i) heating the crude product to a temperature of no greater than 150° C. and sufficient to provide a water evaporation rate of 0.05 to 1.5 kg water per hour per kg of dry product, or
  - (ii) exposing the crude product to rapid drying at a water evaporation rate of 500 to 50000 kg water per hour per kg of dry product.

In one aspect the present invention provides a mixed metal compound comprising
at least $Mg^{2+}$ and at least $Fe^{3+}$
having an aluminium content of less than 10000 ppm,
having an average crystal size of less than 20 nm (200 Å),
wherein the compound is obtained or obtainable by a method comprising the steps of:
- (a) combining a $Mg^{2+}$ salt and a $Fe^{3+}$ salt with $Na_2CO_3$ and NaOH to produce a slurry, wherein the pH of the slurry is maintained at from 9.5 to 11, and wherein the $Na_2CO_3$ is provided at an excess of 2.0 to 4.0 moles than is required to complete the reaction
- (b) subjecting the slurry to mixing under conditions providing a power per unit volume of 0.03 to 1.6 kW/m³
- (c) separating the mixed metal compound from the slurry, to obtain a crude product having a dry solid content of at least 10 wt %
- (d) drying the crude product either by
  - (i) heating the crude product to a temperature of no greater than 150° C. and sufficient to provide a water evaporation rate of 0.05 to 1.5 kg water per hour per kg of dry product, or
  - (ii) exposing the crude product to rapid drying at a water evaporation rate of 500 to 50000 kg water per hour per kg of dry product.

In one aspect the present invention provides a mixed metal compound comprising
at least $Mg^{2+}$ and at least $Fe^{3+}$
having an aluminium content of less than 10000 ppm,
having an average crystal size of less than 20 nm (200 Å),
wherein the compound is obtained or obtainable by a method comprising the steps of:
- (a) combining a $Mg^{2+}$ salt and a $Fe^{3+}$ salt with $Na_2CO_3$ and NaOH to produce a slurry, wherein the slurry is maintained to a temperature between 15 and 30° C., and:
  - (i) wherein the pH of the slurry is maintained at from 9.5 to less than 9.8, and wherein the $Na_2CO_3$ is provided at an excess of greater than 1.0 to no greater than 5.0 moles than is required to complete the reaction; or
  - (ii) wherein the pH of the slurry is maintained at from 9.5 to less than 10, and wherein the $Na_2CO_3$ is provided at an excess of greater than 1.0 to no greater than 4.0 moles than is required to complete the reaction, or
  - (iii) wherein the pH of the slurry is maintained at from 9.5 to no greater than 10.1, and wherein the $Na_2CO_3$ is provided at an excess of greater than 1.0 to no greater than 2.7 moles than is required to complete the reaction; or
  - (iv) wherein the pH of the slurry is maintained at from 9.5 to 10.5, and wherein the $Na_2CO_3$ is provided at an excess of from greater than 1.0 to no greater than 2.0 moles than is required to complete the reaction; or
  - (v) wherein the pH of the slurry is maintained at from greater than 9.5 to no greater than 11, and wherein the $Na_2CO_3$ is provided at an excess of from 0.0 to no greater than 1.0 moles than is required to complete the reaction or by the method comprising the step of:
- (b) combining a $Mg^{2+}$ salt and a $Fe^{3+}$ salt with $Na_2CO_3$ and NaOH to produce a slurry, wherein the slurry is maintained to a temperature from 30 to 60° C., and:
  - (i) wherein the pH of the slurry is maintained at from greater than 9.5 to less than 11, and wherein the $Na_2CO_3$ is provided at an excess of greater than 0 to less than 2 moles than is required to complete the reaction; or
  - (ii) wherein the pH of the slurry is maintained at from greater than 9.5 to less than 10.5, and wherein the $Na_2CO_3$ is provided at an excess of greater than 0 to less than 2.7 moles than is required to complete the reaction; or
  - (iii) wherein the pH of the slurry is maintained at from greater than 9.5 to less than 10, and wherein the $Na_2CO_3$ is provided at an excess of greater than 0 to less than 4 moles than is required to complete the reaction.

In one aspect the present invention provides a mixed metal compound comprising
at least $Mg^{2+}$ and at least $Fe^{3+}$
having an aluminium content of less than 10000 ppm,
having an average crystal size of less than 20 nm (200 Å),
wherein the compound is obtained or obtainable by a method comprising the steps of
- (a) combining a $Mg^{2+}$ salt and a $Fe^{3+}$ salt with $Na_2CO_3$ and NaOH to produce a slurry, wherein the slurry is maintained to a temperature between 15 and 30° C., and:
  - (i) wherein the pH of the slurry is maintained at from 9.5 to less than 9.8, and wherein the $Na_2CO_3$ is provided at an excess of greater than 2.0 to no greater than 4.0 moles than is required to complete the reaction; or
  - (ii) wherein the pH of the slurry is maintained at from 9.5 to less than 10.3, and wherein the $Na_2CO_3$ is provided at an excess of greater than 2.0 to less than 4.0 moles than is required to complete the reaction; or
  - (iii) wherein the pH of the slurry is maintained at from greater than 9.8 to no greater than 10.5, and wherein the $Na_2CO_3$ is provided at an excess of greater than 1.0 to less than 2.7 moles than is required to complete the reaction; or
  - (iv) wherein the pH of the slurry is maintained at greater than 9.8 to less than 10.3, and wherein the $Na_2CO_3$ is provided at an excess of from 1.0 to less than 4.0 moles than is required to complete the reaction;

or by the method comprising the step of:
- (b) combining a $Mg^{2+}$ salt and a $Fe^{3+}$ salt with $Na_2CO_3$ and NaOH to produce a slurry, wherein the slurry is maintained to a temperature from 30 to 65° C., and.

(i) wherein the pH of the slurry is maintained at from 9.5 to no greater than 10.5, and wherein the $Na_2CO_3$ is provided at an excess of greater than 0 to less than 2.7 moles than is required to complete the reaction; or (ii) wherein the pH of the slurry is maintained at from 9.5 to less than 10, and wherein the $Na_2CO_3$ is provided at an excess of greater than 0 to less than 4 moles than is required to complete the reaction.

In one aspect the present invention provides a mixed metal compound comprising
at least $Mg^{2+}$ and at least $Fe^{3+}$,
wherein
the molar ratio of $Mg^{2+}$ to $Fe^{3+}$ is 2.5.1 to 1.5:1,
the mixed metal compound has an aluminium content of less than 10000 ppm,
the average crystal size of the mixed metal compound is from 10 to 20 nm (100 to 200 Å),
and the d50 average particle size of the mixed metal compound is less than 300 μm.

In one aspect the present invention provides a mixed metal compound comprising at least $Mg^{2+}$ and at least $Fe^{3+}$,
wherein
the molar ratio of $Mg^{2+}$ to $Fe^{3+}$ is 2.5:1 to 1.5:1,
the mixed metal compound has an aluminium content of less than 10000 ppm, the average crystal size of the mixed metal compound is from 10 to 20 nm (100 to 200 Å), and the water pore volume of the mixed metal compound is from 0.25 to 0.7 $cm^3/g$ of mixed metal compound.

In one aspect the present invention provides a mixed metal compound comprising at least $Mg^{2+}$ and at least $Fe^{3+}$,
wherein
the molar ratio of $Mg^{2+}$ to $Fe^{3+}$ is 2.5:1 to 1.5:1, the mixed metal compound has an aluminium content of less than 10000 ppm, the average crystal size of the mixed metal compound is from 10 to 20 nm (100 to 200 Å), and the interlayer sulphate content of the compound is from 1.8 to 5 wt %.

In one aspect the present invention provides a mixed metal compound comprising at least $Mg^{2+}$ and at least $Fe^{3+}$,
wherein
the molar ratio of $Mg^{2+}$ to $Fe^{3+}$ is 2.5:1 to 1.5:1,
the mixed metal compound has an aluminium content of less than 10000 ppm, the average crystal size of the mixed metal compound is from 10 to 20 nm (100 to 200 Å), and the interlayer sulphate content of the compound is from 1.8 to 3.2 wt %.

In one aspect the present invention provides a mixed metal compound comprising at least $Mg^{2+}$ and at least $Fe^{3+}$,
wherein
the molar ratio of $Mg^{2+}$ to $Fe^{3+}$ is 2.5:1 to 1.5:1,
the mixed metal compound has an aluminium content of less than 10000 ppm,
the average crystal size of the mixed metal compound is less than 20 nm (200 Å), and the interlayer sulphate content of the compound is from 1.8 to 5 wt %.

In one aspect the present invention provides a mixed metal compound comprising at least $Mg^{2+}$ and at least $Fe^{3+}$,
wherein
the molar ratio of $Mg^{2+}$ to $Fe^{3+}$ is 2.5:1 to 1.5:1,
the mixed metal compound has an aluminium content of less than 10000 ppm,
the average crystal size of the mixed metal compound is less than 20 nm (200 Å),
and the interlayer sulphate content of the compound is from 1.8 to 3.2 wt %.

In one aspect the present invention provides a mixed metal compound comprising at least $Mg^{2+}$ and at least $Fe^{3+}$,
wherein
the molar ratio of $Mg^{2+}$ to $Fe^{3+}$ is 2.5:1 to 1.5:1,
the mixed metal compound has an aluminium content of less than 10000 ppm, the average crystal size of the mixed metal compound is less than 20 nm (200 Å), and the surface area is from 80 to 145 $m^2$ per gram of compound.

In one aspect the present invention provides a mixed metal compound comprising at least $Mg^{2+}$ and at least $Fe^{3+}$,
wherein
the molar ratio of $Mg^{2+}$ to $Fe^{3+}$ is 2.5:1 to 1.5:1,
the mixed metal compound has an aluminium content of less than 10000 ppm,
the average crystal size of the mixed metal compound is from 10 to 20 nm (100 to 200 Å),
the surface area is from 40 to 80 $m^2$ per gram of compound.

In one aspect the present invention provides a mixed metal compound as described herein for use as a medicament.

In one aspect the present invention provides a mixed metal compound as described herein for binding phosphate.

In one aspect the present invention provides a mixed metal compound as described herein for use in the treatment of hyperphosphataemia.

In one aspect the present invention provides a pharmaceutical composition comprising a mixed metal compound as described herein and optionally one or more pharmaceutically acceptable adjuvants, excipients, diluents or carriers.

Some Advantages

The present method provides a process which may be operated on a large scale to provide for a pharmaceutical phosphate binding drug of consistent composition which is stable upon storage and can be easily formulated and/or packaged. Moreover, the present method provides for control of key properties such as average crystal size, particle size, surface area, other morphology parameters (such as pore volume) and degree of hydration—all of which are important for such manufacture.

Al-free mixed metal compounds containing Fe and Mg typically have a clay-like structure. This presents limitations in view of the difficult filtration of such products which in turn affect the viability of a controlled process.

The present method provides a process which allows for manufacture of a consistent 'Al-free' mixed metal compounds suitable for use in final product formulations (e.g. tablet formulations etc). The therapeutic effect of the final products and the ability to process the mixed metal compounds into a final product consistently, depend on the physical (i.e. particle- and crystallite-size) and chemical (i.e. composition) properties of the mixed metal compound. The present process provides a method for a consistent manufacture of pharmaceutical-grade 'Al-free' mixed metal compounds with consistent particle- and crystallite-size.

In one aspect the present invention provides a mixed metal compound comprising at least $Mg^{2+}$ and at least $Fe^{3+}$, wherein the molar ratio of $Mg^{2+}$ to $Fe^{3+}$ is 2.5:1 to 1.5:1, the mixed metal compound has an aluminium content of less than 10000 ppm, the average crystal size of the mixed metal compound is from 10 to 20 nm (100 to 200 Å), and the interlayer sulphate content of the compound is from 1.8 to 5 wt % (such as from 1.8 to 3.2 wt %).

For mixed metal compounds, maintaining the target metal molar ratio (Mg:Fe) during the reaction whilst meeting the above criteria is difficult as this is affected by the way the material is processed. We found that correct stoichiometry is not only determined by the correct ratios of the starting materials but also by pH for the reaction; i.e. when a pH is below pH 9.5 incomplete precipitation of magnesium may occur and too high a pH (i.e. above pH 11) risks loss of iron.

Mixed metal compounds can have more than one type of anion within the interlayer region. This can introduce impurities which are undesirable when considering pharma use and we found can also affect therapeutic activity (of phosphate binding). We have also found, surprisingly, that the type and amount of anions present in the interlayer region has a marked effect on the time taken to complete separation and washing of the unaged product, particularly for commercial scale manufacture. For example, we have found that at low (below 1.8% wt) interlayer sulphate levels, separation and washing times increase significantly.

We found that when the amount of interlayer sulphate is maintained from 1.8 to 5 wt % (such as from 1.8 to 3.2 wt %) phosphate binding of more than 0.60 mmol phosphate/g compound can be obtained whilst maintaining low filtration and wash times.

The combination of process parameters of the present method provides for the preparation of mixed metal compounds which have controlled sulphate ($SO_4$) levels in the interlayer region.

Soluble $SO_4$ in the form of $Na_2SO_4$ salt can be readily removed by washing whereas the interlayer sulphate cannot be removed by washing with water.

We found that the interlayer sulphate could be reduced without necessarily increasing the filtration and wash times by reslurrying the dried compound in a solution containing carbonate enabling ion-exchange; however, this meant an additional reaction, isolation and drying step and generally lead to a decrease in phosphate binding. Furthermore, this route would result in a longer overall time to manufacture. This route to control interlayer sulphate is therefore less preferred. Alternatively, the interlayer sulphate may be reduced by washing or reslurrying the filtercake after isolation with a solution containing carbonate instead of water Again this would lead to an additional process step and is less preferred.

We found that by control of the process parameters as described herein, one may prepare a mixed metal compound having low levels of impurities, and in particular heavy metal impurities, without the need to perform purification to remove such impurities. The present invention may provide a process for preparing a mixed metal compound having a lead content of less than 1 ppm and/or a chromium content of less than 30 ppm and/or a total heavy metal content of less than 10 ppm and/or a sodium content expressed as $Na_2O$ of less than 0.5 wt %. In one aspect the mixed metal compound has a total heavy metal content of less than 25 ppm, preferably less than 10 ppm. For example the present invention may provide a process for preparing a mixed metal compound having a total heavy metal content of less than 15 ppm, a lead content less than 10 ppm, a chromium level less than 35 ppm and a sodium content (expressed as $Na_2O$) of less than 1 wt %.

Heavy metals content as referred to herein are the group consisting of As, Cd, Pb, Hg, Sb, Mo and Cu. Thus, reference to total heavy metal content will be understood to mean the combined content of As, Cd, Pb, Hg, Sb, Mo and Cu.

WO99/15189 teaches the preparation of a slurry at pH above 10 using a 5 mole $Na_2CO_3$: 12 mole NaOH ratio which equates to an excess of 4 mole $Na_2CO_3$ than required to complete the reaction equation:

$$4MgSO_4+Fe_2(SO_4)_3+12NaOH+5Na_2CO_3 \rightarrow Mg_4Fe_2(OH)_{12}.CO_3.nH_2O+7Na_2SO_4+4Na_2CO_3.$$

We have found that this excess of 4 mole $Na_2CO_3$ is not preferred, especially when precipitated at a pH of more than 10 and at room temperature. We found that this combination results in reduced solubility of the carbonate in the reactant solution at the desired reaction temperatures, provides poor filtration and wash times. We have found that when preparing unaged material of 2:1 Mg:Fe molar ratio according to method of WO99/15189 that this material was more difficult to separate and wash when manufactured at scale whilst maintaining good phosphate binding. This resulted in loss of batches as a result of material being out of specification.

Sodium carbonate not only provides the carbonate for the anion-exchange sites, but also acts as a pH buffer which assists pH control during precipitation. The ability to maintain an accurate precipitation pH is considerably increased when $Na_2CO_3$ is present. However, we have also found that the filtration rate significantly increases when $Na_2CO_3$ is reduced from a 2.7 mole excess to zero excess. A high filtration rate is advantageous when seeking to manufacture an unaged form of the Mg Fe mixed metal compounds. Such materials can be difficult to filter. Also decreasing the $Na_2CO_3$ further, such as below the 2.7 mole excess, may result in less precise pH control as well as increasing the level of sulphate anions present in the interlayer region. As a consequence of the above, we have identified that there is a complex interrelationship between pH, mole excess $Na_2CO_3$ and the temperature at which the slurry is maintained, all of which are important to maintain good phosphate binding and filtration and or wash times. In particular we have determined that in order to obtain phosphate binding above 0.60 mmol phosphate/g compound and maintain good filtration and wash time it is preferred to produce a slurry, wherein a temperature is maintained between 15 and 30° C.

(i) wherein the pH of the slurry is maintained at from 9.5 to less than 9.8, and wherein the $Na_2CO_3$ is provided at an excess of greater than 1.0 to no greater than 5.0 moles than is required to complete the reaction; or (ii) wherein the pH of the slurry is maintained at from 9.5 to less than 10, and wherein the $Na_2CO_3$ is provided at an excess of greater than 1.0 to no greater than 4.0 moles than is required to complete the reaction; or (iii) wherein the pH of the slurry is maintained at from 9.5 to no greater than 10.1, and wherein the $Na_2CO_3$ is provided at an excess of greater than 1.0 to no greater than 2.7 moles than is required to complete the reaction; or (iv) wherein the pH of the slurry is maintained at from 9.5 to 10.5, and wherein the $Na_2CO_3$ is provided at an excess of from greater than 1.0 to no greater than 2.0 moles than is required to complete the reaction; or (v) wherein the pH of the slurry is maintained at from greater than 9.5 to no greater than 11, and wherein the $Na_2CO_3$ is provided at an excess of from 0.0 to no greater than 1.0 moles than is required to complete the reaction.

Alternatively, a $Mg^{2+}$ salt and a $Fe^{3+}$ salt can be combined with $Na_2CO_3$ and NaOH to produce a slurry, wherein the slurry is maintained to a temperature from 30 to 60° C.

(i) wherein the pH of the slurry is maintained at from greater than 9.5 to less than 11, and wherein the $Na_2CO_3$ is provided at an excess of greater than 0 to less than 2 moles than is required to complete the reaction, or (ii) wherein the pH of the slurry is maintained at from greater than 9.5 to less than 10.5, and wherein the $Na_2CO_3$ is provided at an excess of greater than 0 to less than 2.7 moles than is required to complete the reaction, or (iii) wherein the pH of the slurry is maintained at from greater than 9.5 to less than 10, and wherein the $Na_2CO_3$ is provided at an excess of greater than 0 to less than 4 moles than is required to complete the reaction.

Furthermore, we have found that in order to avoid the presence of additional crystalline phases in the compound (i.e. phases other than hydrotalcite-type as detected by powder X-ray Diffraction) it is necessary to wash the product to such an extent that the unbound sulphate ($SO_4$) i.e. in form of sodium sulphate ($Na_2SO_4$) is maintained below 1.5 wt % (when expressed as $Na_2SO_4$) and preferably less than 1 wt % (when expressed as $SO_4$). This conversely can only be achieved when a small amount of the interlayer sulphate is maintained such as to enable effective filtration and washing at commercial scale The present method is a co-precipitation process. Such processes encourage the formation of different crystalline phases in addition to the hydrotalcite phase. For use as an active in pharmaceutical formulations, there is the requirement to be able to identify and control the phase of interest. The present method provides for the preparation of mixed metal compounds which contain less of (or are substantially free of) any other crystalline phases as determined by the absence of XRD diffraction lines except those attributed to a hydrotalcite phase. The hydrotalcite phase had the following diffraction X-ray diffraction analysis: dA ('d' spacings) 7.74*, 3.86*, 3.20, 2.62*, 2.33*, 1.97*, 1.76, 1.64, 1.55*, 1.52*, 1.48, 1.44*, 1.40, of which the peaks marked * are the eight most intense peaks typically seen in the unaged samples. The remaining five peaks are only resolved in more crystalline samples, typically as a result of ageing.

In summary, we have found that a total process of production (from reaction to drying) is provided such as to prevent growth of the crystallite size (above average crystal size 200 Å) in order to maintain the phosphate binding activity without significantly hindering the process of isolation and washing of the compound. This was achieved by careful control of process conditions and a specific selection of the same such as by controlling interlayer sulphate from 1.8 to 5 wt % (such as from 1.8 to 3.2 wt %) which in turn can be controlled via selection of excess $Na_2CO_3$ reaction pH and reaction slurry temperature.

In one aspect the present invention provides a mixed metal compound comprising at least $Mg^{2+}$ and at least $Fe^{3+}$, wherein the molar ratio of $Mg^{2+}$ to $Fe^{3+}$ is 1.5:1 to 2.5:1, the mixed metal compound has an aluminium content of less than 10000 ppm, the average crystal size of the mixed metal compound is from 10 to 20 nm (100 to 200 Å), and the d50 average particle size of the mixed metal compound is less than 300 µm. We have found surprisingly that this unaged compound with such average crystal size range and with milled particle size less than 300 microns, has the advantages of good, controlled phosphate binding (above 0.60 mmol phosphate/g compound) whilst maintaining low magnesium release (less than 0.2 mmol magnesium/g compound). Above 300 micron particle size we have found that the phosphate binding decreases markedly and magnesium release increases to above 0.2 mmol magnesium/g compound.

We have found that an average crystal size of the mixed metal compound of less than 20 nm (200 Å) and high surface area (80-145 $m^2/g$) can be manufactured using a process comprising a short residence drying step such that the resultant material has both small average crystal size and high surface area but also importantly has a higher phosphate binding capacity as well as a lower magnesium release when compared at similar d50 average particle size to that of the low surface area (40-80 $m^2/g$) material; even when the material is not milled further. The requirement for no milling has the advantage of reduced processing steps. A further advantage is that such material can be suitable for tabletting processes without the need for wet granulation. A further advantage is that material manufactured via the short residence route may be exposed to temperatures above 150° C. because the residence time (less than 5 minutes) of the product in the dryer is generally too short to enable any decomposition of the compound.

The mixed metal compound having an average crystal size of from 10 to 20 nm (100 to 200 Å) and surface area 40-80 $m^2/g$ has the benefit of good stability in particular phosphate binding, on storage. This product has the additional benefit of providing a smaller tablet size (i.e. less than 500 $mm^3$ for 500 mg compound) thereby improving tablet pill burden; a prevalent issue within the treatment of renal patients. The material of surface area 40-80 $m^2/g$ which required micronisation can be manufactured at commercial scale, including milling of the material, with minimal impact on aging of the material as reflected in maintaining a small average crystal size of below 200 Å. If the crystallite size is less than 100 Å it presents difficulties in milling to small particle size of for example, problems with trace metal impurities, milling rate and decomposition of the product and over-drying of the product Furthermore an additional surprising benefit is that such materials also exhibit no significant reduction in the uptake rate of phosphate, despite the lower surface areas. This facet can be important when considering such materials for pharmaceutical applications in which the binding of phosphate needs to be rapid such as renal care. We have found that the material described above bind 80% phosphate within 10 minutes (Test Method 3).

As for the product of 10 to 20 nm (100 to 200 Å) average crystal size and 40-80 $m^2/g$ surface area, the product of low surface area and low pore volume by water from 0.3 to 0.65 $cm^3/g$ has the additional benefit of providing a smaller tablet size (i.e. less than 500 $mm^3$ for 500 mg compound) thereby improving tablet pill burden; a prevalent issues within the treatment of renal patients. Furthermore a higher density material is more suitable for the manufacture by wet granulation of compact tablets.

If product is dried to less than 85 wt % dry solid content storage problems may be observed because of water-desorption. If product is dried to less than 80 wt % dry solid content, milling may be problematic. If product is dried to more than 99 wt % the phosphate binding may be reduced. If product is too dry storage problems may also be observed because of water-adsorption. Therefore, in one embodiment, the product is dried such that it has 80 wt % to 99 wt % dry solid content, preferably 85 wt % to 99 wt %.

In one aspect the present invention provides a mixed metal compound comprising at least $Mg^{2+}$ and at least $Fe^{3+}$, wherein the molar ratio of $Mg^{2+}$ to $Fe^{3+}$ is 1.5:1 to 2.5.1, the mixed metal compound has an aluminium content of less than 10000 ppm, the average crystal size of the mixed metal compound is from 10 to 20 nm (100 to 200 Å), and the water pore volume of the mixed metal compound is from 0.3 to 0.65 $cm^3/g$ of mixed metal compound. Surprisingly we have found that this low pore volume compound has the advantage of good phosphate binding that is essentially unchanged upon storage over periods of up to years, making it viable as a pharmaceutically active material. It may be expected typically that significantly higher pore volumes would be required to attain such stability.

As used herein, the term 'water pore volume' refers to the pore volume as determined in accordance with Test Method 15.

For ease of reference, these and further aspects of the present invention are now discussed under appropriate section headings. However, the teachings under each section may be combined and are not necessarily limited to each particular section.

Preferred Aspects

As discussed herein the present invention provides a method of producing a mixed metal compound comprising at least $Mg^{2+}$ and at least $Fe^{3+}$
having an aluminium content of less than 10000 ppm,
having an average crystal size of less than 20 nm (200 Å)
comprising the steps of:
(a) combining a $Mg^{2+}$ salt and a $Fe^{3+}$ salt with $Na_2CO_3$ and NaOH to produce a slurry, wherein the pH of the slurry is maintained at from 9.5 to 11, and wherein the $Na_2CO_3$ is provided at an excess of 0 to 4.0 moles than is required to complete the reaction
(b) subjecting the slurry to mixing under conditions providing a power per unit volume of 0.03 to 1.6 $kW/m^3$
(c) separating the mixed metal compound from the slurry, to obtain a crude product having a dry solid content of at least 10 wt %
(d) drying the crude product either by
  (i) heating the crude product to a temperature of no greater than 150° C. and sufficient to provide a water evaporation rate of 0.05 to 1.5 kg water per hour per kg of dry product, or
  (ii) exposing the crude product to rapid drying at a water evaporation rate of 500 to 50000 kg water per hour per kg of dry product.

It will be understood by one skilled in the art that by "average crystal size" it is meant the crystal size as measured in accordance with Test Method 2.

In one preferred aspect, in step (a) a $Mg^{2+}$ salt and a $Fe^{3+}$ salt are combined with $Na_2CO_3$ and NaOH to produce a slurry, wherein the pH of the slurry is maintained at from 9.5 to 10.5. Preferably the pH of the slurry is maintained at from 9.5 to less than 10.1. Preferably the pH of the slurry is maintained at from 9.5 to less than 10. Preferably the pH of the slurry is maintained at from 9.5 to less than 9.8. Preferably the pH of the slurry is maintained at from 9.6 to 9.9. More preferably the pH of the slurry is maintained at approximately 9.8.

In one preferred aspect, in step (a) a $Mg^{2+}$ salt and a $Fe^{3+}$ salt are combined with $Na_2CO_3$ and NaOH to produce a slurry, wherein the $Na_2CO_3$ is provided at an excess from 2.0 to less than 4.0 moles, preferably at an excess from 2.7 to less than 4.0 moles, preferably at an excess from 2.7 to less than 3.2 moles, preferably at an excess from 2.7 to less than 3.0 moles. More preferably the $Na_2CO_3$ is maintained at an excess of approximately 2.7 moles.

In one preferred aspect, in step (a) a $Mg^{2+}$ salt and a $Fe^{3+}$ salt are combined with $Na_2CO_3$ and NaOH to produce a slurry, wherein the slurry is maintained to a temperature between 15 and 30° C.
  (i) wherein the pH of the slurry is maintained at from 9.5 to less than 9.8, and wherein the $Na_2CO_3$ is provided at an excess of greater than 1.0 to no greater than 5.0 moles than is required to complete the reaction, or
  (ii) wherein the pH of the slurry is maintained at from 9.5 to less than 10, and wherein the $Na_2CO_3$ is provided at an excess of greater than 1.0 to no greater than 4.0 moles than is required to complete the reaction; or
  (iii) wherein the pH of the slurry is maintained at from 9.5 to no greater than 10.1, and wherein the $Na_2CO_3$ is provided at an excess of greater than 1.0 to no greater than 2.7 moles than is required to complete the reaction; or
  (iv) wherein the pH of the slurry is maintained at from 9.5 to 10.5, and wherein the $Na_2CO_3$ is provided at an excess of from greater than 1.0 to no greater than 2.0 moles than is required to complete the reaction, or
  (v) wherein the pH of the slurry is maintained at from greater than 9.5 to no greater than 11, and wherein the $Na_2CO_3$ is provided at an excess of from 0.0 to no greater than 1.0 moles than is required to complete the reaction.

In one preferred aspect, in step (a) a $Mg^{2+}$ salt and a $Fe^{3+}$ salt are combined with $Na_2CO_3$ and NaOH to produce a slurry, wherein the slurry is maintained to a temperature between 15 and 30° C.
  i) wherein the pH of the slurry is maintained at from 9.5 to less than 9.8, and wherein the $Na_2CO_3$ is provided at an excess of greater than 2.0 to no greater than 4.0 moles than is required to complete the reaction; or
  (ii) wherein the pH of the slurry is maintained at from 9.5 to less than 10.3, and wherein the $Na_2CO_3$ is provided at an excess of greater than 2.0 to less than 4.0 moles than is required to complete the reaction; or
  (iii) wherein the pH of the slurry is maintained at from greater than 9.8 to no greater than 10.5, and wherein the $Na_2CO_3$ is provided at an excess of greater than 1.0 to less than 2.7 moles than is required to complete the reaction; or
  (iv) wherein the pH of the slurry is maintained at greater than 9.8 to less than 10.3, and wherein the $Na_2CO_3$ is provided at an excess of from 1 0 to less than 4.0 moles than is required to complete the reaction;

In one preferred aspect, in step (a) a $Mg^{2+}$ salt and a $Fe^{3+}$ salt are combined with $Na_2CO_3$ and NaOH to produce a slurry, wherein the slurry is maintained to a temperature from 30 to 60° C.
  (i) wherein the pH of the slurry is maintained at from greater than 9.5 to less than 11, and wherein the $Na_2CO_3$ is provided at an excess of greater than 0 to less than 2 moles than is required to complete the reaction; or
  (ii) wherein the pH of the slurry is maintained at from greater than 9.5 to less than 10.5, and wherein the $Na_2CO_3$ is provided at an excess of greater than 0 to less than 2.7 moles than is required to complete the reaction; or
  (iii) wherein the pH of the slurry is maintained at from greater than 9.5 to less than 10, and wherein the $Na_2CO_3$ is provided at an excess of greater than 0 to less than 4 moles than is required to complete the reaction.

In one preferred aspect, in step (a) a $Mg^{2+}$ salt and a $Fe^{3+}$ salt are combined with $Na_2CO_3$ and NaOH to produce a slurry, wherein the slurry is maintained to a temperature from 30 to 65° C.
  (i) wherein the pH of the slurry is maintained at from 9.5 to no greater than 10.5, and wherein the $Na_2CO_3$ is provided at an excess of greater than 0 to less than 2.7 moles than is required to complete the reaction; or
  (ii) wherein the pH of the slurry is maintained at from 9.5 to less than 10, and wherein the $Na_2CO_3$ is provided at an excess of greater than 0 to less than 4 moles than is required to complete the reaction.

In one preferred aspect, in step (b) the slurry is subjected to mixing under conditions providing a power per unit volume of 0.03 to 1.6 $kW/m^3$. In one preferred aspect, in step (b) the slurry is subjected to mixing under conditions providing a power per unit volume of 0.03 to 0.5 $kW/m^3$. In one preferred aspect, in step (b) the slurry is subjected to mixing under conditions providing a power per unit volume of 0.05 to 0.5 $kW/m^3$.

In one preferred aspect, in step (b) the slurry is controlled to a d50 particle size distribution (psd) of at least 40 μm. Preferably, the slurry is controlled to a d50 psd of greater than 40 μm. Preferably, the slurry is controlled to a d50 psd of at least 50 μm Preferably, the slurry is controlled to a d50 psd of at least 60 µm. More preferably, the slurry is controlled to a d50 psd of at least 70 µm. Preferably, the slurry is controlled to a d50 psd of greater than 70 µm. The d50 psd of the slurry is as measured in accordance with Test Method 9 herein.

As used herein, the term 'particle size distribution' refers to the d50 or average particle size distribution as determined in accordance with Test Method 24. D50 refers to the 50th percentile of that Test Method.

In one preferred aspect, in step (b) the slurry is controlled to a d50 psd of at least 40 µm after the addition of the reactants and after an initial hold time of 30 minutes to attain the optimum particle size distribution. Preferably, the slurry is controlled to a d50 psd of at least 50 µm after the addition of the reactants and after an initial hold time of 30 minutes. Preferably, the slurry is controlled to a d50 psd of at least 60 µm after the addition of the reactants and after an initial hold time of 30 minutes. More preferably, the slurry is controlled to a d50 psd of at least 70 µm after the addition of the reactants and after an initial hold time of 30 minutes.

In one preferred aspect, the hold time of slurry before isolation, such as before step (c), is less than 16 hours, preferably less than 12 hours. Preferably, the hold time is more than 30 minutes. In one preferred aspect, the hold time of slurry before isolation, such as before step (c), from 30 minutes to 16 hours. In one preferred aspect, the hold time of slurry before isolation, such as before step (c), from 30 minutes to 12 hours. If hold time increases to more than 16 hours the crystallite size may increase and/or particle size change.

In step (c) of the present method, the mixed metal compound is separated from the slurry, to obtain a crude product having a dry solid content of at least 10 wt %. Preferably the mixed metal compound is separated from the slurry, to obtain a crude product having a dry solid content of at least 15 wt %. More preferably the mixed metal compound is separated from the slurry, to obtain a crude product having a dry solid content of at least 20 wt %.

In step (d) of the present method the crude product is dried either by
(i) heating the crude product to a temperature of no greater than 150° C. and sufficient to provide a water evaporation rate of 0.05 to 1.5 kg water per hour per kg of dry product, or
(ii) exposing the crude product to rapid drying at a water evaporation rate of 500 to 50000 kg water per hour per kg of dry product.

It will be understood by one skilled in the art that reference to "heating the crude product to a temperature of no greater than X° C." refers to the heating the product such that the bulk temperature of the product is no greater than X° C. It will be understood that the temperature to which the product is exposed, for example a drum temperature in the case of drum drying, or the temperature of the shell of the product may be greater than X° C. when the bulk temperature of the product is X° C.

It will be understood by one skilled in the art that reference to a water evaporation rate at a rate of kg water per hour per kg of dry product, is to be measured in accordance with Test Method 18.

In one preferred aspect, step d(i) is followed, that is in step (d) the crude product is dried by heating the crude product to a temperature of no greater than 150° C. and sufficient to provide a water evaporation rate of 0.05 to 1.5 kg water per hour per kg of dry product.

In one preferred aspect, step d(ii) is followed, that is in step (d) the crude product is dried by exposing the crude product to flash drying or spray drying at a water evaporation rate of 500 to 50000 kg water per hour per kg of dry product.

Preferably when step d(i) is followed, the crude product is dried by heating the crude product to a temperature of no greater than 150° C. and sufficient to provide a water evaporation rate of 0.05 to 1 kg water per hour per kg of dry product, more preferably a water evaporation rate of 0.05 to 0.5 kg water per hour per kg of dry product, even more preferably a water evaporation rate of 0.09 to 0.5 kg water per hour per kg of dry product, most preferred a water evaporation rate of 0.09 to 0.38 kg water per hour per kg of dry product.

Preferably when step d(i) is followed, the crude product is dried by heating the crude product to a temperature of no greater than 150° C., such as no greater than 140° C., such as no greater than 130° C., such as no greater than 120° C., such as no greater than 110° C., such as no greater than 100° C., such as no greater than 90° C., such as from 60 to 150° C., such as from 70 to 150° C., such as from 60 to 140° C., such as from 70 to 140° C., such as from 60 to 130° C., such as from 70 to 130° C., such as from 60 to 120° C., such as from 70 to 120° C., such as from 60 to 110° C., such as from 70 to 110° C., such as from 60 to 100° C., such as from 70 to 100° C., such as from 60 to 90° C., such as from 70 to 90° C. Preferably when step d(i) is followed, the crude product is dried by heating the crude product to a temperature of from 35 to 150° C., such as from 35 to 140° C., such as from 35 to 130° C., such as from 35 to 120° C., such as from 35 to 110° C., such as from 35 to 100° C., such as from 35 to 90° C., such as from 35 to 80° C., such as from 35 to 70° C., such as from 35 to 60° C., such as from 35 to 50° C. Preferably when step d(i) is followed, the crude product is dried by heating the crude product to a temperature of from greater than 40 to 150° C., such as from greater than 40 to 140° C., such as from greater than 40 to 130° C., such as from greater than 40 to 120° C., such as from greater than 40 to 110° C., such as from greater than 40 to 100° C., such as from greater than 40 to 90° C., such as from greater than 40 to 80° C., such as from greater than 40 to 70° C., such as from greater than 40 to 60° C., such as from greater than 40 to 50° C. We have found that heating the crude product to a temperature of no greater than 90° C. and sufficient to provide a water evaporation rate of 0.05 to 1.5 kg water per hour per kg of dry product is particularly preferred. In this aspect, the average crystal size does not significantly increase during drying and the advantageous average crystal sizes described herein may be provided Preferably when step d(i) is followed, the crude product is dried by exposing the crude product to a temperature of no greater than 150° C., preferably exposing the crude product to a temperature of no greater than 140° C., preferably exposing the crude product to a temperature of no greater than 130° C., preferably exposing the crude product to a temperature of no greater than 120° C., preferably exposing the crude product to a temperature of no greater than 110° C., preferably exposing the crude product to a temperature of no greater than 100° C., preferably exposing the crude product to a temperature of no greater than 90° C., preferably exposing the crude product to a temperature of from 60 to 150° C., preferably exposing the crude product to a temperature of from 70 to 150° C., preferably exposing the crude product to a temperature of from 60 to 140° C., preferably exposing the crude product to a temperature of from 70 to 140° C., preferably exposing the crude product to a temperature of from 60 to 130° C., preferably exposing the crude product to a temperature of from 70 to 130° C., preferably exposing the crude product to a temperature of from 60 to 120° C., preferably exposing the crude product to a temperature of from 70 to 120° C., preferably exposing the crude product to a temperature of from 60 to 110° C., preferably exposing the crude product to a temperature of from 70 to 110° C., preferably exposing the crude product to a temperature of from 60 to 100° C., preferably exposing the crude product to a temperature of from 70 to 100° C., preferably exposing the crude product to a temperature of from 60 to 90° C., preferably from 70 to 90° C.

Preferably when step d(i) is followed, the crude product is dried to between 5-10 wt % moisture by exposing the crude product to a temperature from 35-90° C. and sufficient to provide a water evaporation rate of 0.05 to 0.5 kg water per hour per kg of dry product.

Preferably when step d(ii) is followed, the crude product is dried by exposing the crude product to flash drying or spray drying at a water evaporation rate of 900 to 40000 kg water per hour per kg of dry product.

Preferably when step d(ii) is followed, the crude product is dried by exposing the crude product to flash drying at a water evaporation rate from 1500 to 50000 or exposing the product to spray drying at a water evaporation rate from 500 to 1500 kg water per hour per kg of dry product. More preferably either from 20000 to 50000 by flash drying or from 900 to 1100 by spray drying.

Preferably when step d(ii) is followed, the crude product is dried by exposing the crude product to flash drying or spray drying at a water evaporation rate of 500 to 50000 kg water per hour per kg of dry product, a delta T from 0.30 to 0.80 and residence time of product in dryer of less than 5 minutes.

Before step (a) of the present method, after step (d) of the present method, between any one of steps (a), (b), (c) and (d) of the present method, one or more additional steps may be provided. These additional steps are encompassed by the present method. For example, in one preferred aspect, the crude product is washed prior to step (d).

An additional process step according to one aspect of the present invention comprises performing ion exchange on the mixed metal compound. This may be performed at any time during the process, such as when present in the slurry, as a crude product or a dried product. A preferred ion exchange is in respect of sulphate present in the mixed metal compound. Ion exchange performed in respect of sulphate present in the mixed metal compound is preferably performed by exchanging sulphate with carbonate, for example by contacting the mixed metal compound with a carbonate containing solution. Thus in this aspect, there is provided a method of producing a mixed metal compound comprising
at least $Mg^{2+}$ and at least $Fe^{3+}$
having an aluminium content of less than 10000 ppm,
having an average crystal size of less than 20 nm (200 Å)
comprising the steps of:
(a) combining a $Mg^{2+}$ salt and a $Fe^{3+}$ salt with $Na_2CO_3$ and NaOH to produce a slurry, wherein the pH of the slurry is maintained at from 9.5 to 11, and wherein the $Na_2CO_3$ is provided at an excess of 0 to 4.0 moles (such as an excess of 2.0 to 4.0 moles) than is required to complete the reaction
(b) subjecting the slurry to mixing under conditions providing a power per unit volume of 0.03 to 1.6 kW/m$^3$
(c) separating the mixed metal compound from the slurry, to obtain a crude product having a dry solid content of at least 10 wt %
(d) drying the crude product either by
  (i) heating the crude product to a temperature of no greater than 150° C. and sufficient to provide a water evaporation rate of 0.05 to 1.5 kg water per hour per kg of dry product, or
  (ii) exposing the crude product to rapid drying at a water evaporation rate of 500 to 50000 kg water per hour per kg of dry product,
(e) optionally contacting the slurry, the crude product or the mixed metal compound, with a carbonate containing solution to exchange sulphate present in the mixed metal compound with carbonate.

The separation of the product may be performed by any suitable method. For example the mixed metal compound may be separated from the slurry by centrifugation Different filtration methods may be utilized but a preferred aspect is obtained by a filtration method using centrifugation which combines filtration followed by washing and de-watering in one step. Another preferred aspect is obtained by a filtration method using a belt filter which combines filtration followed by washing and de-watering in one step After step (d) the product may be further treated. The present invention encompasses products obtained by virtue of further treatment. In one aspect the dried crude product is classified by sieving to a d50 average particle size of less than 300 µm, more preferably the dried crude product is milled to a d50 average particle size of less than 200 µm, more preferably the dried crude product is milled to a d50 average particle size of less than 100 µm, more preferably the dried crude product is milled to a d50 average particle size of 2 to 50 µm, more preferably the dried crude product is milled to a d50 average particle size of 2 to 30 µm.

Preferably, as measured by sieving, less than 10% by weight of particles are greater than 106 µm in diameter, more preferably less than 5%. Most preferably, no particles are greater than 106 µm in diameter as measured by sieving.

After step d(i) the product may be further treated. The present invention encompasses products obtained by virtue of further treatment. In one aspect the dried crude product is milled. More preferably the dried crude product is milled to a d50 average particle size of less than 10 µm, yet more preferably the dried crude product is milled to a d50 average particle size from 2-10 µm, most preferred the dried crude product is milled to a d50 average particle size from 2-7 µm, yet most preferred the dried crude product is milled to a d50 average particle size of approximately 5 µm.

Preferably, after step d(i) the dried crude product is milled to provide a surface area of 40-80 m$^2$/g, more preferably to a surface area of 40-70 m$^2$/g, even more preferably to a surface area of 45-65 m$^2$/g, most preferred to a surface area of 50-60 m$^2$/g.

Preferably, after step d(i) the dried crude product is milled to a d50 average particle size from 2-10 µm and a surface area of 40-80 m$^2$/g compound.

Preferably, after step d(ii) the dried product is not milled. Preferably, after step d(ii) the dried product has a d50 average particle size from 10-50 µm and a surface area of 80-145 m$^2$/g compound.

Preferably the dried crude product has a water content of less than 15 wt %, preferably the dried crude product has a water content of less than 10 wt %, preferably the dried crude product has a water content from 1-15 wt %, preferably the dried crude product has a water content from 5-15 wt %, preferably the dried crude product has a water content from 5-10 wt %, preferably the dried crude product has a water content from 8-15 wt %, preferably the dried crude product has a water content from 8-11 wt %, based on the total weight of the dried crude product.

Preferably the mixed metal compound has a dry solid content of at least 10 wt %. Preferably the mixed metal compound has a dry solid content of at least 15 wt %. More preferably the mixed metal compound has a dry solid content of at least 20 wt %.

When dried, the mixed metal compound has a dry solid content of at least 80 wt %. Preferably, the dried mixed metal compound has a dry solid content of more than 85 wt %. Preferably the dried mixed metal compound has a dry solid content of less than 99 wt %. More preferably the dried mixed metal compound has a dry solid content of less than 95 wt %. Most preferred the dried mixed metal compound has a dry solid content from 90 to 95 wt %.

As discussed herein, the compound has a average crystal size of less than 20 nm (200 Å). Preferably the compound has a average crystal size of from 100 to 200 Å. Preferably the compound has a average crystal size of from 155 to 200 Å. Preferably the compound has a average crystal size of from 110 to 195 Å. Preferably the compound has a average crystal size of from 110 to 185 Å. Preferably the compound has a average crystal size of from 115 to 165 Å. Preferably the compound has a average crystal size of from 120 to 185 Å. Preferably the compound has a average crystal size of from 130 to 185 Å. Preferably the compound has a average crystal size of from 140 to 185 Å. Preferably the compound has a average crystal size of from 150 to 185 Å. Preferably the compound has a average crystal size of from 150 to 175 Å. More preferably the compound has a average crystal size of from 155 to 175 Å. More preferably the compound has a average crystal size of from 155 to 165 Å.

In a further preferred embodiment there is provided for the production of a mixed metal compound having an average crystal size of less than 13 nm (130 Å) and a phosphate binding capacity of more than 0.65 mmol phosphate/g mixed metal compound.

In a further preferred embodiment there is provided for the production of a mixed metal compound having an average crystal size of less than 9 nm (90 Å) and a phosphate binding capacity of more than 0.70 mmol phosphate/g mixed metal compound.

In one preferred aspect the present invention provides a mixed metal comprising at least $Mg^{2+}$ and at least $Fe^{3+}$ wherein the molar ratio of $Mg^{2+}$ to $Fe^{3+}$ is 2.1:1 to 1.7:1 having an aluminium content of less than 30 ppm, having a average crystal size from 110-195 Å, having an interlayer sulphate from 2.1 to 5 wt % (such as from 2.1 to 3.2 wt %) comprising the steps of (a) combining a $Mg^{2+}$ salt and a $Fe^{3+}$ salt with $Na_2CO_3$ and NaOH to produce a slurry, wherein the pH of the slurry is maintained at from 9.6 to less than 10, and wherein the $Na_2CO_3$ is provided at an excess of 2.7 moles than is required to complete the reaction (b) subjecting the slurry to mixing under conditions providing a power per unit volume of 0.05 to 0.05 kW/m$^3$ (b1) controlling the slurry to a temperature from 20 to 25° C.

(b2) optionally controlling the slurry to a d50 psd of at least 40 μm (preferably controlling the slurry to a d50 psd of at least 40 μm)

(c) separating the mixed metal compound from the slurry, to obtain a crude product having a dry solid content of at least 10 wt %

(d) (i) drying the crude product to 5-10 wt % moisture by exposing the crude product to a temperature from 40-90° C. and sufficient to provide a water evaporation rate of 0.05 to 0.5 kg water per hour per kg of dry product.

The compound prepared by the present method may be any mixed metal compound comprising $Mg^{2+}$ and at least $Fe^{3+}$. In one preferred aspect, the compound is a compound having a hydrotalcite structure. Preferably the compound is of the formula

wherein $M^{II}$ is one or more bivalent metals and is at least $Mg^{2+}$;

$M^{III}$ is one or more trivalent metals and is at least $Fe^{3+}$;
$A^{n-}$ is one or more n-valent anions and is at least $CO_3^{2-}$;
$1.0 < x/\Sigma yn < 1.2$, $0 < x \leq 0.67$, $0 < y \leq 1$ and $0 < m \leq 10$.

The method by which the molecular formula of a mixed metal compound may be determined will be well known to one skilled in the art. It will be understood that the molecular formula may determined from the analysis of $M^{II}/M^{III}$ ratio (Test Method 1), $SO_4$ analysis (Test Method 5), $CO_3$ analysis (Test Method 6) and $H_2O$ analysis (Test Method 12).

Preferably, $0 < x \leq 0.4$, $0 < y \leq 1$ and $0 < m \leq 10$.
Preferably $1.05 < x/\Sigma yn < 1.2$, preferably $1.05 < x/\Sigma yn < 1.15$. In one preferred aspect $x/\Sigma yn = 1$.

In one preferred aspect $0.1 < x$, such as $0.2 < x$, $0.3 < x$, $0.4 < x$, or $0.5 < x$. In one preferred aspect $0 < x \leq 0.5$. It will be understood that $x + [M^{III}]/([M^{II}] + [M^{III}])$ where $[M^{II}]$ is the number of moles of $M^{II}$ per mole of compound of formula I and $[M^{III}]$ is the number of moles of $M^{III}$ per mole of compound of formula I.

In one preferred aspect $0 < y \leq 1$. Preferably $0 < y \leq 0.8$. Preferably $0 < y \leq 0.6$. Preferably $0 < y \leq 0.4$. Preferably $0.05 < y \leq 0.3$. Preferably $0.05 < y \leq 0.2$. Preferably $0.1 < y \leq 0.2$. Preferably $0.15 < y \leq 0.2$.

In one preferred aspect $0 \leq m \leq 10$. Preferably $0 \leq m \leq 8$. Preferably $0 \leq m \leq 6$. Preferably $0 \leq m \leq 4$. Preferably $0 \leq m \leq 2$. Preferably $0 \leq m \leq 1$. Preferably $0 \leq m \leq 0.7$. Preferably $0 \leq m \leq 0.6$. Preferably $0.15 \leq m \leq 0.6$. Preferably $0 \leq m \leq 0.5$. Preferably $0 \leq m \leq 0.3$. Preferably $0 \leq m \leq 0.15$. Preferably $0.15 \leq m \leq 0.5$. The number of water molecules m can include the amount of water that may be absorbed on the surface of the crystallites as well as interlayer water. The number of water molecules is estimated to be related to x according to: $m = 0.81 - x$.

It will be appreciated that each of the preferred values of x, y, z and m may be combined.

In one preferred aspect the compound has an aluminium content of less than 5000 ppm, more preferably less than 1000 ppm, most preferred 100 ppm, most preferably 30 ppm.

In one preferred aspect the total sulphate content of the compound is from 1.8 to 5 wt %. By total sulphate content it is meant content of sulphate that is present in the compound. This may be determined by well known methods and in particular determined in accordance with Test Method 1. Preferably the total sulphate is from 2 to 5 wt % preferably from 2 to 3.7 wt %, preferably from 2 to 5 wt %, preferably from 2 to less than 5 wt %, preferably from 2.1 to 5 wt % preferably from 2.1 to less than 5 wt %, preferably from 2.2 to 5 wt %, preferably from 2.2 to less than 5 wt %, preferably from 2.3-5 wt %, preferably from 2.3 to less than 5 wt %.

In one preferred aspect the total sulphate content of the compound is from 1.8 to 4.2 wt %. By total sulphate content it is meant content of sulphate that is present in the compound. This may be determined by well known methods and in particular determined in accordance with Test Method 1. Preferably the total sulphate is from 2 to 4.2 wt % preferably from 2 to 3.7 wt %, preferably from 2 to 3.2 wt %, preferably from 2 to less than 3.2 wt %, preferably from 2.1 to 3.2 wt % preferably from 2.1 to less than 3.2 wt %, preferably from 2.2 to 3.2 wt %, preferably from 2.2 to less than 3.2 wt %, preferably from 2.3-3.2 wt %, preferably from 2.3 to less than 3.2 wt %.

The compound will also contain an amount of sulphate that is bound within the compound. This content of sulphate, the interlayer sulphate, may not be removed by a washing process with water. As used herein, amounts of interlayer sulphate are the amount of sulphate as determined in accordance with Test Method 5. In a preferred aspect the interlayer sulphate content of the compound is from 1.8 to 5 wt %, preferably from 1.8 to 3.2 wt %, preferably from 2 to 5 wt %, preferably from 2 to less than 5 wt %, preferably from 2 to 3.2 wt %, preferably from 2 to 3.1 wt %, preferably from 2 to 3.0 wt %. Preferably the interlayer sulphate content of the compound is from 2.1 to 5 wt %, preferably from 2.1 to 3.2 wt %, preferably from 2.1 to less than 3.2 wt %. More preferably the interlayer sulphate content of the compound is from 2.2 to 5 wt %, preferably from 22 to 3.2 wt %, preferably from 2.2 to less than 3.2 wt %. Yet more preferably the interlayer sulphate content of the compound is from 2.3 to 5 wt %, preferably from 2.3 to 3.2 wt %, preferably from 2.3 to less than 3.2 wt %. Most preferably the interlayer sulphate content of the compound is from 2.5 to 5 wt %, preferably from 2.5 to 3.2 wt %, preferably from 2.5 to less than 3.2 wt %. Yet most preferred the interlayer sulphate content of the compound is from 2.5 to 3.0 wt %.

As discussed herein, the present invention provides novel compounds. As discussed herein, the present invention provides a mixed metal compound comprising at least $Mg^{2+}$ and at least $Fe^{3+}$,
wherein
the molar ratio of $Mg^{2+}$ to $Fe^{3+}$ is 2.5:1 to 1.5:1,
the mixed metal compound has an aluminium content of less than 10000 ppm,
the average crystal size of the mixed metal compound is from 10 to 20 nm (100 to 200 Å), and the d50 average particle site of the mixed metal compound is less than 300 μm. Preferably the d50 average particle size of the mixed metal compound is less than 200 μm.

As discussed herein, the present invention provides a mixed metal compound comprising at least $Mg^{2+}$ and at least $Fe^{3+}$,
wherein
the molar ratio of $Mg^{2+}$ to $Fe^{3+}$ is 2.5:1 to 1.5:1,
the mixed metal compound has an aluminium content of less than 10000 ppm,
the average crystal size of the mixed metal compound is from 10 to 20 nm (100 to 200 Å), and the water pore volume of the mixed metal compound is from 025 to 0.7 cm$^3$/g of mixed metal compound. Preferably the water pore volume of the mixed metal compound is from 0.3 to 0.65 cm$^3$/g of mixed metal compound. Preferably the water pore volume of the mixed metal compound is from 0.35 to 0.65 cm$^3$/g of mixed metal compound. Preferably the water pore volume of the mixed metal compound is from 0.3 to 0.6 cm$^3$/g of mixed metal compound.

In further preferred embodiment of this aspect the nitrogen pore volume of the mixed metal compound is from 028 to 0.56 cm$^3$/g. As used herein, the term 'nitrogen pore volume' refers to the pore volume as determined in accordance with Test Method 14. When the nitrogen pore volume of the mixed metal compound is from 0.28 to 0.56 cm$^3$/g it has been found that the close correlation to the water pore volume is such that the water pore volume need not be determined. Thus in a further aspect the present invention provides a mixed metal compound comprising at least $Mg^{2+}$ and at least $Fe^{3+}$,
wherein
the molar ratio of $Mg^{2+}$ to $Fe^{3+}$ is 2.5:1 to 1.5:1,
the mixed metal compound has an aluminium content of less than 10000 ppm,
the average crystal size of the mixed metal compound is from 10 to 20 nm (100 to 200 Å), and the nitrogen pore volume of the mixed metal compound is from 0.28 to 0.56 cm$^3$/g.

As discussed herein, the present invention provides a mixed metal compound comprising
at least $Mg^{2+}$ and at least $Fe^{3+}$,
wherein
the molar ratio of $Mg^{2+}$ to $Fe^{3+}$ is 2.51 to 1.5:1,
the mixed metal compound has an aluminium content of less than 10000 ppm,
the average crystal size of the mixed metal compound is from 10 to 20 nm (100 to 200 Å),
and the interlayer sulphate content of the compound is from 1.8 to 5 wt % (such as from 1.8 to 3.2 wt %). Preferably the average crystal size of the mixed metal compound is from 12 to 20 nm (120 to 200 Å).

As discussed herein, the present invention provides a mixed metal compound comprising at least $Mg^{2+}$ and at least $Fe^{3+}$,
wherein
the molar ratio of $Mg^{2+}$ to $Fe^{3+}$ is 2.5:1 to 1.5:1,
the mixed metal compound has an aluminium content of less than 10000 ppm,
the average crystal size of the mixed metal compound is less than 20 nm (200 Å),
and the interlayer sulphate content of the compound is from 2.1 to 5 wt % (such as from 1.8 to 3.2 wt %). Preferably the average crystal size of the mixed metal compound is from 10 to 20 nm (100 to 200 Å).

As discussed herein, the present invention provides a mixed metal compound comprising at least $Mg^{2+}$ and at least $Fe^{3+}$,
wherein
the molar ratio of $Mg^{2+}$ to $Fe^{3+}$ is 2.5:1 to 1.5:1,
the mixed metal compound has an aluminium content of less than 10000 ppm,
the average crystal size of the mixed metal compound is less than 20 nm (200 Å), and the surface area is from 80 to 145 m$^2$ per gram of compound. Preferably the compound has a d50 average particle size of from 10 to 350 μm (and preferably wherein the compound has not been subject to milling). Preferably the compound has a d50 average particle size of from 10 to 300 μm. Preferably the compound has a d50 average particle size of from 10 to 210 μm. Preferably the compound has a d50 average particle size of from 10 to 100 μm. Preferably the compound has a d50 average particle size of from 10 to 50 μm. Preferably the compound has a d50 average particle size of from 10 to 35 μm Preferably the compound releases magnesium in an amount is less than 0.15 mmol magnesium/g compound. The magnesium release is determined in accordance with Test Method 3

As discussed herein, the present invention provides a mixed metal compound comprising at least $Mg^{2+}$ and at least $Fe^{3+}$,
wherein
the molar ratio of $Mg^{2+}$ to $Fe^{3+}$ is 2.5:1 to 1.5:1,
the mixed metal compound has an aluminium content of less than 10000 ppm,
the average crystal size of the mixed metal compound is from 10 to 20 nm (100 to 200 Å), the surface area is from 40 to 80 m$^2$ per gram of compound.

Preferably the d50 average particle size of the mixed metal compound is less than 100 μm. Preferably the d50 average particle size of the mixed metal compound is less than 50 μm. Preferably the d50 average particle size of the mixed metal compound is less than 20 μm. Preferably the d50 average particle size of the mixed metal compound is less than 10 μm. Preferably the d50 average particle size of the mixed metal compound is approximately 5 μm. Preferably the water pore volume of the mixed metal compound is from 0.25 to 0.7 cm$^3$/g of mixed metal compound, preferably the water pore volume is from 0.3 to 0.65 cm$^3$/g of mixed metal compound, preferably the water pore volume is from 0.3 to 0.6 cm$^3$/g of mixed metal compound. Preferably the nitrogen pore volume of the mixed metal compound is from 0.28 to 0.56 cm$^3$/g of mixed metal compound.

In each of the aspects of the invention in which a mixed metal compound is provided, preferably
(1) the interlayer sulphate content of the compound is from 2.2 to 5 wt % (such as from 1.8 to 3.2 wt %), and/or
(2) the compound is of the formula $$M^{II}_{1-x}M^{III}_{x}(OH)_2A^{n-}_{y}.m.H_2O$$

wherein $M^{II}$ is one or more bivalent metals and is at least $Mg^{2+}$,
$M^{III}$ is one or more trivalent metals and is at least $Fe^{3+}$,
$A^{n-}$ is one or more n-valent anions and is at least $CO_3^{2-}$,
x/Σyn is from 1 to 1.2 (preferably x/Σyn is from 1.05 to 1.15, preferably x/Σyn is 1)
0<x≤0.4
0<y≤1 and
0<m≤10, and/or
(3) the compound has an aluminium content of less than 100 ppm, preferably an aluminium content of less than 30 ppm
(4) the interlayer sulphate content of the compound is from 1.8 to 5 wt % (such as from 1.8 to 3.2 wt %), and/or
(5) the compound has a d50 average particle size of less than 100 μm, preferably the compound has a d50 average particle size of 5 to 50 μm, preferably the compound has a d50 average particle size of approximately 5 μm and/or
(6) the water pore volume of the mixed metal compound is from 0.3 to 0.65 cm$^3$/g of mixed metal compound and/or
(7) the compound has a dry solid content of at least 20 wt %.

The compound may have any degree of porosity, subject to any range specified herein. In a preferred aspect the water pore volume of the mixed metal compound is from 0.25 to 0.7 cm$^3$/g of mixed metal compound. In a preferred aspect the water pore volume of the mixed metal compound is from 0.3 to 0.65 cm$^3$/g of mixed metal compound.

Preferably the mixed metal compound comprises at least some material which is a Layered Double Hydroxide (LDH). More preferably, the mixed metal compound of formula (I) is a layered double hydroxide. As used herein, the term "Layered Double Hydroxide" is used to designate synthetic or natural lamellar hydroxides with two different kinds of metallic cations in the main layers and interlayer domains containing anionic species. This wide family of compounds is sometimes also referred to as anionic clays, by comparison with the more usual cationic clays whose interlamellar domains contain cationic species. LDHs have also been reported as hydrotalcite-like compounds by reference to one of the polytypes of the corresponding [Mg—Al] based mineral.

A particularly preferred mixed metal compound contains at least one of carbonate ions, and hydroxyl ions.

A particularly preferred compound contains as $M^{II}$ and $M^{III}$, magnesium and iron (III) respectively.

Process

The mixed metal compound or compounds may be suitably made by co-precipitation from a solution, followed by centrifugation or filtration, then drying, milling and/or sieving. The mixed metal compound may then be rewetted as part of the wet-granulation process and the resulting granules dried in a fluid-bed dryer. The degree of drying in the fluid-bed is used to establish the desired water content of the final tablet.

Two methods of coprecipitation may be used, namely one at low supersaturation whereby the pH of the reaction solution is maintained constant by controlling the addition of a second solution of an alkali, or alternatively precipitation at high supersaturation whereby the pH of the reaction solution is continuously changed by addition of the mixed metal solution to an alkali solution already present in the reactor vessel. The precipitation method whereby the pH is kept constant is preferred as this avoids the formation of single metal compounds such as $M(OH)_2$ and/or $M(OH)_3$ phases instead of mixed metal compound.

Other precipitation methods of the mixed metal compound may also be possible if the crystallite size is controlled to less than 200 Å. For example, a precipitation method involving separate nucleation and aging steps, an urea hydrolysis method, an induced hydrolysis method, a salt-oxide method, a sol-gel method, an electrosynthesis method, an in situ oxidation of the divalent metal ion to a trivalent metal ion, a so-called "Chimie Douce" method or a method wherein the mixed metal compound may be formed by heating an intimate mixture of finely divided single metal salts at a temperature whereby solid-solid reaction can occur, leading to a mixed metal compound formation.

Post synthesis methods that tend to promote ageing are less preferred but may be used if crystallite size is controlled to less than 200 Å. Examples of possible post synthesis heat-treatment steps include hydrothermal, microwave and ultrasound.

A variety of methods can be used to separate the mixed metal compound from the reaction slurry. Different washing, drying and milling methods are also possible where crystallite size is less than 200 Å.

The substances of the invention prepared by treatment of a suitable starting material as hereinbefore described may be prepared by providing a first solution of a water soluble compound of metal $M^{II}$ and a water soluble compound of metal $M^{III}$, the anions being chosen so as not to result in precipitation from the first solution (A). A second solution (B) is also provided, of a water soluble hydroxide (e.g. NaOH) and a water soluble salt of anion $A^{n-}$ (the cation being chosen so as not to precipitate with the hydroxide or the anion with the metal from the hydroxide). The two solutions are then combined and the mixed metal compound starting material is formed by co-precipitation. For example, Solution A is made up by dissolving magnesium sulphate and ferric sulphate in purified water. Solution B is made up by dissolving sodium carbonate and sodium hydroxide in purified water. A heel of purified water is added to a reactor, the solutions A and B are fed in a ratio controlled manner. After the product forms in the reactor it may comprise solid crystalline material, usually also with the presence of some solid amorphous material. Preferably, at least some of the material so formed is of a layered double hydroxide and/or of a hydrotalcite structure, usually also with some amorphous and/or poorly crystalline material, preferably after co-precipitation, the material is then filtered or centrifuged, washed then dried by heating. The drying is carried out either by (i) exposing the crude product to a temperature of no greater than 150° C. and sufficient to provide a water evaporation rate of 0.05 to 1.5 kg water per hour per kg of dry product, or (ii) exposing the crude product to flash drying or spray drying at a water evaporation rate of 500 to 50000 kg water per hour per kg of dry product, for example by oven drying, spray drying or fluid bed drying.

Optionally, the dry material may be first classified, to remove oversize particles by milling and/or sieving and/or any other suitable technique, for example to restrict the material to be treated to particles which are substantially no greater than 300 μm in diameter.

Reaction

A wide number of options are available for carrying out the reaction. These may be controlled in order to carry out the reaction in the manner desired. For example, the reactant equipment type, reactant stream composition, temperature and pH, mode of reactant addition, agitation system, and hold time may all be specified in order to produce a desired reaction.

Various reactor types are common in the pharmaceutical industry, these include Batch and Continuous reactors.

The material structure and crystallite size can be significantly determined at the reaction stage by close control of the reactant solution concentration, the reaction temperature, the time that the reaction mass is held following precipitation and the mode of reactant addition. Furthermore, in order to achieve the preferred material structure with small crystallite size, a high solution concentration (at end of reaction period of 4.8-5.4 wt %), low reaction temperature (15-25° C.) and short hold time (typically <12 hours) are preferred.

To prepare the mixed metal compounds to a preferred Mg:Fe molar ratio, for example from 1.5:1 to 2.5:1 then precise control of pH during the precipitation process is desirable. Precise pH control is typically achieved by frequent calibration of pH electrodes and monitoring and adjustment of the pH throughout the precipitation process. The pH of the reaction may be controlled by varying the relative rate of addition of Solution A to Solution B added to the reactor. We have found that the variation of Solution B only is preferred since this maintains the precipitate concentration in the reaction mix at a constant level. The variation in Solution B flow rate can be carried out manually or using a suitable control algorithm We have found an optimal reactant composition, whereby opposing requirements of maintaining a relatively low reaction temperature, but achieving reasonable filtration rate and good pH control, are met.

For example, the preferred $M^{2+}:M^{3+}$ molar ratio between 1.5.1 to 2.5:1 of the mixed metal compound can be achieved by maintaining the reactant streams in solution even at relatively low temperatures, thereby limiting the reaction temperature. The reaction temperature can be important in determining the extent of crystallite growth and hence the phosphate binding activity.

The preferred method allows good filtration rates to be achieved, this again can be important in limiting the reaction mass storage time which in term is known to help determine the extent of crystallite growth, and hence the phosphate binding activity.

Further, the preferred reaction conditions and recipe helps to maintain good pH control. Good pH control is required in order to achieve the target pH.

The mode of reactant stream addition can be important in defining the reaction product quality. Different combinations of addition mode are possible and may include the addition of one reactant stream into an excess of the other reactant (either reactant could be selected as the added stream).

We have found that simultaneous addition of a high pH reactant stream containing carbonate and hydroxide ions, and a low pH reactant stream containing metal and sulphate ions into a heel provides more accurate pH control of the reaction slurry. Therefore, in a preferred embodiment, the reaction is carried out by simultaneous addition (co-precipitation) of a reactant stream containing carbonate and hydroxide ions, and a reactant stream containing metal and sulphate ions.

Similarly, the product can be removed on a continuous basis as the reactants streams are added, or at the end of a defined period.

Good filtration characteristics are achieved by targeting a relatively large particle size such as of at least 40 μm by controlling the power per unit volume from 0.03 to 1.6 $kW/m^3$. We have identified that power per unit volume of 0.05 to 0.5 $kW/m^3$ using impeller(s) configured for axial flow agitation, helps to produce a slurry with further improved filtration characteristics (such as lower filtration and washing time, and high final solids content in cake).

Therefore, in a preferred embodiment, agitation is used to subject the slurry to mixing under conditions providing a power per unit volume of 0.03 to 1.6 $kW/m^3$ provided by static mixers, impeller agitators, pump, jet mixer or dynamic in line mixer. Therefore, in a further preferred embodiment, axial flow agitation is used to subject the slurry to mixing under conditions providing a power per unit volume of 0.03 to 1.6 $kW/m^3$ provided by an impeller agitator. More preferably a power per unit volume of 0.05 to 0.5 $kW/m^3$ delivered by impeller agitation. This provides reaction slurry with the preferred filtration characteristics.

Therefore, in a separate embodiment, the reaction is agitated using means other than a conventional impeller agitator An optimum hold time has been identified as from 30 minutes to 12 hours. For hold times of more than 16 hours, filtration becomes difficult due to a reduction in particle size during use of agitation in hold time and ageing occurs.

Filtration

A wide number of options are available for carrying out the product isolation and washing steps, however the filtration equipment type and operating process parameters should be carefully defined and controlled.

For example, in order to limit the overall reaction slurry hold time (and hence crystallite growth), it is beneficial to minimise the time for cake isolation and wash time A high cake solids content is also preferable as this reduces the drying time and hence the propensity for crystallite growth during the drying step.

Various filter types are used in the pharmaceutical industry, these include: Neutsche filters, Filter dryers, Filtering centrifuges, Belt filters, Plate and frame filters.

When isolating the unaged mixed metal compound, the overall filtration rate can be extremely low due to the relative difficulty of isolating and washing these unaged clay-type mixed metal compounds making this economically unattractive if not controlled to the preferred conditions. The unaged material of crystallite size of less than 200 Å, has the tendency to result in 'blinding' of the filtration media and/or the clay-type properties have a tendency to form a more impermeable cake.

In one preferred embodiment we have produced high filtration rate using a belt filter Drying A wide number of options are available for carrying out the drying operation, these should be defined and controlled in order to carry out the drying step in the best manner.

For example, the dryer type, mode of drying, and rate of drying should be specified and controlled such that the crude product is dried either by (i) exposing the crude product to a temperature of no greater than 150° C. and sufficient to provide a water evaporation rate of 0.05 to 1.5 kg water per hour per kg of dry product, or (ii) exposing the crude product to flash drying or spray drying at a water evaporation rate of 500 to 50000 kg water per hour per kg of dry product. The rate of drying is affected by factors including the mode of drying, heated surface/heating medium temperature, degree of agitation, vacuum level (if any) etc. The product temperature must be limited to no greater than 150° C. to prevent damage to the drug substance.

Various dryer types are common in the pharmaceutical industry, these include long residence time dryers (characterised as typically up to 20 h residence time) such as Spherical, Conical, Double cone, Tray dryer (vacuum, ambient pressure), and short residence time dryers (characterised as typically up to several minutes residence time) include; Spray, Spin flash, Etc.

We have found that of the various batch dryer designs an agitated spherical dryer offers a large heated surface area to the product. Therefore a higher product rate per unit area from 1 to 2.1 kg product/(m²·hr) and thus high heat transfer and drying rates are possible. Since ageing (crystallite growth) can occur during drying, it is important to minimise the drying time/maximise drying rate. In order to prevent decomposition of the drug substance, where surface heating is used the drying surface temperature is typically limited to 150° C. for batch drying and preferably 90° C. or less to avoid average crystal size growth to above 200 Å Partial evacuation of the dryer depresses the boiling point of water in the drying mass, thereby limiting crystal growth, this depression also serves to maximise the drying rate. The drying rate is manipulated by maximising the dryer vacuum and for increasing the shell temperature up to 120° C. during an initial drying phase, to remove water at the highest possible rate, and then reducing the rate by reducing the shell temperature to less than 90° C., in order to accurately target a defined moisture end point whilst maintaining a crystallite size less than 200 Å. The moisture end point can be inferred by monitoring the evaporation mass, or measured directly, by analysis of the dried contents, or other suitable methods.

Conical dryers (e.g. Nautamixer type) offer similar benefits to the spherical dryer.

Vacuum tray dryers were found to produce an acceptable product quality, however this type of dryer can require manual intervention (e.g. redistribution of solids) for uniform drying, and has limited throughput.

The long residence time batch dryers described (spherical, conical, vacuum) all have relatively low drying rates (expressed in normalised terms as kg evaporation per kg product per hour) when compared to the short residence time drying methods. We have found that the temperature of the drug substance during drying and the drying rate can significantly influence the crystallite size and morphology of the drug substance.

For example, long residence time batch drying tends to produce a relatively large average crystal size and relatively low pore volume and surface area, whereas short residence methods such as spray drying and spin flash drying have been found to produce relatively smaller crystals with relatively large pore volume and surface area. Material produced using short residence time drying can show an enhanced phosphate binding performance; this may be due to the different crystallite and morphological properties. Spray dried material has the additional advantage of granulation for just dry blending (e.g. for tablet manufacture) and may be carried out without prior milling of the drug substance.

Long residence drying time methods are typically defined as having a residence time equal to or greater than 3 hours. Examples of these include: tray drying, kettle drying, pan drying, rotary (shell) drying, rotary (internal) drying, double cone drying.

We have found average evaporation rates of between 9 and 29 kg water/(h·m²) are achievable using an agitated vacuum spherical dryer. Stated on an alternative basis this is equivalent to an evaporation rate of approximately 0.05 to 0.5 kg water per hour per kg of dry product. The product crystallite size produced at this range of evaporation rates is typically between 100-200 Angstroms. For a dried product of consistent quality the dryer must be fed with a wet cake (typically >20 wt % solids).

Each of the above dryers is operated on a batch basis.

Short residence drying time method examples typically have much lower residence times. These differ depending upon technology types and are defined as: spin flash drying, typical residence time of 5 to 500 seconds/spray drying, typical residence time up to 60 seconds.

Typical evaporation rates are defined as spin flash 70-300 kg water/(h·m³) vessel volume, spray 5-25 kg water/(h·m³) vessel volume. Evaporation rates for spin flash and spray dryers are also calculated as 500 to 50000 kg water/(h kg drug). The product crystallite size produced at this range of evaporation rates is typically less than 140 Angstroms. The spin flash dryer may be fed with wet cake (typically >20 wt % solids), whereas the spray dryer must be fed with a free flowing slurry at a lower concentration (typically to 10 wt % solids)

The above short residence time dryers may all be operated on a continuous basis.

Various 'medium' residence time technologies can be used which predominantly rely on the use conveyors and are operated continuously. These may be less preferred if problems occur in terms of ensuring a consistent quality of product (variable moisture content) and cleanliness for pharmaceutical production. Examples of medium residence time technologies are listed as: Rotary shelf, Trough Vibrating, Turbo type.

Uses

Preferably the compound is used in the manufacture of a medicament for the prophylaxis or treatment of hyperphosphataemia.

In a further aspect the present invention provides use of a compound of the present invention or obtained/obtainable in accordance with the present invention in the manufacture of a medicament for the prophylaxis or treatment of any one of hyperphosphataemia, renal insufficiency, hypoparathyroidism, pseudohypoparathyroidism, acute untreated acromegaly, chronic kidney disease and over medication of phosphate salts.

Examples of one or more of the symptoms which may indicate risk for the presence of CKD a creatine concentration of above 1.6 mg/dL, a blood phosphate level of above 4.5 mg/dL, any detectable blood in urine, urine protein concentration above 100 mg/dL, a urine albumin concentration above about 100 mg/dL, a glomerular filtration rate (GFR) of below 90 mL/min/1.73 m² or a parathyroid hormone concentration in the blood above 150 pg/mL. The symptoms are also defined by the National Kidney Foundation-Sidney Disease Outcomes Quality Initiative "NKF-K/DOQI" or "K/DOQI,".

In one preferred aspect the chronic kidney disease (CKD) treated in accordance with the presence invention is CKD having stage one to five.

The medicament may be used on animals, preferably humans.

Pharmaceutical Compositions

A pharmaceutically acceptable carrier may be any material with which the substance of the invention is formulated to facilitate its administration. A carrier may be a solid or a liquid, including a material which is normally gaseous but which has been compressed to form a liquid, and any of the carriers normally used in formulating pharmaceutical compositions may be used. Preferably, compositions according to the invention contain 0.5% to 95% by weight of active ingredient. The term pharmaceutically acceptable carrier encompasses diluents, excipients or adjuvants.

When the substances of the invention are part of a pharmaceutical composition, they can be formulated in any suitable pharmaceutical composition form e.g. powders, granules, granulates, sachets, capsules, stick packs, battles, tablets but especially in a form suitable for oral administration for example in solid unit dose form such as tablets, capsules, or in liquid form such as liquid suspensions, especially aqueous suspensions or semi-solid formulations, e.g. gels, chewy bar, dispersing dosage, chewable dosage form or edible sachet Direct addition to food may also be possible.

Dosage forms adapted for extra-corporeal or even intravenous administration are also possible. Suitable formulations can be produced by known methods using conventional solid carriers such as, for example, lactose, starch or talcum or liquid carriers such as, for example, water, fatty oils or liquid paraffins. Other carriers which may be used include materials derived from animal or vegetable proteins, such as the gelatins, dextrins and soy, wheat and psyllium seed proteins; gums such as acacia, guar, agar, and xanthan, polysaccharides; alginates; carboxymethylcelluloses, carrageenans; dextrans; pectins; synthetic polymers such as polyvinylpyrrolidone, polypeptide/protein or polysaccharide complexes such as gelatin-acacia complexes, sugars such as mannitol, dextrose, galactose and trehalose, cyclic sugars such as cyclodextrin; inorganic salts such as sodium phosphate, sodium chloride and aluminium silicates; and amino acids having from 2 to 12 carbon atoms such as a glycine, L-alanine, L-aspartic acid, L-glutamic acid, L-hydroxyproline, L-iso-leucine, L-leucine and L-phenylalanine.

Auxiliary components such as tablet disintegrants, solubilisers, preservatives, antioxidants, surfactants, viscosity enhancers, colouring agents, flavouring agents, pH modifiers, sweeteners or taste-masking agents may also be incorporated into the composition. Suitable colouring agents include red, black and yellow iron oxides and FD & C dyes such as FD & C blue No. 2 and FD & C red No 40 available from Ellis & Everard Suitable flavouring agents include mint, raspberry, liquorice, orange, lemon, grapefruit, caramel, vanilla, cherry and grape flavours and combinations of these. Suitable pH modifiers include sodium hydrogencarbonate, citric acid, tartaric acid, hydrochloric acid and maleic acid. Suitable sweeteners include aspartame, acesulfame K and thaurnatin. Suitable taste-masking agents include sodium hydrogencarbonate, ion-exchange resins, cyclodextrin inclusion compounds, adsorbates or microencapsulated actives.

For treatment of and prophylaxis of hyperphosphataemia, preferably amounts of from 0.1 to 500, more preferably from 1 to 200, mg/kg body weight of substance of the invention as active compound are administered daily to obtain the desired results. Nevertheless, it may be necessary from time to time to depart from the amounts mentioned above, depending on the body weight of the patient, the method of application, the animal species of the patient and its individual reaction to the drug or the kind of formulation or the time or interval in which the drug is applied. In special cases, it may be sufficient to use less than the minimum amount given above, whilst in other cases the maximum dose may have to be exceeded. For a larger dose, it may be advisable to divide the dose into several smaller single doses. Ultimately, the dose will depend upon the discretion of the attendant physician. Administration soon before meals, e.g. within one hour before a meal or taken with food will usually be preferred A typical single solid unit dose for human adult administration may comprise from 1 mg to 1 g, preferably from 10 mg to 800 mg of substance of the invention.

A solid unit dose form may also comprise a release rate controlling additive. For example, the substance of the invention may be held within a hydrophobic polymer matrix so that it is gradually leached out of the matrix upon contact with body fluids. Alternatively, the substance of the invention may be held within a hydrophilic matrix which gradually or rapidly dissolves in the presence of body fluid. The tablet may comprise two or more layers having different release properties. The layers may be hydrophilic, hydrophobic or a mixture of hydrophilic and hydrophobic layers. Adjacent layers in a multilayer tablet may be separated by an insoluble barrier layer or hydrophilic separation layer. An insoluble barrier layer may be formed of materials used to form the insoluble casing. A hydrophilic separation layer may be formed from a material more soluble than the other layers of the tablet core so that as the separation layer dissolves the release layers of the tablet core are exposed.

Suitable release rate controlling polymers include polymethacrylates, ethylcellulose, hydroxypropylmethylcellulose, methylcellulose, hydroxyethylcellulose, hydroxypropylcellulose, sodium carboxymethylcellulose, calcium carboxymethylcellulose, acrylic acid polymer, polyethylene glycol, polyethylene oxide, carrageenan, cellulose acetate, zein etc.

Suitable materials which swell on contact with aqueous liquids include polymeric materials include from cross-linked sodium carboxymethylcellulose, cross-linked hydroxypropylcellulose, high molecular weight hydroxypropylcellulose, carboxymethylamide, potassium methacrylatedivinylbenzene copolymer, polymethylmethacrylate, cross-linked polyvinylpyrrolidone and high molecular weight polyvinylalcohols.

Solid unit dose forms comprising a substance of the invention may be packaged together in a container or presented in foil strips, blister packs or the like, e.g. marked with days of the week against respective doses, for patient guidance.

There is also a need for formulations which could improve patient compliance, for example in case of elderly or paediatric patients A formulation in powder dose form could be either diluted in water, reconstituted or dispersed.

Combinations

The compound of the present invention may be used as the sole active ingredient or in combination with another phosphate binding agent. It may also be used in combination with a calcimimetic such as cinacalet, vitamin or calcitriol.

In a further aspect the present invention provides use of a compound of the present invention or obtained/obtainable in accordance with the present invention in the manufacture of a medicament for the prophylaxis or treatment of hyperphosphataemia.

EXAMPLES

General Description of Reaction

The mixed metal compound is formed by the reaction of an aqueous mixture of magnesium sulphate and ferric sulphate with an aqueous mixture of sodium hydroxide and sodium carbonate. The precipitation is carried out at a pH of around 9.8 and a reaction temperature starting at around 22° C. and rising to up to 30° C. upon addition of reactants. The resulting precipitate is filtered, washed, dried and milled.

The synthesis reaction is represented thus.

$$4MgSO_4 + Fe_2(SO_4)_3 + 12NaOH + (XS+1)Na_2CO_3 \rightarrow Mg_4Fe_2(OH)_{12}.CO_3.nH_2O + 7Na_2SO_4 + XSNa_2CO_3$$

This generates a mixed metal compound with a molar ratio of Mg:Fe of typically 2:1 and the reaction by-product sodium sulphate. Excess (XS) sodium carbonate added to the reaction mixture along with the sodium sulphate is washed out of the precipitate.

By changing the molar ratio of $M^{II}:M^{III}$ cations to 1:1, 2:1, 3:1, 4:1 different composition materials were achieved. The excess sodium carbonate and reaction pH were also changed in separate experiments.

The molecular formula of layered double hydroxides can be measured by different methods. The actual method used to determine the molecular formula of the examples herein was determined from the analysis of $M^{II}/M^{III}$ ratio (Method 1), $SO_4$ analysis (Method 5), $CO_3$ analysis (Method 6) and $H_2O$ analysis (Method 12). Formula $[M^{II}_{1-x}M^{III}_x(OH)_2][(CO_3)_{y1}(SO_{4y})_{y2}.mH_2O][Na_2SO_4]_z$ was used to describe the composition of the examples (1-66) shown herein below in further detail for mixed metal compound wherein:

$x=[M^{III}]/([M^{II}]+[M^{III}])$ where $[M^{II}]$ is the number of moles of bivalent metal $M^{II}$ per mole of compound of formula I and $[M^{III}]$ is the number of moles of trivalent metal $M^{III}$ per mole of compound of formula I.

$\Sigma y'$=sum of the moles interlayer anions y1' $(CO_3^{2-})$+y2' $(SO_4^{2-})$ or any other anions wherein $y1'$=wt % $CO_3^{2-}$/Mw $CO_3^{2-}$ $y2'$=(wt % $SO_4^{2-}$total/Mw $SO_4^{2-}$)−(wt % $Na_2O$/Mw $Na_2O$)

Interlayer anions are also defined as bound anions or anions that cannot be removed by washing with water.

$\Sigma y = \Sigma y'*f$ $\Sigma y$=is the sum of moles interlayer anion corrected with the formula normalisation factor (f).

$y1=y1'*f$ $y2=y2'*f$ $f=x/(2*$wt % $M^{III}_2O_3$/Mw $M^{III}_2O_3)$=formula normalisation factor $m'$=wt % $H_2O$/(Mw $H_2O$)

$m=m'*f$ wt % $H_2O=LOD$ (loss on drying measured at 105° C.)

$z=z'*f$ z=amount of sulphate remaining that can be removed by washing and is calculated from the amount of $Na_2O$ the total of which is assumed to be associated with $SO_4^{2-}$ as soluble $Na_2SO_4$ $z'$=wt % $Na_2O$/Mw $Na_2O$ The ratio $x/\Sigma yn$ can be calculated from the values of x and the sum of interlayer anions ($\Sigma yn$) the data for which is inserted below into molecular formula $[Mg_{1-x}Fe_x(OH)_2][(CO_3)_{y1}(SO_4)_{y2}\, m\, H_2O].[Na_2SO_4]_z$

Example 1

Prepared by the method described below for preparation of approximately 250 gram of dried product targeted to have a Mg:Fe molar ratio of 1:1.

The actual molecular formula found by analysis was:

$[Mg_{0.5}Fe_{0.5}(OH)_2][(CO_3)_{0.14}(SO_4)_{0.02}0.4H_2O][Na_2SO_4]_{0.00}$

Wherein x=0.5, y1=0.14, y2=0 02, m=0.4, z=0.

Two starting materials, designated solution 1 and solution 2 were prepared by the method set out below such as to provide an $Na_2CO_3$ excess of 2.7 mole (in reaction equation 1).

Magnesium sulphate and iron sulphate were dissolved in AnalaR™ water to prepare solution 1. In a separate vessel sodium carbonate and sodium hydroxide were dissolved in AnalaR™ water to prepare solution 2. The weights used were calculated to give the desired ratio of metal cations.

For the preparation of solution 1, AnalaR™ water was weighed out into a vessel and stirred using an overhead mixer, into which was dissolved an appropriate amount of ferric sulphate hydrate (GPR grade). Once dissolved, magnesium sulphate (Epsom Salt) was quantitatively transferred to the stirred iron sulphate solution and allowed to dissolve.

For the preparation of solution 2, AnalaR™ water was weighed out into a vessel and stirred using an overhead mixer, into which was dissolved an appropriate amount of sodium carbonate (Pharmakarb). Once dissolved, sodium hydroxide (Pearl Caustic Soda) was quantitatively transferred to the stirred sodium carbonate solution and allowed to dissolve.

The solutions were then added simultaneously to stirred heel water of 1100 cm³ at controlled flow rates sufficient to maintain pH 10.3 in the reaction mixture (+/−0.2 pH units) at a reaction temperature not exceeding 30° C. The final slurry concentration was around 5.1 wt % compound.

When the additions were complete, the reaction mixture was mixed for another 30 minutes and then filtered using a buchner filtration set up. The product slurry was filtered using a vacuum pump and buchner funnel with a Whatman™ hardened ashless filter paper (No 541). After filtering, the filter cake was washed with portions of AnalaR™ water.

The filtered product was then washed with 220 cm³ portions of cold AnalaR™ water. After isolation the product was dried using a preheated oven.

A weight of AnalaR™ water was placed into a vessel. Flow control units were used to deliver the appropriate flow rates of the alkaline carbonate and metal sulphate solutions.

After isolation the washed product was transferred to a vessel and dried in a preheated oven at 120° C. for three hours.

Product sample for analysis were ground using a ball mill (Retsch PM 100). The milling parameters were set depending on the properties of the product.

Product sample for analysis was milled through a stainless steel, 200 mm diameter, 106 μm sieve, using a sieve shaker (Retsch AS-200). Oversize material was returned to the stock dried sample to be reground, until all material is <106 μm.

Example 2

Preparation method as for Example 1 but targeted to have a Mg:Fe molar ratio of 2:1

The actual molecular formula found by analysis was.

$[Mg_{0.54}Fe_{0.36}(OH)_2][(CO_3)_{y1}(SO_4)_{0.03}.0\, 20H_2O][Na_2SO_4]_z$

Example 3

Preparation method as for Example 1 but targeted to have a Mg:Fe molar ratio of 3.1,

Example 4

Preparation method as for Example 1 but targeted to have a Mg:Fe molar ratio of 4:1

Example 5 & 6

'intentionally blank'

Example 7

Preparation method as for Example 1 but targeted to have a Mg:Fe molar ratio of 2:1 and intended ageing (increase in crystallite size) by introducing an additional method step immediately after precipitation wherein the reaction slurry is aged by heat treatment. The slurry is refluxed for 4 hours by using a hot plate and a Liebig condenser to reflux the sample in a sealed flask. The sample was then immediately filtered using a Buchner funnel under vacuum. The aged compound was then isolated using the same method as described for Example 1

The actual molecular formula found by analysis was:

$$[Mg_{0.66}Fe_{0.34}(OH)_2][f(CO_3)_{y1}(SO_4)_{0.01}\cdot 0.09H_2O]\cdot[Na_2SO_4]_z$$

Example 8-24

Preparation method as for Example 2 but with a liquid ferric source of 40.4 to 42.9 wt % ferric sulphate of water industry standard suitable for human consumption conforms to BS EN 890:2004). The method was then varied in that they were conducted at different precipitation pH, different excess of $Na_2CO_3$, and different reaction temperature i.e. either unaged (i.e. at relatively low reaction temperature 15, 30 or 65 Celsius) or aged (at 90 Celsius) according to examples described below. Where the examples were unaged either the solutions were cooled (to 15 Celsius) or no heat-treatment of reaction slurry occurred (at 30 Celsius) or some gentle heating (at 65 Celsius); whereas when aged, heat-treatment of the reaction slurry occurred by using a sealed glass beaker with condenser placed on a hotplate and reaction slurry heated at 90° C. for 4 hours). Where a reaction temperature is not mentioned the reaction was conducted at the standard room temperature of approximately 25-30 Celsius. The reaction slurry was cooled to 15 Celsius by placing the metal beaker in an ice water bath; the temperature was monitored by a thermometer and controlled by the addition and removal of ice. The reaction slurry was heated to 65 Celsius by placing the metal beaker in a thermostatically controlled water bath Grant W38. The temperature was monitored by a thermometer. The reaction slurry conducted at 30 Celsius started at room temperature but gradually rose to a final temperature of 30 Celsius after addition of the reagents. After the addition of the reagents the slurry was mixed for 30 minutes before filtration with the exception of example 21 which was mixed for 960 minutes.

The actual molecular formula determined by analysis, crystallite size, precipitation pH, slurry treatment, excess moles of $Na_2CO_3$ in recipe are listed below for each example. Results of examples 8-24 are shown in Table 3 and FIG. 1.

Example $$[Mg_{0.2}Fe_{0.8}(OH)_2][(CO_3)_{0.16}(SO_4)_{0.0}\cdot 0.42H_2O]\cdot[Na_2SO_4]_{0.00} \qquad 8$$

Crystallite size: not determined (nd)
Precipitation pH=8.0; reaction temperature is 30 Celsius; 2.7 moles excess $Na_2CO_3$ $$[Mg_{0.5}Fe_{0.5}(OH)_2][(CO_3)_{0.14}(SO_4)_{0.02}\cdot 0.39H_2O]\cdot[Na_2SO_4]_{0.00} \qquad 9$$

Crystallite size: >200 Å
Precipitation pH=9.8, reaction temperature is 90 Celsius, 2.7 moles excess $Na_2CO_3$ $$[Mg_{0.5}Fe_{0.5}(OH)_2][(CO_3)_{0.14}(SO_4)_{0.02}\cdot 0.39H_2O]\cdot[Na_2SO_4]_{0.00} \qquad 9b$$

Crystallite size: >200 Å
Precipitation pH=9.8; reaction temperature is 90 Celsius; 4 moles excess $Na_2CO_3$ $$[Mg_{0.67}Fe_{0.38}(OH)_2][(CO_3)_{0.14}(SO_4)_{0.01}\cdot 0.23H_2O]\cdot[Na_2SO_4]_{0.00} \qquad 10$$

Crystallite size: not determined (nd)
Precipitation pH=10.1, reaction temperature is 65° C.; 2.7 moles excess $Na_2CO_3$ $$[Mg_{0.67}Fe_{0.33}(OH)_2][(CO3)_{0.14}(SO_4)_{0.01}\cdot 0.25H_2O]\cdot[Na_2SO_4]_{0.00} \qquad 11$$

Crystallite size: not determined (nd)
Precipitation pH=9.8; reaction temperature is 65° C.; 2.7 moles excess $Na_2CO_3$ $$[Mg_{0.67}Fe_{0.33}(OH)_2][(CO_3)_{0.14}(SO_4)_{0.01}\cdot 0.39H_2O]\cdot[Na_2SO_4]_{0.00} \qquad 12$$

Crystallite size: not determined (nd)
Precipitation pH=11; reaction temperature is 30 Celsius; 4 moles excess $Na_2CO_3$ $$[Mg_{0.67}Fe_{0.34}(OH)_2][(CO_3)_{0.15}(SO_4)_{0.02}\cdot 0.39H_2O]\cdot[Na_2SO_4]_{0.00} \qquad 13$$

Crystallite size: not determined (nd)
Precipitation pH=10.5; reaction temperature is 30 Celsius; 2.7 moles excess $Na_2CO_3$ $$[Mg_{0.67}Fe_{0.33}(OH)_2][(CO_3)_{0.13}(SO_4)_{0.02}\cdot 0.73H_2O]\cdot[Na_2SO_4]_{0.00} \qquad 14$$

Crystallite size: not determined (nd)
Precipitation pH=10.3; reaction temperature is 30 Celsius; 2.7 moles excess $Na_2CO_3$ $$[Mg_{0.67}Fe_{0.33}(OH)_2][(CO_3)_{0.13}(SO_4)_{0.02}\cdot 0.73H_2O]\cdot[Na_2SO_4]_{0.00} \qquad 15$$

Crystallite size: not determined (nd)
Precipitation pH=10.5; reaction temperature is 30 Celsius; 1 moles excess $Na_2CO_3$ $$[Mg_{0.67}Fe_{0.33}(OH)_2][(CO_3)_{0.13}(SO_4)_{0.02}\cdot 0.38H_2O]\cdot[Na_2SO_4]_{0.00} \qquad 16$$

Crystallite size: not determined (nd)
Precipitation pH=10.1; reaction temperature is 30 Celsius; 2 7 moles excess $Na_2CO_3$ $$[Mg_{0.66}Fe_{0.34}(OH)_2][(CO_3)_{0.16}(SO_4)_{0.02}\cdot 0.37H_2O]\cdot[Na_2SO_4]_{0.00} \qquad 17$$

Crystallite size: <100 Å
Precipitation pH=9.8; reaction temperature is 30 Celsius 2.7 moles excess $Na_2CO_3$ $$[Mg_{0.67}Fe_{0.34}(OH)_2][(CO_3)_{0.12}(SO_4)_{0.03}\cdot 0.65H_2O]\cdot[Na_2SO_4]_0 \qquad 18$$

Crystallite size: not determined (nd)
Precipitation pH=9.8; reaction temperature is 30 Celsius; 4 moles excess $Na_2CO_3$ $$[Mg_{0.64}Fe_{0.36}(OH)_2][(CO_3)_{0.12}(SO_4)_{0.03}\cdot 0.38H_2O]\cdot[Na_2SO_4]_{0.00} \qquad 19$$

Crystallite size: not determined (nd)
Precipitation pH=11; reaction temperature is 15° C.; 1 moles excess $Na_2CO_3$ $$[Mg_{0.64}Fe_{0.36}(OH)_2][(CO_3)_{0.12}(SO_4)_{0.03}ndH_2O]\cdot[Na_2SO_4]_{0.00} \qquad 20$$

Crystallite size: not determined (nd)
Precipitation pH=9.6; reaction temperature is 30 Celsius; 2.7 moles excess $Na_2CO_3$ $$[Mg_{0.67}Fe_{0.36}(OH)_2][(CO_3)_{0.13}(SO_4)_{0.04} \cdot 0.56H_2O] \cdot [Na_2SO_4]_{0.00} \qquad 21$$

Crystallite size: not determined (nd)
Precipitation pH=9.5; reaction temperature is 30 Celsius; 27 moles excess $Na_2CO_3$ $$[Mg_{0.62}Fe_{0.38}(OH)_2][(CO_3)_{0.12}(SO_4)_{0.04} \cdot 0.49H_2O] \cdot [Na_2SO_4]_{0.00} \qquad 22$$

Crystallite size: not determined (nd)
Precipitation pH=9.5, reaction temperature is 30 Celsius; 4 moles excess $Na_2CO_3$ $$[Mg_{0.64}Fe_{0.36}(OH)_2][(CO_3)_{0.12}(SO_4)_{0.04} \cdot 0.73H_2O] \cdot [Na_2SO_4]_{0.00} \qquad 23$$

Crystallite size: not determined (nd)
Precipitation pH=9.5, reaction temperature is 30 Celsius, 1 moles excess $Na_2CO_3$ $$[Mg_{0.58}Fe_{0.42}(OH)_2][(CO_3)_{0.1}(SO_4)_{0.05} \cdot 0.43H_2O] \cdot [Na_2SO_4]_{0.00} \qquad 24$$

Crystallite size: not determined (nd)
Precipitation pH=9.5; reaction temperature is 15° C.; 1 moles excess $Na_2CO_3$ Example 25-27

Preparation method and Mg:Fe ratio as for Example 2 with a ferric source of 40.4 to 42.9 wt % ferric sulphate of water industry standard suitable for human consumption conforms to BS EN 890:2004 and with precipitation pH varied in accordance with Table 4 and filtered.

Example The actual molecular formula found by analysis was:

$$[Mg_{0.65}Fe_{0.35}(OH)_2][(CO_3)_{y.1}(SO_4)_{y.2} mH_2O] \cdot [Na_2SO_4]_{0.00} \qquad 25$$

$$[Mg_{0.65}Fe_{0.35}(OH)_2][(CO_3)_{y.1}(SO_4)_{y.2} \cdot mH_2O] \cdot [Na_2SO_4]_z \qquad 26$$

$$[Mg_{0.65}Fe_{0.35}(OH)_2][(CO_3)_{0.13}(SO_4)_{0.02} mH_2O] \cdot [Na_2SO_4]_{0.01} \qquad 27$$

Example 28

To make 163 kg of the mixed metal compound (dry basis) two starting solutions were prepared designated solution A and solution B. To prepare solution A, 138 kg (dry basis) iron sulphate of 404 to 42.9 wt % ferric sulphate of water industry standard suitable for human consumption conforms to BS EN 890:2004, 166 kg (dry basis) magnesium sulphate (added as the hepta-hydrate) were dissolved in a total of 1034 kg of water where this total water amount includes the water associated with the ferric sulphate solution. To prepare solution B, 173 kg sodium hydroxide and 129 kg sodium carbonate were dissolved in 948 kg of water to provide homogenous solutions. The reaction vessel water heel was 840 kg. The water supplied to the heel was 30% of the total water supplied.

The reactant solution temperatures are adjusted to around 22° C. prior to addition. The reactant streams (solutions A and 8) are then simultaneously fed to the reaction vessel at a rate such as to maintain a reaction pH of 9.8. Cooling of the vessel contents is applied such as to maintain a temperature of 20-25° C. A heel of purified water is introduced prior to the introduction of the reactant streams in order to enable agitation of the vessel in the initial reaction phase and to give a final slurry concentration of around 5.1 wt % compound.

The vessel is agitated using a high turnover, low shear axial flow agitator operating at a power per unit volume of 0.1 $kW/m^3$ and where the reactant solutions are delivered to an area of high turnover. The reactor is baffled in order to promote good mixing.

The precipitate slurry is held in the reaction vessel (also referred to as hold time) for up to 12 hours and is transferred in aliquots to a vertical filtering centrifuge for isolation and washing, using purified water so as to provide maximum product rate. Washing is terminated to achieve a residual sodium content (expressed as $Na_2O$ in the dried product) of less than 0.40 wt %.

The wet cake is discharged from the centrifuge and is dried in a spherical, agitated vacuum drier. Vacuum and shell temperature are adjusted to provide a product temperature in the dryer of approximately 72° C. The rate of drying was 0.26 kg water/(kg dried product·hr) a residence time of 12 hours and a product rate per unit area of 4.6 kg product/($m^2$·hr).

The dried product is first coarse milled using a de-lumping mill to a particle size distribution (Test Method 24) of typically 200 micron (D50) followed by final micronisation to a particle size of typically 5 micron (D50).

Example The actual molecular formula found by analysis was:

$$[Mg_{0.66}Fe_{0.34}(OH)_2][(CO_3)_{0.12}(SO_4)_{0.03} 0.20H_2O] \cdot [Na_2SO_4]_{0.00} \qquad 28$$

Example 28b

Particle size distribution was measured in the reaction slurry after the addition of the reagents and after a hold time of 4 hours and filtration rate measured during the isolation step.

Example 28c

Alternative Reaction Systems

CFD (Test Method 27) was applied to example 28 in order to derive a mixing power per unit volume at the point of addition of the reactant streams The calculations were based on system having:
Slurry density: 1200 kg·m−3
Slurry viscosity: 20 cP (0.02 Pa·s)
Agitator Shaft speed: 100 rpm
Baffling: Flat plates The pattern of mixing is demonstrated via particle tracks from each of the two reactant stream inlets and shows that the streams remain effectively segregated from each other before the fluid has dispersed widely into the bulk. Contours of concentration were also generated and confirm that mixing into the bulk takes place very rapidly.

To derive the requirements for the manufacture of mixed metal compounds for alternative mixing systems (e.g. static mixers), the findings for the conventional low shear agitated system (described above) have been applied.

Alternative mixing systems such as static mixers, jet mixers, or dynamic in-line mixers and in particular a Kenics KM static mixer may be suitable to provide a volume in which the reaction can take place and suitable to deliver the necessary mixing regime. For example the Kenics KM static mixer using a notional feed zone volume of 5×10 $m^3$, to provide a power to mass ratio (1.28 W/kg—equivalent to 1.54 $kW/m^3$) and residence time (1.25 sec). The length was fixed by the recommended minimum length of 4 elements (hence L/D=6). The resulting diameter was 100 mm and the flowrate 280 liter/min.

To summarise, for a conventionally agitated reaction systems a power per unit volume range (mixing intensity) of 0.03 to 0.5 kW/m3 has been established as optimum. Using alternative mixing equipment, a power per unit volume range (mixing intensity) of 0.03 to 1.6 kW/m3 has been established as optimum.

Example 29

As for example 28 but with a reaction pH of 10.3.

Example 30

As for example 28 but with a batch size of 7 kg using a single-aliquot feed to the Neutsch filter instead of centrifuge such that the reaction mass is isolated and washed within a time period of no more than 16 hours, a tray oven instead of a spherical drier and milled.

The wet cake is discharged from the Neutsch filter and is dried in a vacuum tray oven where the oven walls are heated to 120 to 130° C. and regular manual redistribution of the drying mass is carried out. The rate of drying was 0.38 kg water/(kg dried product hr) with a total drying time of 12 to 16 hours and a product rate per heated dryer surface area of 0.2 kg product/(m²·h).

The dried product is micronised using an impact mill to a particle size of typically 5 micron (D50, Test Method 24).

Example The actual molecular formula found by analysis was.

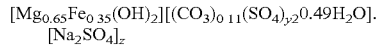

$$[Mg_{0.65}Fe_{0.35}(OH)_2][(CO_3)_{0.11}(SO_4)_{y2}0.49H_2O]\cdot[Na_2SO_4]_z \qquad 30$$

Example 31

As for example 30 but with a reaction pH of 10.3.
Example The actual molecular formula found by analysis was:

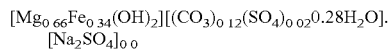

$$[Mg_{0.66}Fe_{0.34}(OH)_2][(CO_3)_{0.12}(SO_4)_{0.02}0.28H_2O]\cdot[Na_2SO_4]_{0.0} \qquad 31$$

Example 32

As for example 28 but with a Vacuum Belt filter instead of centrifuge.

Samples of wet cake discharged from the Vacuum Belt filter were dried in the laboratory oven at 120° C. for three hours.

Product sample for analysis were ground using a ball mill to allow it to pass through a 106 μm sieve.

Example 33

A reaction slurry was prepared according to the method of example 2 but with a reaction pH of 9.6, a liquid ferric source (a solution 40.4 to 42.9 wt % ferric sulphate of water industry standard suitable for human consumption conforms to BS EN 890:2004) and a nominal 400 cm³ batch size. The reaction slurry was washed using Tangential Flow Filtration (Sartorius Slice 200 bench top system with 200 cm² filtration area, PESU 0.1 micron membrane) operated in constant rate mode. The system was flushed and filled with DI water prior to filtration, the permeate rate was regulated to prevent filter blockage. Filtration with wash water addition (diafiltration) was carried out to achieve a residual sodium content (expressed as Na₂O in the dried product) of less than 0.40 wt %. The washed slurry was then concentrated using conventional vacuum filtration and dried in a laboratory oven.

Example The actual molecular formula found by analysis was

$$[Mg_{0.65}Fe_{0.35}(OH)_2][(CO_3)_{y1}(SO_4)_{y2}mH_2O]\cdot[Na_2SO_4]_z \qquad 33$$

Example 34

As for example 33 but with a reaction pH of 10.1

Example 35

As for example 33 but with a reaction pH of 10.3.
Example The actual molecular formula found by analysis was

$$[Mg_{0.65}Fe_{0.35}(OH)_2][(CO_3)_{y1}(SO_4)_{y2}mH_2O]\cdot[Na_2SO_4]_z \qquad 35$$

Example 36

A reaction slurry was prepared for processing according to the method of Example 28. However, 620 kg of reaction slurry were subsequently processed using Tangential Flow Filtration instead of centrifugation A reaction pH of 9.8 was used.

Prior to filtration, to reduce the risk of membrane blockage, the reaction slurry was circulated through a wet colloid mill in order to reduce the D50 particle size (Test Method 9) from 60 to 51 micron.

A Sartorius Sartoflow Beta filtration unit was used with eleven Sartocon II membranes giving a total filtration area of 7.7 m2. The system was flushed and filled with DI water prior to filtration, the permeate rate was regulated to prevent filter blockage. A rotary lobe pump was used to circulate slurry through the system at an inlet pressure of between 2 and 3.5 bar and a typical retentate flow of 3400 l/h. Filtration with wash water addition (diafiltration) was carried out until to achieve a residual sodium content (expressed as Na₂O in the dried product) of less than 0.40 wt %.

A representative quantity of slurry was sampled and isolated and dried in accordance with the method of Example 1 but without additional cake washing Example 37

As for example 36 but with a reaction pH of 10.3. The particle size (D50, Test Method 9) was reduced by wet milling from 47 to 44 micron.

Example 38

As for example 28 but the method was then varied in that they were conducted with slightly different drying conditions. The rate of drying was approximately 0.27 kg water/(kg dried product hr), a residence time of 13 hours, a product rate per unit area of 1.4 kg product/(m²·hr), and the maximum dryer temperature achieved is approximately 85° C.

Example The actual molecular formula found by analysis was

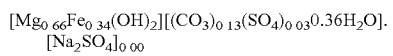

$$[Mg_{0.66}Fe_{0.34}(OH)_2][(CO_3)_{0.13}(SO_4)_{0.03}0.36H_2O]\cdot[Na_2SO_4]_{0.00} \qquad 38$$

Example 39

As for example 28 but the method was then varied in that they were conducted with different drying conditions. The rate of drying was approximately 0.38 kg water/(kg dried product hr), a residence time of 9 hours and a product rate per unit area of 12 kg product/(m²·hr).

Example The actual molecular formula found by analysis was:

$$[Mg_{0.67}Fe_{0.33}(OH)_2][(CO_3)_{0.13}(SO_4)_{0.02}\cdot 0.26H_2O]\cdot[Na_2SO_4]_{0.00} \qquad 38$$

Example 40

As for example 30 but the method was then varied in that they were conducted with different drying conditions. The rate of drying was approximately 0.21 kg water/(kg dried product·hr) a residence time of 18 hours and a product rate per unit area of 0 1 kg product/(m²·hr).

Example 41

As for example 30 but the method was then varied in that they were conducted with different drying conditions. The rate of drying was approximately 0.27 kg water/(kg dried product hr) a residence time of 16 hours and a product rate per unit area of 0.2 kg product/(m²·hr).

Example The actual molecular formula found by analysis was:

$$[Mg_{0.66}Fe_{0.34}(OH)_2][(CO_3)_{0.13}(SO_4)_{0.02}\cdot mH_2O]\cdot[Na_2SO_4]_{0.00} \qquad 41$$

Example 42-47

As for example 28 but the method was then varied in that they were conducted with different drying conditions as described in Table 7 when dried with a spherical, agitated vacuum drier (long residence dryer).

Example The actual molecular formula found by analysis was:

$$[Mg_{0.66}Fe_{0.34}(OH)_2][(CO_3)_{0.13})_{0.02}\cdot 0.53H_2O]\cdot[Na_2SO_4]_{0.01} \qquad 43$$

$$[Mg_{0.65}Fe_{0.35}(OH)_2][(CO_3)_{0.12}(SO_4)_{0.03}\cdot mH_2O]\cdot[Na_2SO_4]_{0.00} \qquad 44$$

$$[Mg_{0.67}Fe_{0.33}(OH)_2][(CO_3)_{0.13}(SO_4)_{0.03}\cdot mH_2O]\cdot[Na_2SO_4]_{0.00} \qquad 45$$

$$[Mg_{0.66}Fe_{0.34}(OH)_2][(CO_3)_{0.12}(SO_4)_{0.03}\cdot 0.29H_2O]\cdot[Na_2SO_4]_{0.00} \qquad 46$$

$$[Mg_{0.65}Fe_{0.35}(OH)_2][(CO_3)_{0.13}(SO_4)_{0.03}\cdot mH_2O]\cdot[Na_2SO_4]_{0.00} \qquad 47$$

Example 48-49

As for example 28 (centrifugation) but the method was then varied in that the filter-cake was dried using a short residence type drier (Spin-Flash Drier, manufacturer/model; Anhydro/SFD51) wherein the delta T was 0.40 (Example 48) or a delta T of 0.66 (Example 49)

Conditions Spray Drier

| Example | $T_{in}$ (°C.) | $T_{out}$ (°C.) | delta T | Rotor speed (%) | Product rate (kg/h) |
|---|---|---|---|---|---|
| 48 | 250 | 150 | 0.40 | 90 | 8 |
| 49 | 350 | 120 | 0.66 | 45 | 20 |

Delta T = $(T_{in} - T_{out})/T_{in}$

Example The actual molecular formula found by analysis was.

$$[Mg_{0.65}Fe_{0.35}(OH)_2][(CO_3)_{0.15}(SO_4)_{0.02}\cdot 0.19H_2O]\cdot[Na_2SO_4]_{0.00} \qquad 48$$

$$[Mg_{0.65}Fe_{0.34}(OH)_2][(CO_3)_{0.14}(SO_4)_{0.02}\cdot 0.16H_2O]\cdot[Na_2SO_4]_{0.00} \qquad 49$$

Example 50

As for example 36 (tangential flow filtration) but the method was then varied in that the slurry was dried using a short residence type drier (Spray Drier, manufacturer/model; Anhydro/CSD71) with a delta T of 0.69.

Conditions Spray Drier

| Example | $T_{in}$ (°C.) | $T_{out}$ (°C.) | delta T | Tip speed (Hz) |
|---|---|---|---|---|
| 50 | 350 | 110 | 0.40 | 208.3 |

Delta T = $(T_{in} - T_{out})/T_{in}$

Example The actual molecular formula found by analysis was:

$$[Mg_{0.66}Fe_{0.34}(OH)_2][(CO_3)_{0.14}(SO_4)_{0.02}\cdot 0.37H_2O]\cdot[Na_2SO_4]_{0.01} \qquad 50$$

Example 51-52

As for example 28 (centrifugation) but the method was then varied in that the filter-cake was first diluted to provide a 10.1 wt % slurry and then dried using a short residence type drier (Spray Drier, manufacturer/model, Anhydro/CSD71) wherein the delta T was 0.74 (Example 51) or a delta T of 0.76 (Example 52)

Conditions Spray Drier

| Example | $T_{in}$ (°C.) | $T_{out}$ (°C.) | delta T | Tip speed (Hz) |
|---|---|---|---|---|
| 51 | 350 | 110 | 0.74 | 208.3 Hz |
| 52 | 325 | 120 | 0.76 | 208.3 Hz |

Example The actual molecular formula found by analysis was:

$$[Mg_{0.66}Fe_{0.34}(OH)_2][(CO_3)_{0.14}(SO_4)_{0.01}\cdot 0.34H_2O]\cdot[Na_2SO_4]_{0.01} \qquad 51$$

$$[Mg_{0.65}Fe_{0.35}(OH)_2][(CO_3)_{0.14}(SO_4)_{0.3}\cdot 0.38H_2O]\cdot[Na_2SO_4]_{0.00} \qquad 52$$

Example 53-59

As for example 28 (centrifugation) but the method was then varied in that instead of micronisation the dried product was only coarse-milled to 343 micron (μm) (D50) and hereafter separated into 6 different particle size fractions by sieving. Six different sieves were used with a sieve parameter size of respectively; base, 20 micron, 75 micron, 106 micron, 180 micron, 355 micron. The sieve fractions were obtained by hand-sieving. The 6 different sieve fractions (Example 53-58) obtained by this method are described in Table 9.

Example The actual molecular formula found by analysis was:

$$[Mg_{0.65}Fe_{0.35}(OH)_2][(CO_3)_{y1}(SO_4)_{0.03} \cdot mH_2O] \cdot [Na_2SO_4]_{0.00} \quad 53$$

Sieve fraction: >355 µm $$[Mg_{0.65}Fe_{0.35}(OH)_2][(CO_3)_{y1}(SO_4)_{0.03} \cdot mH_2O] \cdot [Na_2SO_4]_{0.00} \quad 54$$

Sieve fraction: 180-355 µm $$[Mg_{0.65}Fe_{0.35}(OH)_2][(CO_3)_{y1}(SO_4)_{0.03} \cdot mH_2O] \cdot [Na_2SO_4]_{0.00} \quad 55$$

Sieve fraction: 106-180 µm $$[Mg_{0.65}Fe_{0.35}(OH)_2][(CO_3)_{y1}(SO_4)_{0.03} \cdot mH_2O] \cdot [Na_2SO_4]_{0.00} \quad 54$$

Sieve fraction: 75-106 µm $$[Mg_{0.65}Fe_{0.35}(OH)_2][(CO_3)_{y1}(SO_4)_{0.03} \cdot mH_2O] \cdot [Na_2SO_4]_{0.00} \quad 57$$

Sieve fraction: <106 µm $$[Mg_{0.65}Fe_{0.35}(OH)_2][(CO_3)_{y1}(SO_4)_{0.03} \cdot mH_2O] \cdot [Na_2SO_4]_{0.00} \quad 58$$

Sieve fraction: <20 µm $$[Mg_{0.65}Fe_{0.34}(OH)_2][(CO_3)_{0.12}(SO_4)_{0.03} \cdot 0.26H_2O] \cdot [Na_2SO_4]_{0.00} \quad 59$$

micronised

Example 60

As for example 28 but the method was then varied in that they were conducted with different drying conditions. The rate of drying was approximately 0 33 kg water/(kg dried product hr), a residence time of 9.8 hours and a product rate per unit area of 1.6 kg product/($m^2$·hr) and the maximum dryer temperature achieved is approximately 76° C.

Example The actual molecular formula found by analysis was:

$$[Mg_{0.65}Fe_{0.35}(OH)_2][(CO_3)_{0.12}(SO_4)_{0.03} \cdot mH_2O] \cdot [Na_2SO_4]_{0.00} \quad 60$$

Example 61

As for example 28 but the method was then varied in that they were conducted with different drying conditions. The rate of drying was approximately 018 kg water/(kg dried product hr), a residence time of 10.3 hours and a product rate per unit area of 1.5 kg product/($m^2$·hr) and the product temperature achieved is approximately 64° C.

Example The actual molecular formula found by analysis was:

$$[Mg_{0.66}Fe_{0.34}(OH)_2][(CO_3)_{0.13}(SO_4)_{0.03} \cdot mH_2O] \cdot [Na_2SO_4]_{0.00} \quad 61$$

Example 62-65

As for Example 2 but the method was then varied in that they were conducted at different pH, different excess of $Na_2CO_3$ and different ferric source in accordance with Table 12, Furthermore, Example 62 was prepared with aluminium sulphate in place of iron sulphate.

Two different ferric source designated A and B were used:
A: of GPR grade Rectapur
B: a more pure ferric source such as a solution 40.4 to 42.9 wt % ferric sulphate of water industry standard suitable for human consumption conforms to BS EN 890:2004, Example The actual molecular formula found by analysis was:

$$[Mg_{0.75}Al_{0.21}(OH)_2][(CO_3)_{0.16}(SO_4)_{0.02} \cdot mH_2O] \cdot [Na_2SO_4]_{0.00} \quad 62$$

$$[Mg_{0.66}Fe_{0.34}(OH)_2][(CO_3)_{0.14}(SO_4)_{0.02} \cdot 0.22H_2O] \cdot [Na_2SO_4]_{0.00} \quad 63$$

$$[Mg_{0.66}Fe_{0.34}(OH)_2][(CO_3)_{y1}(SO_4)_{0.02} \cdot mH_2O] \cdot [Na_2SO_4]_{0.00} \quad 64$$

$$[Mg_{0.66}Fe_{0.34}(OH)_2][(CO_3)_{y1}(SO_4)_{0.01} \cdot mH_2O] \cdot [Na_2SO_4]_{0.00} \quad 65$$

Example 66

As for example 28 but the method was then varied in that the filter-cake was dried using a short residence type drier (Spin-Flash Drier, manufacturer/model; Anhydro/SFD51) wherein the delta T was 0.48

Conditions Spin Flash Drier

| Example | $T_{in}$ (° C.) | $T_{out}$ (° C.) | delta T | Atomiser speed, Hz |
|---|---|---|---|---|
| 66 | 250 | 130 | 0.48 | 90 |

Delta T = $(T_{in} - T_{out})/T_{in}$

Example The actual molecular formula found by analysis was $$[Mg_{0.65}Fe_{0.35}(OH)_2][(CO_3)_{0.14}(SO_4)_{0.03} \cdot 0.31H_2O] \cdot [Na_2SO_4]_{0.00} \quad 66$$

Methods

Test Method 1 XRF Analysis

XRF analysis of the product was performed by using a Philips PW2400 Wavelength Dispersive XRF Spectrometer. The sample was fused with 50:50 lithium tetra/metaborate (high purity) and presented to the instrument as a glass bead. All reagents used were analytical grade or equivalent unless specified. AnalaR™ water, Lithium tetraborate 50% metaborate 50% flux (high purity grade ICPH Fluore-X 50). A muffle furnace capable of 1025° C., extended tongs, hand tongs, Pt/5% Au casting tray and Pt/5%/Au dish were used. 1.5 g (+/−0.0002 g) of sample and 7.5000 g (+/−0.0002 g) of tetra/metaborate was accurately weighed out into a Pt/5%/Au dish. The two constituents were lightly mixed in the dish using a spatula, prior to placement in the furnace preset to 1025° C. for 12 minutes. The dish was agitated at 6 minutes and 9 minutes to ensure homogeneity of the sample. Also at 9 minutes the casting tray was placed in the furnace to allow for temperature equilibration. After 12 minutes the molten sample was poured into the casting tray, which was removed from the furnace and allowed to cool. The bead composition was determined using the spectrophotometer.

The XRF method was used to determine the Al, Fe, Mg, Na and total sulphate content of the compound as well as the MII to MIII ratio.

Test Method 2 X-Ray Diffraction (XRD) Measurements

Data was collected for fine particulate samples from 2-70° 2θ on a Philips automatic powder X-ray diffractometer using Copper K alpha radiation generated at 40 kV and 55 mA.

Powder X-ray diffraction (XRD) data were collected from 2-70 degrees 2 theta on a Philips PW 1800 automatic powder X-ray diffractometer using copper K alpha radiation generated at 40 kV and 55 mA, a 0.02 degree 2 theta step size with a 4 second per step count time. An automatic divergence slit giving an irradiated sample area of 15×20 mm was used, together with a 0.3 mm receiving slit and a diffracted beam monochromator.

The approximate volume average crystallite size can be determined from the width, at half peak height, of the powder X-ray diffraction peak at about 11.5 degrees 2 theta (the peak is typically in the range 8 to 15 degrees 2 theta for hydrotalcite type materials) using the relationship given in Table 1 which is derived using the Scherrer equation. The contribution to the peak width from instrument line broadening was 0.15 degrees, determined by measuring the width of the peak at approximately 21.4 degrees 2 theta of a sample of $LaB_8$ (NIST SRM 660) under the same conditions

TABLE 1

XRD Peak width conversion to crystallite size using the Scherrer equation

| Peak width FWHM B (measured) (°2Θ) | B(measured) - b (instrument) (°2Θ) | D - Calculated crystallite size (Å) |
|---|---|---|
| 0.46 | 0.31 | 258 |
| 0.47 | 0.32 | 250 |
| 0.48 | 0.33 | 242 |
| 0.49 | 0.34 | 235 |
| 0.50 | 0.35 | 228 |
| 0.51 | 0.36 | 222 |
| 0.52 | 0.37 | 216 |
| 0.53 | 0.38 | 210 |
| 0.54 | 0.39 | 205 |
| 0.55 | 0.40 | 200 |
| 0.56 | 0.41 | 195 |
| 0.57 | 0.42 | 190 |
| 0.58 | 0.43 | 186 |
| 0.59 | 0.44 | 181 |
| 0.60 | 0.45 | 177 |
| 0.61 | 0.46 | 174 |
| 0.62 | 0.47 | 170 |
| 0.63 | 0.48 | 166 |
| 0.64 | 0.49 | 163 |
| 0.65 | 0.50 | 160 |
| 0.66 | 0.51 | 157 |
| 0.67 | 0.52 | 154 |
| 0.68 | 0.53 | 151 |
| 0.69 | 0.54 | 148 |
| 0.70 | 0.55 | 145 |
| 0.71 | 0.56 | 143 |
| 0.72 | 0.57 | 140 |
| 0.73 | 0.58 | 138 |
| 0.74 | 0.59 | 135 |
| 0.75 | 0.60 | 133 |
| 0.76 | 0.61 | 131 |
| 0.77 | 0.62 | 129 |
| 0.78 | 0.63 | 127 |
| 0.79 | 0.64 | 125 |
| 0.80 | 0.65 | 123 |
| 0.81 | 0.66 | 121 |
| 0.82 | 0.67 | 119 |
| 0.83 | 0.68 | 117 |
| 0.84 | 0.69 | 116 |
| 0.85 | 0.70 | 114 |
| 0.86 | 0.71 | 112 |
| 0.87 | 0.72 | 111 |
| 0.88 | 0.73 | 109 |
| 0.89 | 0.74 | 108 |
| 0.90 | 0.75 | 106 |
| 0.91 | 0.76 | 105 |
| 0.92 | 0.77 | 104 |
| 0.93 | 0.78 | 102 |
| 0.94 | 0.79 | 101 |
| 0.95 | 0.80 | 100 |
| 0.96 | 0.81 | 99 |
| 0.97 | 0.82 | 97 |
| 0.98 | 0.83 | 96 |
| 0.99 | 0.84 | 95 |
| 1.00 | 0.85 | 94 |
| 1.01 | 0.86 | 93 |
| 1.02 | 0.87 | 92 |
| 1.03 | 0.88 | 91 |
| 1.04 | 0.89 | 90 |
| 1.05 | 0.90 | 89 |
| 1.06 | 0.91 | 88 |
| 1.07 | 0.92 | 87 |
| 1.08 | 0.93 | 86 |
| 1.09 | 0.94 | 85 |
| 1.10 | 0.95 | 84 |
| 1.11 | 0.96 | 83 |
| 1.12 | 0.97 | 82 |
| 1.13 | 0.98 | 81 |
| 1.14 | 0.99 | 81 |
| 1.15 | 1.00 | 80 |
| 1.16 | 1.01 | 79 |
| 1.17 | 1.02 | 78 |
| 1.18 | 1.03 | 78 |
| 1.19 | 1.04 | 77 |
| 1.20 | 1.05 | 76 |
| 1.21 | 1.06 | 75 |
| 1.22 | 1.07 | 75 |
| 1.23 | 1.08 | 74 |
| 1.24 | 1.09 | 73 |
| 1.25 | 1.10 | 73 |
| 1.26 | 1.11 | 72 |
| 1.27 | 1.12 | 71 |
| 1.28 | 1.13 | 71 |
| 1.29 | 1.14 | 70 |
| 1.30 | 1.15 | 69 |
| 1.31 | 1.16 | 69 |

The values in Table 1 were calculated using the Scherrer equation:

$$D = K^* \lambda / \beta^* \cos \Theta \qquad \text{Equation 1}$$

Where:
- $D$ = crystallite size (Å)
- $K$ = shape factor
- $\lambda$ = wavelength of radiation used (in Å)
- $\beta$ = peak width measured as FWHM (full width at half maximum height) and corrected for instrument line broadening (expressed in radians)
- $\Theta$ = the diffraction angle (half of peak position $2\Theta$, measured in radians)

Shape Factor

This is a factor for the shape of the particle, typically between 0.8-1.0, a value of 0.9 is used.

Wavelength of Radiation

This is the wavelength of the radiation used. For copper K alpha radiation the value used is 1.54056 Å.

Peak Width

The width of a peak is the sum of two sets of factors: instrumental and sample.

The instrumental factors are typically measured by measuring the peak width of a highly crystalline sample (very narrow peaks). Since a highly crystalline sample of the same material is not available, $LaB_6$ has been used. For the current measurements an instrument value of 0.15 degrees has been used.

Thus for the most accurate measure of crystallite size using the Scherrer equation, the peak width due to instrumental factors should be subtracted from the measured peak width i.e.:

$$\beta = B_{(measured)} - b_{(instrumental)}$$

The peak width is then expressed in radians in the Scherrer equation.

The peak width (as FWHM) has been measured by fitting of a parabola or another suitable method to the peak after subtraction of a suitable background.

Peak Position

A value of 11.5° 2Θ has been used giving a diffraction angle of 5.75°. Corresponding to 0.100 radians.

Test Method 3 Phosphate Binding Capacity and Mg Release

Phosphate buffer (pH=4) was prepared by weighing 5.520 g (+/−0.001 g) of sodium di-hydrogen phosphate followed by addition of AnalaR™ water and transferring to a 1 ltr volumetric flask To the 1 liter volumetric flask was then added 1M HCl drop-wise to adjust the pH to pH 4 (+/−0.1) mixing between additions. The volume was then accurately made up to 1 ltr using AnalaR™ water and mixed thoroughly.

0.5 g (+/−0.005 g) of each sample was added to a volumetric flask (50 ml) containing 40 mM phosphate buffer solution (12.5 ml) at 37.5° C. in a Grant OLS 200 Orbital shaker. All samples were prepared in duplicate. The vessels were agitated in the orbital shaker for 30 minutes. The solution was then filtered using a 0.45 μm syringe filter. 2.5 $cm^3$ aliquots of supernatant were pipetted of the supernatant and transferred into a fresh blood collection tubes. 7.5 $cm^3$ of AnalaR™ water were pipetted to each 2.5 $cm^3$ aliquot and the screw cap fitted and mixed thoroughly. The solutions were then analysed on a calibrated ICP-OES.

The phosphate binding capacity was determined by:

$$\text{Phosphate binding}(mmol/g) = S_P(mmol/l) - T_P(mmol/l)/W(g/l)$$

where:
$T_P$=Analyte value for phosphate in the phosphate solution after reaction with phosphate binder=solution P (mg/l)*4/30.97,
$S_P$=Analyte value for phosphate in the phosphate solution before reaction with phosphate binder.
W=concentration binder (g/l) used in test method (i.e 0.4 g/10 $cm^3$=40 g/l)

Magnesium release was determined by:

$$\text{Magnesium release}(mmol/g) = T_{Mg}(mmol/l) - S_{mg}(mmol/l)/W(g/l)$$

where
$T_{Mg}$=Analyte value for magnesium in the phosphate solution after reaction with phosphate binder=.solution Mg (mg/l)*4/2431
$S_{Mg}$=Analyte value for magnesium in the phosphate solution before reaction with phosphate binder.

Fe release was not reported as the amount of iron released from the compound was too small and below detection limit.

Test Method 4 Phosphate Binding and Magnesium Release in Food Slurry

MCT peptide2+, food supplement (SHS International) was mixed to form a slurry of 20% (w/v) in 0.01M HCl. Separate aliquots of 0.05 g dry compound were mixed with 5 $cm^3$ of the food slurry and constantly agitated for 30 minutes at room temperature. A 3 $cm^3$ aliquot was removed and centrifuged at 4000 rpm for 10 minutes, and the phosphate and magnesium in solution were measured.

Test Method 5 Sulphate Determination

Total sulphate in the compound

Sulphite ($SO3$) is measured in the compound by XRF measurement (Test Method 1) and expressed as total sulphate ($SO4$) according to:
Total SO4(wt %)=(803)×96180
Total SO4 (mole)=total SO4 (wt %)/molecular weight SO4

Sodium Sulphate (soluble form of sulphate present in the compound)

$Na2O$ is measured in the compound by XRF measurement (Test Method 1).

It is assumed that the $Na2O$ is associated with the more soluble form of $SO4$ in the form of $Na2SO4$ present in the compound.

Consequently, the number of mole $Na2O$ is assumed equal to that of soluble form of sulphate and is therefore calculated as:

$$\text{soluble SO4(mole)} = \text{Na2O(mole)} = \text{wt \% Na2O/molecular weight Na2O}$$

Interlayer sulphate (insoluble form of sulphate present in the compound also referred to as bound sulphate)

The interlayer sulphate is calculated according to:

$$\text{interlayer SO4(mole)} = \text{total SO4(mole)} - \text{soluble SO4 (mole)}$$

$$\text{interlayer SO4(wt \%)} = \text{interlayer SO4(mole)} \times \text{molecular weight SO4}$$

Test Method 6 Carbon Content Analysis by the Leco Method

This method was used to determine the levels of carbon content (indicative of the presence of the carbonate anion present in the mixed metal compound)

A sample of known mass is combusted at around 1350° C. in a furnace in a pure oxygen atmosphere. Any carbon in the sample is converted to $CO_2$ which is passed through a moisture trap before being measured by an infra-red detector. By comparing against a standard of known concentration, the carbon content of the sample can be found. A Leco SC-144DR carbon and Sulphur Analyser, with oxygen supply, ceramic combustion boats, boat lance and tongs was used. 0.2 g (+/−0.01 g) of sample was weighed into a combustion boat. The boat was then placed into the Leco furnace and the carbon content analysed. The analysis was performed in duplicate.

The % C was determined by:

$$\% C(sample) = (\% C_1 + \% C_2)/2$$

Where $C_1$ and $C_2$ are individual carbon results.

The results of the carbon content measurements are seen in Table 3 and FIG. 1 and were expressed as % $CO_2$=% C×44/12

Test Method 7 Wash Time

Wash time was measured in minutes rounded to the nearest minute, it was the time it took for one wash (i.e. one wash volume of water) to be drawn through the filter. The wet cake was not allowed to dry or crack during this period. The time was measured using a stop clock.

Test Method 8 Filtration Time (Lab Scale)

Filtration time was measured in minutes rounded to the nearest minute, it was the time taken for the slurry to be drawn through the filter, but the resulting wet cake was not allowed to dry. The time was measured using a stop clock.

Test Method 9 Particle Size Distribution (PSD) by Lasentech

In process particle size distribution in the slurry was measured using a Lasentech probe The d50 average particle size, is obtained as part of this analytical technique.

Test Method 10 Filtration Rate (ml/min)

Defined as the quantity of filtrate obtained in a given time.

Test Method 11 Filtration Rate (kg dry product/m²·h),

Filtration Rate (kg dry product/m²·h) is defined as the mass of wet cake, expressed as dried compound, isolated, washed, dewatered and discharged per hour, divided by the area of filter used.

Test Method 12 Moisture Content

The moisture content of mixed metal compound is determined from the loss of weight (LOD) following drying at 105'C for four hours at ambient pressure in a laboratory oven.

Test Method 13 [Intentionally Left Blank]

Test Method 14 Surface Area and Pore Volume (Nitrogen Method —$N_2$)

Surface area and pore volume measurements were obtained using nitrogen gas adsorption over a range of relative pressures using a Micromeritics Tristar ASAP 3000. The samples were outgassed under vacuum for 4 hours at 105° C. before the commencement of measurements. Typically a vacuum of <70 mTorr was obtained after outgassing.

Surface areas were calculated by the application of Brunauer, Emmett and Teller (BET) theory using nitrogen adsorption data obtained in the relative pressure range of 0.08 to 0.20 P/Po.

Pore volume was obtained from the desorption loop of the nitrogen adsorption isotherm, using the volume of gas adsorbed at a relative pressure (P/Po) of 0.98. The quantity of gas adsorbed at 0.98 relative pressure (in cc/g at STP) is converted to a liquid equivalent volume by multiplying by the density conversion factor of 0.0015468 This gives the reported pore volume figure in $cm^3/g$.

P=partial vapour pressure of nitrogen in equilibrium with the sample at 77K

Po=saturated pressure of nitrogen gas.

Test Method 15 Pore Volume (water method)

Water Pore Volume

Aim

To fill internal pores of a sample (in powder form) with water such that, when all the pores are filled, the surface tension of the liquid causes the majority of the sample to form an aggregate which adheres to a glass jar on inversion of the jar.

Equipment (1) Wide neck (30 mm) clear glass 120 $cm^3$ powder jar with screw cap. Dimensions: Height 97 mm. Outer Diameter 50 mm. (Fisher part number BTF-600-080)

(2) 10 $cm^3$ Grade A burette (3) Deionised water (4) Rubber bung 74 mm diameter top tapered to 67 mm. Overall height 49 mm (5) Calibrated 4 decimal place balance Procedure (1) a 5.00 g (±0.01) sample in the glass jar, add a 1 $cm^3$ aliquot of water (2) After this addition vigorously knock the bottom end of the sealed jar against the rubber bung 4 times.

(3) Using a sharp swing of the arm, flick the jar with the wrist to invert the jar and check the sample:

a. If the sample agglomerates and the majority (>50%) of the sample adheres to the jar this is the end point (go to results section below). If free water is observed with the sample, the end point has been exceeded and the test should be discarded and started again with a new sample.

b. If the sample dislodges from the jar (even if agglomeration is evident), add a further 0.1 $cm^3$ of water and repeat steps (2) to (3) above until the end point is reached(3a)).

Results

The water pore volume is calculated as follows:—

Water Pore Volume($cm^3$/g)=Volume of water added ($cm^3$)/Sample Weight(g)

Test Method 16 Total Water Added/kg API—Granulation Point

This is the amount of water added to a dry mixture of 80 wt % mixed metal compound and 20 wt % excipients in order to form granulates (i.e. until a granulation point is reached).

Test Method 17 Tablet Volume

The tablet volume is calculated from the dimensions of the tablet using a computer design package (iHolland Ltd).

Test Method 18 Rate of Drying

For the calculation of rate of drying (kg water/(kg dried product·hr)) mass of water removed during drying per unit time was divided by the mass of dry product produced. The time used to calculate the rate of drying is the dryer residence time defined in Test Method 19.

Test Method 19 Dryer Residence Time

For long residence dryers, the residence time is the time during which water is removed from the material being dried.

For short residence dryers such as spray drying, the residence time is calculated as follows.

The internal volume of the dryer is first determined. The residence time of the air or gas fed to the dryer is then calculated by dividing the interval volume by the air or gas flow rate. It is assumed, since a significant build up of solids does not occur within the dryer, that the average particle residence time is approximately equal to the air or gas residence time.

Test Method 20 Product Rate Per Unit Area

The Product rate per unit area kg product/($m^2$·hr) can be calculated by dividing the mass of dry product produced per unit time with the surface area used for heating.

Test Method 21 Delta T

Delta temperature is defined for short residence drying processes as $(T_{in}-T_{out})/T_{in}$ where $T_{in}$ is inlet gas temperature, ° C.

$T_{out}$ is the outlet gas temperature or product temperature, ° C. (assuming gas and product are at the same temperature)

Test Method 22 Tapped Bulk Density

Tapped Bulk Density was determined using a Copley JV1000 Auto tapper. The measurement was made by the addition of the product (50.0 g, +/−5.0 g) into a clean measuring cylinder (dedicated for the apparatus). The exact weight was noted. The initial volume was noted. The cylinder was then placed on the auto tapper and the machine was set for 3750 taps by entering the number of taps required and then pressing start. The volume of the cylinder was taken again when the total number of taps was completed (end volume). The tapped bulk density was calculated as follows, Tapped Bulk Density(g/ml)=weight(g)/end volume (ml)

Test Method 23 Flowability Carr Index

The Carr index was calculated using the following formula and the data available from the Tapped Bulk Density test, Carr Index(%)=100*((initial volume(ml)end volume (ml))/initial volume(ml))

A result greater than 25% indicates poor flow ability and less than 15% indicates good flow ability.

Test Method 24 Average Particle Size Distribution (d50 PSD) of powders

The particle size was determined using a Mastersizer 'S' fitted with a 300 Rf lens and a DIF 2012 dispersion unit. The data was interpreted and analysed using Malvern Mastersizer software. The Malvern was connected to process water supply. The following program parameters were used, 80% pump speed, 80% stirrer speed, 50% ultrasonic and 3 minute residence time. The background level was checked to be below 100 units. When prompted by the program the sample was added in portions to reach between 15%-25% obscuration. The analysis commenced automatically. The residual was checked to be less than 1%. The sample was analysed in duplicate. The results were calculated using the software by taking the % volume under the particle sizes between 1.85 and 184 microns. This was expressed as percentile results with the Average Particle Size (D50, $50^{th}$ percentile), $90^{th}$ Percentile (D90) and $10^{th}$ Percentile (D10).

(Table 2). The release of the magnesium, associated with the pharmaceutical use of mixed metal compounds can be reduced by selecting a suitable Mg:Fe molar ratio. Data showed that material with a ratio of 21 had the highest phosphate binding per mole of magnesium released in a phosphate binding test in the presence of a meal slurry. The data also shows that a Mg:Fe molar ratio of 2:1 does not have the presence of any other non-hydrotalcite phases. In addition, we have found that unaged mixed metal compounds of crystallite size less than 200 angstrom (Å) give higher phosphate binding than those of aged compounds which typically have a crystallite size well above 200 Å.

TABLE 2

Selection of preferred Mg:Fe Molar ratio and Crystallite Size

| Example Number | Mg:Fe Ratio Method 1 | Crystallite Size Method 2 Angstrom (Å) | Phosphate Binding Method 3 mmol/g API | Phosphate bound per mmol/l Mg released Method 4 (food slurry) (%) | Additional Non-Hydrotalcite Phases Method 2 XRD |
|---|---|---|---|---|---|
| 1 | 1.0 | 95 | 0.77 | | yes |
| 2 | 2.0 | 69 | 0.73 | 23.00 | no |
| 3 | 3.0 | <100 | | 7.70 | no |
| 4 | 4.0 | <100 | 0.73 | 5.70 | no |
| 7 | 2.0 | 258 | 0.45 | | no |

Test Method 25 Metal Analysis of Al, Cr, Pb

Samples were acidified, diluted and the specified metals analysed using ICP-MS. Samples were analysed in duplicate.

Test Method 26 Total Heavy Metal Content

The metals were determined by acidifying the samples first followed by analysis using ICP-MS Total heavy metal content (ppm) was then calculated by summating the following metals: As (ppm)+Cd (ppm)+Pb (ppm)+Hg (ppm)+Sb (ppm)+Mo (ppm)+Cu (ppm)

Test Method 27—Power per Unit Volume

Computational Fluid Dynamics (CFD) software application was used to simulate fluid flow within the reaction vessel to establish mixing requirements in mixing equipment.

Results and Discussion

We have encountered critical problems with the larger scale process of manufacture (defined as being from the reaction to drying stages) when trying to prevent increase in crystallite size. This is described in more detail below Phosphate Binding For, high daily and repeated long-term (chronic) dosages required for kidney patients total daily pill count requires a low tablet burden due to restricted fluid intake. Consequently, high dosage of drug substance (mixed metal compound) of up to 80 wt % is required in final product (i.e. tablet) whilst maintaining good therapeutic activity (such as phosphate binding) and storage stability. We have found that the final product is therefore very sensitive to an array of opposing chemical and physical properties of the mixed metal compound such as composition (Mg:Fe ratio, sulphate), crystallite size, morphological properties (surface area, particle size, pore volume) of the mixed metal compounds. This is unlike normal requirements imposed on pharmaceuticals which typically contain more soluble, organic type drug substances at lower concentrations which are less dependent on a particular morphology.

Variants of the Mg:Fe hydrotalcite structure that had different Mg:Fe molar ratios of 2:1, 3:1 and 4:1 were compared for phosphate binding performance and magnesium release However, we have found that if processed incorrectly the mixed metal compounds crystallite size will continue to grow in size and are difficult to filter, particularly at large scale this presents significant problems. We have discovered a novel process for control of different production steps (from reaction to drying) such as to prevent growth of the crystallite size above 200 Å in order to maintain the phosphate binding activity without significantly hindering the process of isolation, washing and drying of the compound. This was achieved by careful selection and control of specific process conditions. Our approach is described in more detail by the following examples.

Precipitation

We have found that the advantages of the mixed metal compound of Mg:Fe molar ratio of approx 2.1 such as good phosphate binding are not only determined by crystallite size but also preferably by low levels of interlayer sulphate and the method of manufacture (Table 3 and FIG. 1). Furthermore, across the pH range considered, filtration is difficult due to the typical clay-like structure of the material.

When preparing the mixed metal compound with the carbonate anion the presence of a second anion-type may be possible. The presence of only one anion-type may be considered more desirable than a mixture of anions. Surprisingly, we discovered that it is not necessarily optimal to have no sulphate but that a small amount of sulphate should exist as interlayer (bound) sulphate in order to increase filtration rates of the clay-like structure whereas the sulphate in the form of soluble salts such as $Na_2SO_4$ should be removed. We found that most of the soluble $Na_2SO_4$ salt can be readily removed by washing whereas the interlayer sulphate is less soluble and its levels are primarily controlled by the amount of excess $Na_2CO_3$ in the recipe, reaction pH and extent of ageing in the reaction slurry (i.e. temperature of reaction slurry). For example, we have found that the interlayer sulphate decreases when: reaction temperature of slurry increases, the excess $Na_2CO_3$ increases, the pH increases.

Optionally, if the interlayer sulphate needs to be reduced further to achieve an even higher purity (i.e. less than 1.0 wt % interlayer sulphate) and initial isolation and washing rates are not to be reduced it may be possible to wash the filter cake again but this time with a solution of $Na_2CO_3$ (preferably up to 1 M concentration) followed by washing with water. This process may reduce or remove the remaining interlayer sulphate without necessarily reducing filtration rates or phosphate binding. However, it is preferred if most of the interlayer sulphate is removed during the reaction stage instead of requiring the need for washing with carbonate. Additional process steps may decrease yield as well as encouraging crystallite size growth.

Therefore in another aspect of the invention the compound is first washed with water to remove soluble $SO_4$ and sodium, followed by a wash with a $Na_2CO_3$ solution to remove the interlayer sulphate, followed by a final wash with water to remove any remaining soluble ions. Preferably the compound is slurried with some $Na_2CO_3$ solution for up to 1 hour to enable exchange of the interlayer sulphate for the carbonate. It is believed that washing with excess $Na_2CO_3$ would encourage removal of any remaining sulphate from the interlayer region. In this aspect after the exchange of the interlayer sulphate for the carbonate there may be provided an Al-free mixed metal compound with less than 1 wt % interlayer sulphate (preferably less than 0.5 wt %) and less than 0.5 wt % soluble sulphate.

Where product is not washed with $Na_2CO_3$ solution we have also found that phosphate binding varies as a function of sulphate level, for example, an optimum interlayer sulphate level exists of between 1.8 to 5% wt, wherein good phosphate binding and filtration is maintained. Phosphate binding decreases below 1.8% wt. Above 5% wt interlayer $SO_4$ becomes more variable and the 804 level is too high to be acceptable and wash and filtration time increases. Best results were obtained between 2.5 and 5 wt % interlayer sulphate.

maintaining a process at scale and a mixed metal compounds with good phosphate binding, storage stability and not negatively affecting the downstream manufacturing processes used to produce the final formulated pharmaceutical product containing the mixed metal compound.

During scale-up we found that it was difficult to prepare this material when using traditional filtration techniques such as a belt filter, Neutsche pressure filter. Even a centrifugation method did not work effectively at this large scale.

We solved this problem by selecting specific ranges from one or more of the following: (i) selection of range of interlayer sulphate (from 1.8 to 5 wt %) by control of $Na_2CO_3$ and pH (ii) selection of a preferred psd of reaction slurry (D50>40 microns, preferably greater than 70 microns) and moisture content of reaction slurry (more than 90 wt %) and filter cake (less than 80 wt %) (iii) selection of a specific agitation regime (a power per unit volume of 0.03 to 1.6 $kW/m^3$), (iv) selection of a preferred filtration method and its operation (centrifuge). In a highly preferred aspect we selected each of the following: (i) selection of range of interlayer sulphate (from 2 to 5 wt %) by control of $Na_2CO_3$ and pH (ii) selection of a preferred psd of reaction slurry (D50>40 microns, preferably greater than 70 microns) and moisture content of reaction slurry (more than 90 wt %) and filter cake (less than 80 wt %) (iii) selection of a specific agitation regime (a power per unit volume of 0.03 to 1.6 $kW/m^3$), (iv) selection of a preferred filtration method (centrifuge).

(i) Interlayer Sulphate

A high filtration rate and a low wash time are advantageous when seeking to manufacture the MgFe mixed metal compounds on a commercial scale and to prevent crystallite growth. However, mixed metal compounds consisting of low interlayer sulphate levels (less than 1.8 wt %) are more difficult to filter and wash whereas if too high in sulphate (above

TABLE 3

Effect and control of interlayer sulphate on wash time and phosphate binding

| Example Number | Temperature celcius | Excess moles Na2CO3 in recipe | Precipitation pH | $Mg^{2+}:Fe^{3+}$ molar ratio Method 1 | Interlayer sulphate % w/w Method 5 | Pi Binding mmol/g Method 3 | Wash Time minutes Method 7 |
|---|---|---|---|---|---|---|---|
| 8 | 30 | 2.7 | 8 | 0.3 | 0.06 | 0.92 | 102.0 |
| 9 | 90 | 2.7 | 9.8 | 1.9 | 0.78 | 0.45 | 90.0 |
| 10 | 65 | 2.7 | 10.1 | 2.1 | 0.85 | 0.58 | 74.6 |
| 11 | 65 | 2.7 | 9.8 | 2.1 | 1.39 | 0.6 | 24.0 |
| 12 | 30 | 4 | 11 | 2.1 | 1.54 | 0.67 | 13.0 |
| 13 | 30 | 2.7 | 10.5 | 1.9 | 1.54 | 0.63 | 55.0 |
| 14 | 30 | 2.7 | 10.3 | 1.9 | 1.73 | 0.7 | 32.0 |
| 15 | 30 | 1 | 10.5 | 2.1 | 2.17 | 0.75 | 3.6 |
| 16 | 30 | 2.7 | 10.1 | 2.1 | 2.47 | 0.74 | 3.2 |
| 17 | 30 | 2.7 | 9.8 | 1.8 | 2.52 | 0.76 | 12.0 |
| 18 | 30 | 4 | 9.8 | 1.9 | 2.56 | 0.77 | 1.2 |
| 19 | 15 | 1 | 11 | 2.1 | 2.84 | 0.76 | 0.0 |
| 20 | 30 | 2.7 | 9.6 | 1.9 | 3.32 | 0.78 | 1.7 |
| 21 | 30 | 2.7 | 9.5 | 1.8 | 3.64 | 0.76 | 1.5 |
| 22 | 30 | 4 | 9.5 | 1.7 | 3.59 | 0.79 | 1.1 |
| 23 | 30 | 1 | 9.5 | 1.8 | 4.61 | 0.82 | 1.5 |
| 24 | 15 | 1 | 9.5 | 1.4 | 5.18 | 0.85 | 21.9 |

Area highlighted is preferred range

Separation

The features of the Al-free mixed metal compounds resulting from their clay-like structure, replacing Al with Fe and their unaged form present limitations when manufactured on a commercial scale. Limitations such as difficult filtration and material hardness have to be resolved whilst at the same time 5 wt %) then washtime increases again (Table 3 and FIG. 1). We found that interlayer sulphate levels can be maintained between 2-5 wt % by controlling the temperature of the reaction slurry, pH during the reaction and a $Na_2CO_3$ (XS) excess range of either one of the following combinations shown below.

When the slurry is maintained to a temperature between 15 and 30° C. wherein the $Na_2CO_3$ is provided at an excess than is required to complete the reaction and a pH at either:
(i) $9.5<pH\leq 11$ and $0\leq Na_2CO_3 \leq 1$ moles
(ii) $9.5\leq pH\leq 10.5$ and $1<Na_2CO_3\leq 2$ moles
(iii) $9.5\leq pH\leq 10.1$ and $1<Na_2CO_3\leq 2.7$ moles
(iv) $9.5\leq pH\leq 10$ and $1<Na_2CO_3\leq 4$ moles
(v) $9.5\leq pH<9.8$ and $1<Na_2CO_3\leq 5$ moles When the slurry is maintained to a temperature from 30 to 60° C. wherein the $Na_2CO_3$ is provided at an excess than is required to complete the reaction and a pH at either:
(i) $9.5<pH<11$ and $0<Na_2CO_3<2$
(ii) $9.5<pH<10.5$ and $0<Na_2CO_3<2.7$ moles
(iii) $9.5<pH<10$ and $0<Na_2CO_3<4$ moles Excess $Na_2CO_3$ (XS) is defined as excess than is required to complete the reaction of:

$$4MgSO_4 + Fe_2(SO_4)_3 + 12NaOH + (XS+1)Na_2CO_3 \rightarrow Mg_4Fe_2(OH)_{12}CO_3 \cdot nH_2O + 7Na_2SO_4 + (XS)Na_2CO_3$$

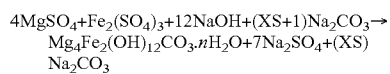

For mixed metal compounds, maintaining the target metal molar ratio (Mg:Fe) at approx 2 (1.8 to 2.2, preferably 1.7 to 2.1) during the reaction whilst controlling the interlayer sulphate is difficult as both are opposingly affected by the way the material is processed. Furthermore, we found that correct stoichiometry is not only determined by the correct ratios of the starting materials but also by pH for the reaction. For example, when the pH is too low (pH below 9.5) incomplete precipitation of magnesium may occur whereby Mg:Fe molar ratio falls well below the target value of 2 and is also not free of non-hydrotalcite crystalline phases. It is therefore preferred to maintain the pH between 9.5 and 11 and preferably between an even narrower pH range of 9.5-10 and more preferably at 9.8 to deliver the optimum magnesium:iron ratio (1.8 to 2.2, preferably 1.7 to 2.1) whilst maintaining good filtration rates during manufacture at scale, maintain good phosphate binding and prevent crystal growth by control of particle size distribution and interlayer sulphate.

The total amount of anion ($C_{calc}$) predicted for a mixed metal compound if it were of an ideal hydrotalcite type phase of a $M^{2+}:M^{3+}$ molar ratio of 2:1 can be calculated by the following formula: $C_{calc} = (M^{3+}/(M^{2+}+M^{3+}))/n$ wherein n is the charge of the anion. For example, a $M^{2+}:M^{3+}$ molar ratio of 2:1 and an assumed anion charge n=2 (i.e. as for $CO_3^{2-}$ or $SO_4^{2-}$) would result in a predicted value for ($C_{calc}$) of 0.17. The experimental value for $C_{exp}$ can be determined from the sum of the amount (mole equivalent) of sulphate and carbonate anion. The $\Delta$ is defined as the difference between the C calculated and C experimental wherein a lower $\Delta$ value indicates a more pure hydrotalcite phase. The smallest $\Delta$ value is observed when precipitating above pH 9.5.

The data of Table 3 (shown in FIG. 1) and the description of examples 8-24 in the example section shows that the best overall quality (i.e. good phosphate binding, high filtration rates, low wash times, a molar ratio of approximately 2 0, no non-hydrotalcite crystalline phases and a small $\Delta$) are obtained for those samples wherein the interlayer sulphate levels are between 2 and 5 wt %, and preferably a sulphate to carbonate molar ratio of between 0.14 to 0.26. The total amount of anion (sulphate and carbonate) is preferably from 0.15 to 0.20 more preferably is of 0.19 mole equivalent.

In order to control interlayer sulphate below 3%, the $Na_2CO_3$ had to be of more than 2 mole excess. To maintain the interlayer sulphate above 2 wt % the precipitation pH has to be less than 10 and of 2.7 moles excess $Na_2CO_3$ or less.

Sodium carbonate not only provides the carbonate for the anion-exchange sites, but also acts as a pH buffer which assists pH control during precipitation. The ability to maintain an accurate precipitation pH is considerably increased when $Na_2CO_3$ is present and for that reason an excess of $Na_2CO_3$ of more than 2 is preferred. However, we found that an excess $Na_2CO_3$ of 4 or above is less preferred because this could result in an increased risk of incomplete dissolution of $Na_2CO_3$ in the reactant solution at the preferred reaction temperatures (of less than 25° C.) when preparing unaged mixed metal compounds.

For example, during dissolution of the sodium hydroxide and sodium carbonate in the feed-solutions, the solution temperature may rise to 65° C. and we found that an excess in $Na_2CO_3$ of 4 or more does dissolve; however, cooling and/or pressurisation was required during dissolution to limit evaporation and to lower the temperature to the same value as that required for the reaction to prevent ageing. When the $Na_2CO_3$ solution (of more than 4 mole excess) is cooled from 65 to 25° C. partial precipitation of the $Na_2CO_3$ occurs.

It was therefore preferred to maintain the $Na_2CO_3$ at 4 mole excess or less. We found that it was possible to lower the excess $Na_2CO_3$ from 4 to 21 mole without affecting pH control.

To summarise, the data of Table 3 suggest that when outside a range of 13 to 5 wt % interlayer sulphate, phosphate binding either decreases and/or the Mg:Fe molar ratio of 2.0 is not maintained and/or separation of the slurry is more difficult to achieve A Mg:Fe molar ratio of 2.0 was targeted such as to obtain the highest phosphate binding per mole of magnesium released. A preferred range of between 1.8 to 5 wt % interlayer sulphate was achieved by selection of pH and $Na_2CO_3$ excess within a narrow range.

(ii) Reaction Slurry PSD and Filter Cake Moisture Content

Particle Size Distribution (PSD)—The particle size distribution is an important material parameter which influences the filtration time of the reaction precipitate slurry. In the laboratory with similar reactant concentration, reactant addition rate, reaction temperature and pH and water heel volume, differing agitation configurations produced different PSDs. Thus the PSD of the reaction precipitate is strongly influenced by the agitation regime, the vessel configuration, and the mode of reactant addition. We have identified the agitation conditions at commercial scale to enable optimum filtration and washing conditions whilst ensuring that the final product is essentially unchanged from that at low tonnes per annum scale.

Without being bound by theory it is postulated that high pH/sub-optimal mixing can result in a small particle size which can block up the filter cloth, reduce the filtration rate through the cake and limit the ultimate solids content of the filter cake. We found that there is a significant increase in filtration time when reaction slurry psd (d50) is reduced to less than 70 microns. Investigations (data shown in Table 4) demonstrated that control of particle size above approximately 70 microns is preferable in maintaining a high filtration rate suitable for use of separation methods on a commercial scale such as centrifuge, Neutsch and belt filters. In addition, we found that unwanted crystal growth (ageing) can be minimised if filtration time is kept at a minimum. We also found that a reduction in particle size to less than 70 microns leads to an increase in moisture content of the filter cake to more than 80 wt %. This filter cake is stickier and is therefore more difficult to remove from the filtration equipment and will tend to hold up in mechanical devices or containers during handling. A preferred moisture content of the filter cake is therefore less than 80 wt %. Consequently, separating the mixed metal compound from reaction slurry of more than 90 wt % moisture content is also preferred.

There is therefore a preferred combination of both a filter cake of moisture content (less than 80 wt %) and a PSD (of more than 70 microns) to enable manufacture on a larger scale of compositions free of aluminium.

(iii) Agitation Regime

The results described herein demonstrate that the preferred PSD of reaction slurry are obtainable when maintaining the reaction pH between pH 9.5-11 (preferably at pH 9.5 to 10, more preferably 9.8) In general, the teachings of WO99/15189 would not enable separation of the compound on a commercial scale. Furthermore, we found that the method of agitation (power per unit volume of 0.03 to 1.6 kW/m$^3$) during precipitation is preferred. Slow stirring (i.e. sufficient to maintain the solution homogeneous) was then maintained during the hold time. We found that filtration time increased significantly when the slurry is stirred for a prolonged period during the hold time. For example, we found that a hold time of more than 30 minutes but less than 12 hours is preferred and the slurry during hold time should be agitated gently. The slurry hold time is defined as the time period between when the addition of Solutions A and B ceases (reaction phase ends) and the last aliquot of slurry is added to the filtration equipment. At pilot plant and large commercial scale where centrifuges are used, the slurry hold time is typically up to 12 hours since multiple aliquots of reaction mass are isolated, washed, dewatered and discharged as wet cake.

The specific reaction agitation configuration to maintain low shear conditions whilst at the same time enabling sufficient mixing were also found to be useful in obtaining a preferred psd of more than 70 microns (when measured at the end of hold time). The specific power input has to be controlled such as to avoid a rate which is too low but not at a rate which breaks the particles down into very fine particles of psd less than 70 microns. Evaporation of water from the reaction slurry and ageing of crystallites was prevented by maintaining the reaction temperature below 30 Celsius and typically was not less than 15 Celsius to avoid unacceptable reduction in reactant feed stream solubility.

TABLE 4

Effect of slurry Particle Size Distribution (PSD) on filterability

| Example Number | Precipitation pH | Filtration type | Mg:Fe Mole Ratio Method 1 | PSD reaction slurry d50 (Lasentec) Method 9 microns | Time of psd measurement hrs | Slurry hold time hrs | Filtration Time (Lab scale) Method 8 seconds | Filtration Rate (Lab Scale) Method 10 ml/min |
|---|---|---|---|---|---|---|---|---|
| 25 | 9.6 | Lab Filter | 1.9 | 81 | 2 | 2 | 37 | n/a |
| 26 | 10.1 | Lab Filter | 1.9 | 69 | 4 | 4 | 177 | n/a |
| 27 | 10.3 | Lab Filter | 2.1 | 60 | 4 | 4 | 350 | n/a |
| 28b | 9.8 | Centrifuge | 1.9 | 45 | 0.75 hrs (ie after addition of reactants complete) | 4 | n/a | n/a |
| 28b | 9.8 | Centrifuge | 1.9 | 79 | 4 | 4 | n/a | n/a |
| 29 | 10.3 | Centrifuge | n/a | | | n/a | n/a | n/a |
| 30 | 9.8 | Neutsch | 1.9 | | | 0.5 | n/a | n/a |
| 31 | 10.3 | Neutsch | 2.0 | | | 0.5 | n/a | n/a |
| 32 | 9.8 | Belt | 2.0 | | | 0.5 | n/a | n/a |
| 33 | 9.6 | Tangential flow filtration | 1.9 | 81 | 2 | 2 | n/a | 7 |
| 34 | 10.1 | Tangential flow filtration | 1.9 | 69 | 4 | 4 | n/a | 22 |
| 35 | 10.3 | Tangential flow filtration | 2.1 | 60 | 4 | 4 | n/a | 20 |
| 36 | 9.8 | Wet Milled + Tangential flow filtration | 1.9 | 60 | 28 | 28 | n/a | |
| 37 | 10.3 | Wet Milled + Tangential flow filtration | 2.0 | 47 | 33 | 33 | n/a | |

(iv) Selection of a Preferred Filtration Method and its Operation.

In general, a filtration method is used to isolate the product from slurry form, wash to a predetermined impurity end point and de-water the cake in order to obtain a material of sufficiently high solids content to facilitate handling and for efficient drying. In the case of laboratory filtration equipment de-watering is typically not carried out due to the limitations of the equipment used and due to small quantities handled.

Tangential Flow Filtration (TFF)

A method whereby filtration rate increases when psd is less than 70 microns is the Tangential Flow Filtration (diafiltration) method (Table 4 and 5); however, diafiltration in general has significantly lower filtration rates (at all psd ranges) and is only suitable for filtration of diluted slurries of more than 94 wt % moisture content Reaction slurry could be washed, but not concentrated, since moisture contents below approximately 94 wt %, would lead to blockage of the TFF. The washed slurry would then require much greater energy input during drying. Consequently, separation by diafiltration is less preferred.

Neutsche Filter

Isolation and washing of the drug substance was also carried out using a Neutsche filter at a 7 kg production scale. This equipment gave good product separation and washing but the specific filtration rate (kg product/m² h) was extremely slow and the filter cake contained up to 85 wt % moisture content requiring much increased energy usage during drying. A cake depth of ~7 cm was achieved in the Neutsche filter and 10 cm in a filter/drier, whereas cake depths of 30 cm or more are not uncommon for filter/driers in other applications. Separation, by Neutsch filter we found to be less preferred for manufacture on a commercial scale because of lower filtration rate and limitations in handling larger amounts of the clay-like product.

Belt Filter

A belt filter is preferred as we found that these could be operated with a cake depth range of 15-25 mm at relatively high filtration rates. This filtration method provides high filtration rates when psd is maintained above 70 microns.

Centrifuge

Different filtration methods were tested but best results were obtained with a filtration method using centrifuge which combines filtration followed by washing and de-watering in one step. Centrifugal filtration is preferred and provides advantages of high filtration rate and preferred filter cake moisture content whilst maintaining the quality of the product (Table 4 and 5).

(vi) Morphology

High daily, repeated long-term (chronic) dosages and restricted fluid intake are required for kidney patients. Consequently, a high dosage of drug substance is required in the final product (i.e. tablet) and the manufacture and qualities of the final product is therefore sensitive to the form and shape (morphology) properties of the mixed metal compounds drug substance, unlike more typical formulations. This means that the properties of the tablet, including key physical properties, and the tablet manufacturing processes, such as granulation, are often primarily influenced by the properties of the mixed metal compound active substance rather than those of the excipients, as is more typically the case. In order to be able to manufacture a pharmaceutical product comprising such significant quantities of mixed metal compound with the control and consistency necessary for pharmaceutical use, a means of controlling an array of these physical properties of the mixed metal compounds is essential.

It is important to dry the material carefully as it is easy to change the surface area or internal pore volume and hence change the therapeutic activity (Table 6).

TABLE 6

Effect of API morphology on granules and tablets properties.

| | Properties API | | | | | Granulation | Tablet | | |
| --- | --- | --- | --- | --- | --- | --- | --- | --- | --- |
| Example Number | Average crystal size Method 2 Angstrom (Å) | Surface Area $N_2$ Method 14 m²/g | Pore volume $N_2$ Method 14 cm³/g | Pore volume Water Method 15 cm³/g | Phosphate binding Method 3 mmol/g API | Change phosphate binding after storage (12 mnths) % | End Point Total water added/kg API in dry mix Method 16 dm³ | Tablet Volume Method 17 mm³ | Phosphate binding Method 3 mmol/g API | Change phosphate binding after storage (12 months) % |
| 38 | 151 | 54 | 0.17 | 0.36 | 0.68 | −3 | 0.57 | 470 | 0.67 | −2 |
| 39 | 160 | 57 | 0.20 | 0.44 | 0.63 | −5 | 0.60 | 477 | 0.63 | −5 |
| 40 | 102 | 77 | 0.26 | 0.86 | 0.69 | | 0.95 | 532 | 0.68 | −2 |
| 41 | 97 | 74 | 0.31 | 1.10 | 0.68 | | N/A | N/A | N/A | N/A |
| 66 | 77 | 119 | 0.30 | 0.68 | 0.79 | −12.5 | | | | |

TABLE 5

Selection of filtration methods

| Example Number | Filtration Method | Moisture Content of Wet Cake Method 12 % | Preferred Precipitation pH Range | Preferred Slurry PSD d50 at end of hold time Method 9 microns |
| --- | --- | --- | --- | --- |
| 28b | Centrifuge | 76-78 | 9.5-10 | >70 |
| 34 or 35 | Tangential Flow Filtration | 92-95 | 10-10.5 | <70 |
| 25 | Lab Filter | 85 | 9.5-10 | >70 |
| 30 | Neutsch | 85 | 9.5-10 | >70 |
| 32 | Belt Filter dryer | 75-85 85 | 9.5-10 | >70 >70 |

Drying

We found that too much processing and handling; for example, such as overdrying can present changes (such as growth of crystallite size) that are unacceptable in the final mixed metal Mg:Fe compound. How the API morphology (vi) affects storage stability and downstream processing is shown in Table 6. How to control drying to achieve the required porosity (vii) and crystallite size (viii) is described in more detail in Table 7 and 8.

Table 6 shows how pore volume and surface area affects the control of phosphate binding capacity, storage stability, the granulation process and the production of tablets. As a general rule, hydrotalcite type materials of a higher surface area may be expected to have a higher ion exchange capacity and thereby higher phosphate binding; this can be seen from Example 66 which has a high surface area of 119 m²/g and also a high phosphate binding value. However, the material with the higher surface area of 119 m²/g was found to be less stable upon storage because phosphate binding activity decreased by 12%. We have found that a lower surface area range of between 40 and 80 m²/g is more preferred as it has the advantage of maintaining good phosphate binding (more than 0.6 mmol/g API) that is importantly also essentially unchanged (only 5% or less change) upon storage over periods of up to years, making it more viable as a an active pharmaceutical material. It may be expected typically that significantly higher surface areas would be required to attain such stable phosphate binding such materials of lower surface areas (by $N_2$) of between 40-80 m²/g and have a pore volume (by $N_2$) of 0.10-0.28 cm³/g and/or a pore volume (by water) of 0.3-0.6 cm³/g may be expected to have greater sensitivity to any changes in the internal structure resulting in the inhibition of access of the phosphate ions into the material and consequential reduction in phosphate binding capacity Surprisingly, the data presented in Table 6 shows that all these examples of mixed metal compound of lower surface areas are storage stable and maintain good phosphate binding. Furthermore, the materials of lower surface areas, in the range of between 40-70 m$^2$/g and low pore volume (water) of 0.3-0.6 cm$^3$/g offers the advantage of a denser material that can then be processed into a dosage form that is smaller (i.e. as can be seen from Table 6 tablet volume of less than 500 mm$^3$) thereby improving tablet pill burden; a prevalent issue within the treatment of renal patients. Furthermore an additional surprising benefit is that such materials also exhibit no significant reduction in the uptake rate of phosphate, despite the lower surface areas. This facet can be important when considering such materials for pharmaceutical applications in which the binding of phosphate needs to be rapid, such as renal care. We have also found that the material of crystallite size less 200 Å binds greater than 80% of phosphate within 10 minutes (according to Test method 3 but measured at different time intervals) when maintained at a average particle size less than 100 μm, preferably less than 50 μm, most preferred less than 10 μm and a surface area more than 40 m$^2$/g.

by exposing the crude product to a product temperature of more than 80 but no greater than 150° C. and provide a rate of drying (water evaporation rate) of between 0.05 to 0.5 kg water per hour per kg of dry product and/or provide a dryer residence time of between 10 minutes to 30 hours and/or a product rate per unit area of between 0-7 kg product/(m$^2$·hr) typically achieved by use of a high residence time dryer under a vacuum of pressure of 400 mbar (absolute) or less. A product of low pore volume (by water) range of 0.3-0.6 cm$^3$/g can be obtained by a combination of the centrifuge and use of agitated spherical dryer method.

Alternatively, a product of crystallite size less than 140 Å and a surface area (by N$_2$) of between 80-150 m$^2$/g, and/or pore volume (by N$_2$) of between 0.28-1.0 cm$^3$/g, and/or pore volume (by water) of between 0.6-1.2 cm$^3$/g can be achieved by exposing the crude product to a product temperature of more than 35° C. but no greater than 150° C. and provide a rate of drying (water evaporation rate) of between 500 to 50000 kg water per hour per kg of dry product and/or provide a dryer residence time of less than 10 minutes and/or a delta T of between 0.2 to 1.0 typically achieved by use of a short residence time dryer

TABLE 7

Effect of rate of drying on morphology

| Example Number | Rate of Drying Method 18 kg water/ (kg dried product · hr) | Dryer Residence Time Method 19 hours | Product rate per unit area Method 20 kg product/ (m$^2$ · hr) | delta T Method 21 (Tin − Tout)/Tin | Moisture Content Dried Product Method 12 wt % | Surface Area N$_2$ Method 14 m$^2$/g | Pore Volume N$_2$ Method 14 cm$^3$/g | Pore Volume Water Method 15 cm$^3$/g | Tap Bulk Density Method 22 g/cm3 | Flow-ability Carr Index Method 23 |
|---|---|---|---|---|---|---|---|---|---|---|
| 42 | 0.09 | 29 | 2.1 | n/a | 19 | | | 0.50 | 0.50 | |
| 43 | 0.13 | 22 | 1.0 | n/a | 10 | 56 | 0.15 | 0.40 | 0.60 | |
| 44 | 0.23 | 16 | 1.3 | n/a | | 61 | 0.19 | 0.50 | 0.54 | |
| 45 | 0.24 | 12 | 1.3 | n/a | | 54 | 0.19 | 0.52 | 0.47 | |
| 28 | 0.26 | 12 | 1.6 | n/a | | 57 | 0.17 | 0.49 | 0.51 | 32 |
| 46 | 0.28 | 11 | 2.1 | n/a | | 54 | 0.18 | 0.48 | 0.56 | |
| 47 | 0.31 | 9.9 | 2.0 | n/a | | 61 | 0.17 | 0.52 | 0.52 | |
| 31 | | 15 | 0.2 | n/a | 8 | 71 | 0.28 | | | 30 |
| 40 | 0.21 | 18 | 0.2 | n/a | | 77 | 0.26 | 1.10 | 0.36 | |
| 48 | 38000 | 0.0001 | n/a | 0.40 | 4 | 81 | 0.28 | 0.64 | 0.43 | 19 |
| 49 | 38000 | 0.0001 | n/a | 0.66 | 3 | 92 | 0.39 | 0.72 | 0.33 | 13 |
| 50 | 990 | 0.02 | n/a | 0.69 | 7 | 93 | 0.41 | 0.76 | 0.48 | ND |
| 51 | 990 | 0.02 | n/a | 0.74 | 15 | 97 | 0.47 | 0.72 | 0.55 | ND |
| 52 | 990 | 0.02 | n/a | 0.76 | 7 | 119 | 0.56 | 0.74 | 0.50 | 22 |
| 66 | 38000 | 0.0001 | n/a | | | 119 | | 0.68 | | |
| 38 | 0.27 | 12.9 | 1.4 | n/a | 7 | 53 | 0.15 | | | |
| 39 | 0.38 | 8.9 | 1.2 | n/a | 5 | 60 | 0.21 | | | |
| 60 | 0.33 | 9.8 | 1.6 | n/a | | 56 | 0.17 | | | |
| 61 | 0.28 | 10.3 | 1.5 | n/a | | 50 | 0.13 | | | |
| 41 | 0.27 | 15.5 | 0.2 | n/a | 5 | | | | | |

(vii) Manufacture of Unaged, Porous Mixed Metal Compounds (Drying)

We have found that the surface area of the drug substance is determined by a combination of rate of drying, residence time, product rate per unit area and delta T (Table 7). The rate of drying is affected by both the mode of drying and other process parameters, such as the product temperature, heating surface/gas temperature.

A product of crystallite size between 90 and 200 Å and a surface area (by N$_2$) of between 40-80 m$^2$/g, and/or pore volume (by N$_2$) of between 0.10-028 cm$^3$/g, and/or pore volume (by water) of between 0.3-0.6 cm$^3$/g can be achieved (viii) Effect of Rate of Drying on Crystallite Size Table 8 shows that the drying must be sufficiently rapid so as minimise crystal growth, however bulk product temperatures exceeding 150° C. must be avoided in order to prevent damage to the characteristic material structure. Factors such as agitation during drying in long residence time dryers were also found to effect crystallite size. For example, dried samples (such as obtained by Neutsche/Tray Oven) whereby no continuous agitation is applied tend to show smaller crystallite size than those obtained by a spherical drier. Therefore an optimum drying regime exists.

TABLE 8

Effect of drying conditions on control of crystallite size

| Example Number | Slurry Treatment | Separation Method | Dryer Method | Rate of Drying Method 18 kg water/ (kg dried product · hr) | Dryer Residence Time Method 19 hours | delta T Method 21 $(T_{in} - T_{out})/T_{in}$ | Product temperature in the dryer Max temperature achieved ° c. | Average crystal size Method 2 Angstrom (Å) | Phosphate Binding Method 3 mmol/g API |
|---|---|---|---|---|---|---|---|---|---|
| 7 | aged | Buchner | Tray Oven (lab) | | | n/a | | 258 | 0.45 |
| 42 | unaged | Centrifuge | Agitated - Spherical | 0.09 | 29 | n/a | 90 | 195 | 0.63 |
| 44 | unaged | Centrifuge | Agitated - Spherical | 0.23 | 16 | n/a | 83 | 175 | 0.63 |
| 45 | unaged | Centrifuge | Agitated - Spherical | 0.24 | 12 | n/a | 74 | 160 | 0.67 |
| 38 | unaged | Centrifuge | Agitated - Spherical | 0.27 | 12.9 | n/a | 85 | 160 | |
| 39 | unaged | Centrifuge | Agitated - Spherical | 0.38 | 8.9 | n/a | 73 | 160 | |
| 43 | unaged | Centrifuge | Agitated - Spherical | 0.13 | 22 | n/a | 75 | 157 | 0.66 |
| 60 | unaged | Centrifuge | Agitated - Spherical | 0.33 | 9.8 | n/a | 76 | 154 | 0.69 |
| 28 | unaged | Centrifuge | Agitated - Spherical | 0.26 | 12 | n/a | 72 | 151 | 0.67 |
| 49 | Unaged | Centrifuge | Spin Flash | 38000 | 0.0001 | 0.66 | | 135 | 0.64 |
| 46 | unaged | Centrifuge | Agitated - Spherical | 0.28 | 11 | n/a | 73 | 133 | 0.69 |
| 47 | unaged | Centrifuge | Agitated - Spherical | 0.31 | 9.9 | n/a | 65 | 123 | 0.69 |
| 51 | unaged | Centrifuge | Spray Dryer | 990 | 0.02 | 0.74 | | 123 | 0.68 |
| 52 | unaged | Centrifuge | Spray Dryer | 990 | 0.02 | 0.76 | | 117 | 0.70 |
| 61 | unaged | Centrifuge | Agitated - Spherical | 0.28 | 10.3 | n/a | 64 | 109 | 0.73 |
| 40 | Unaged | Neutsch | Tray Oven | 0.21 | 18 | n/a | | 102 | 0.69 |
| 50 | unaged | TFF | Spray Dryer | 990 | 0.02 | 0.69 | | 100 | 0.75 |
| 41 | unaged | Neutsch | Tray Oven | 0.27 | 15.5 | n/a | | 97 | |
| 31 | unaged | Neutsch | Tray Oven | | 15 | n/a | | 94 | 0.66 |
| 48 | unaged | Centrifuge | Spin Flash | 38000 | 0.0001 | 0.40 | | 93 | 0.68 |
| 66 | unaged | TFF | Spin Flash | 38000 | 0.0001 | 0.48 | | 77 | 0.79 |
| 2 | unaged | Buchner | Tray Oven (lab) | n/a | n/a | n/a | | 69 | 0.73 |

For those compounds wherein the average crystal size of the mixed metal compound is from 10 to 20 nm (100 to 200 Å) preferably from 12 to 20 nm, the surface area (by $N_2$) is between 40-80 $m^2/g$, pore volume (by $N_2$) is between 0.10-0.28 $cm^3/g$ and the pore volume (water) is from 0.3-0.6 $cm^3/g$. The compounds of average crystal size between 100 to 200 Å are preferably obtained by use of a long residence agitated drying process such as an agitated spherical dryer wherein the rate of drying is between 0.09 to 0.31 kg water/(kg dried product·hr), more preferably a rate of drying between 0.24 to 0.31 kg water/(kg dried product·hr) and/or a Product rate per unit area (kg product/$m^2$·hr) of between 1-10 more preferably between 2-7.

We have found, surprisingly that the advantages of the lower surface area product of crystallite size between 100 and 200 Å and/or low surface area 40-80 $m^2/g$ and/or low pore volume (water) 0.3-0.6 $cm^3/g$ prepared by a long residence drying process are good phosphate binding, storage stability and a denser material that can be processed into a dosage form that is smaller thereby improving tablet pill burden. Average crystal size of less than 200 Å has the advantage of good, controlled phosphate binding. A average crystal size of between 120-200 Å is preferred if product is dried to a moisture content less than 15 wt % (preferably between 5-10 wt %) of a batch size of between 50 and 1000 kg when dried by a process of long residence drying with a agitated spherical dryer and when preparing materials of a low surface area of between 40 and 80 $m^2$ per gram and/or pore volume (water) of 0.3-0.6 $cm^3/g$. The low porosity product is preferably prepared from batch sizes between 50 and 1000 kg with a dryer residence time of between 3-30 hours, more preferably between 5 to 30 hours and most preferred between 9 to 30 hours.

Milling

Optionally, after the drying step the dry material may be first classified to remove oversize particles by milling and/or sieving (ix) Effects of PSD on Phosphate Binding and Magnesium Release We have found that Mg release remains constant whereas phosphate binding changes as a function of particle size (Table 9). This is a surprising result as a smaller particle size distribution could be expected to have a larger surface area and therefore more susceptible to Mg release. However, the magnesium release does not appear to be significantly affected by changes in surface area when maintained at less than 80 $m^2/g$ despite being milled to a particle size distribution (psd) with a (d50) of less than 60 micron when using this route. The constant Mg release enables a wider selection of a preferred pad range to improve phosphate binding without compromising Mg release. The data from Table 9 shows that a preferred particle size d50 is less than 177 micron, more preferably less than 114, most preferred less than 60 micron

TABLE 9

Effect of particle size distribution of dried product
on phosphate binding and magnesium release
(x) Effect of crystallite size on milling rate.

| Example Number | PSD Method 24 d50 (microns) | Phosphate Binding Method 3 mmol/g API | Mg Release Method 3 mmol/g API |
|---|---|---|---|
| 53 | 487 | 0.39 | 0.17 |
| 54 | 315 | 0.52 | 0.18 |
| 55 | 177 | 0.63 | 0.17 |
| 56 | 114 | 0.64 | 0.17 |
| 57 | 60 | 0.67 | 0.19 |
| 58 | 9 | 0.68 | 0.19 |
| 59 | 4 | 0.67 | 0.18 |

If processed incorrectly mixed metal compounds can become unacceptably hard. This can lead to consequent issues of decreased milling rates and higher energy input to achieve a preferred particle size. The consequence of this is that in achieving a given particle size it is essential that the crystallite size is not too low.

Table 10 shows that if the crystallite size is too low (i.e. of 120 Å or less) the milling rate will be reduced by more than 50% when compared to that of crystallite size of 195 Å which will present difficulties at scale when milling to a particle size distribution with a d50 of less than 114 micron. For example, problems with occurrence of non-hydrotalcite phases such as MgO periclase, reduced milling rate or decomposition of the product because of over-heating of the product can occur. For those mixed metal compounds wherein the crystallite size is less than 120 Å it is preferred to use the short residence drying route which does not require milling

TABLE 10

Effect of crystallite size on milling rate and phosphate binding

| Example Number | Crystallite Size Method 2 Angstroms | Milling Rate Quantity of feed processed in a given time g/30 s | Phosphate Binding Method 3 mmol/g API | Mg Release Method 3 mmol/g API |
|---|---|---|---|---|
| 42 | 195 | 650 | 0.63 | 0.18 |
| 44 | 175 | 450 | 0.63 | 0.17 |
| 45 | 160 | 430 | 0.67 | 0.15 |
| 60 | 154 | 370 | 0.69 | 0.15 |
| 47 | 123 | 300 | 0.69 | 0.15 |
| 61 | 110 | 280 | 0.73 | 0.14 |

If the reaction pH rises above pH 11 (and to a certain extent above pH 10) we have found that the resultant mixed metal compounds is a much harder material. It is therefore possible to prepare a softer material by precipitation at pH 9.8 than at higher pH values. Consequently, not only does precipitating at a pH of 9.8 provide the advantage of increased filterability we have also shown this to be of benefit for achieving increased milling rates.

Control of material hardness is also important because this may also increase the potential for pickup of low levels of trace-metals from the milling equipment. When the material is harder it also has to be milled harder which in turn can lead to higher temperatures being generated during milling which provide a milled material which can contain decomposition products or may be too dry (less than 5 wt % moisture content as determined by LOD) which in turn can lead to problems with handling and the downstream processing.

(xi) Methods of Micronisation

If the moisture content of the unmilled product is above 10 wt % then the product can become too sticky for milling whereas if less than 5 wt % the product after milling will be too dry and would then be less stable upon storage and/or provide problems in processing into tablet formulations. We found that the milling process results in a further 2 wt % loss of moisture resulting in a milled product. We therefore typically target a moisture content of between 7 and 10 wt % for the unmilled material.

The chemical (i.e. molar ratio of Mg:Fe of 2.1) and physical properties (i.e. surface area and particle size) of the mixed metal compounds composition favour equilibration to a 5-8 wt % moisture content and as such may be less stable upon storage (i.e. have a tendency to re-hydrate) if manufactured to a moisture content less than 5 wt %.

We have found that this compound can be manufactured using a process comprising a short residence drying step such that the resultant representative material has both small average crystal size and high surface area but also importantly and surprisingly exhibits high phosphate binding even when the material is not milled further. The requirement for no milling has the advantage of reduced processing steps. A further advantage is that such material can be suitable for tabletting processes without the need for wet granulation due to the advantageous flow properties. Therefore, in one aspect the present invention provides a mixed metal compound wherein the average crystal size of the mixed metal compound is less than 20 nm (200 Å); in this aspect preferably the surface area is from 80 to 145 $m^2$ per gram. The data from Table 11 shows that for a mixed metal compound with a surface area from 80 to 145 $m^2$ per gram the preferred particle size d50 is less than 343 micron, more preferably less than 296, even more preferably less than 203, most preferred less than 31 micron,

TABLE 11

| Example Number | Micronised | PSD Method 24 d50 (microns) | Phosphate Binding Method 3 mmol/g API | Mg Release Method 3 mmol/g API | Surface Area $N_2$ Method 14 $m^2/g$ | Micronisation required to achieve good phosphate binding (>0.6 mmol/g) yes/no |
|---|---|---|---|---|---|---|
| 59 | no | 343 | 0.51 | 0.21 | 67 | yes |
| 59 | yes | 4 | 0.67 | 0.18 | 52 | n/a |
| 48 | no | 296 | 0.64 | 0.14 | 81 | no |
| 49 | no | 203 | 0.68 | 0.15 | 92 | no |
| 51 | no | 31 | 0.68 | 0.11 | 97 | no |
| 52 | no | 27 | 0.7 | 0.11 | 119 | no |
| 50 | no | 20 | 0.75 | 0.10 | 93 | no |

The compound of higher surface area of 80-145 m² can be manufactured using a process comprising a short residence drying step such that the resultant representative material has both small average crystal size and high surface area but also importantly and surprisingly exhibits high phosphate binding even when the material is not milled further. The requirement for no milling has the advantage of reduced processing steps and avoids any hardness issues. A further advantage is that such material can be suitable for tabletting processes without the need for wet granulation.

Impurity

Mixed metal compounds may be synthesised by various techniques; however, it is difficult to control impurity levels of compounds when isolated in the unaged form, to a pharmaceutical grade and when prepared Al-free especially when considering that mixed metal compounds are prepared from minerals containing significant levels of trace-metal impurities some of which may be in the form of heavy metals. In particular, compounds prepared from iron minerals are considerably intermeshed with other metal types as these ultimately are derived from minerals that exist in nature. Some of these metals may compete with the magnesium and iron for formation of the mixed metal compound and get locked into the hydrotalcite phase instead of forming more soluble salts which are readily washed out during the washing process. There is therefore a need to control trace metal impurity levels by selecting preferred conditions and recipe during the precipitation stage; this in order to meet regulatory guidelines whilst obtained via a manufacturing process that can deliver this at scale.

Other impurities, such as sodium and sulphate must be controlled in order that the drug substance is of acceptable quality for human consumption. The sodium concentration is controlled through washing of the isolated drug substance cake.

During the filtration and washing step of the manufacturing process, the slurry is formed into a cake (with the removal of excess mother liquor). The resultant cake is then washed with water to remove excess sodium, sulphate and carbonate down to levels acceptable for the final use of the material.

For pharmaceutical use it is important to be able to identify and control the crystal phase of interest. The way the material is processed influences this, when preparing a compound from 2 different metal types it is possible that it may precipitate as a mixture of single metal compounds instead of a mixed metal compound. Mixed metal compounds are manufactured by co-precipitation which can encourage the formation of different crystalline phases in addition to the hydrotalcite phase. There is therefore the need for a Al-free mixed metal compounds which are also free of any other crystalline phases as determined by the absence of XRD diffraction lines except those attributed to the hydrotalcite phase. When prepared according to the process defined for the unaged samples of crystallite size less than 200 Å we have found that the hydrotalcite phase has the following diffraction X-ray diffraction analysis without the presence of any other crystalline phases: dA ('d' spacings) 7.74, 3.86, 2.62, 2.33, 1.97, 1.55, 1.52, 1.44. Five additional peaks at dA 3.20, 1.76, 1.64, 1.48, 1.40 are only resolved in more crystalline samples i.e. of crystallite size above 200 Å, typically as a result of ageing.

Trace metal impurities must be controlled in order that the drug substance is of acceptable quality for human consumption. We found surprisingly that trace metal concentrations can be controlled by the reaction pH, reaction hold time (ageing) and not only as would be expected by the selection of raw materials of appropriate quality or washing. For example, Table 12 shows how we have been able to further reduce the aluminium (Al) and lead (Pb) levels by control of pH, control of sodium carbonate excess and control of ageing.

TABLE 12

Effect of recipe, reaction conditions on trace metals content mixed metal compound

| Example Number | Trivalent Metal Source | Slurry Treatment | Precipitation pH | Excess Moles Na2CO3 in Recipe Moles | Al Method 25 ppm | Cr Method 25 ppm | Pb Method 25 ppm | Total Heavy Metals Method 26 ppm | Na₂O Method 1 wt % |
|---|---|---|---|---|---|---|---|---|---|
| 62 | Al source | unaged | 9.8 | 2.7 | 96160 | n/d | n/d | n/d | <0.5 |
| 63 | Fe source (A) | unaged | 10.5 | 4.0 | 52 | 32 | 7 | <15 | <0.5 |
| 64 | Fe source (A) | unaged | 10.5 | 2.7 | 56 | 34 | 3 | <11 | <0.5 |
| 9b | Fe source (A) | unaged | 9.8 | 2.7 | 58 | 34 | <1 | <9 | <0.5 |
| 23 | Fe source (A) | aged | 9.8 | 4.0 | 78 | 33 | <1 | <10 | <0.5 |
| 17 | Fe source (B) | unaged | 9.8 | 2.7 | <30 | 1 | <1 | <8 | <0.5 |
| 28 | Fe source (B) | unaged | 9.8 | 2.7 | <30 | 2 | <1 | <9 | <0.5 |
| 9 | Fe source (B) | aged | 9.8 | 2.7 | 57 | 1 | <1 | <9 | <0.5 |

From Table 12 it is possible to conclude that even when changing from a solution (A) of GPR grade Rectapur to a more pure ferric source (B) such as a solution (40.4 to 42.9 wt % ferric sulphate of water industry standard suitable for human consumption conforms to BS EN 890:2004), the aluminium levels may be decreased further (i.e. to less than 30 ppm) by avoiding excessive ageing (i.e. wherein the crystallite size is >200 Å).

Example 62 was prepared with solid aluminium sulphate of Alfa Aesar 98% CAS 17927-65-0 instead of ferric sulphate. All other raw materials were of the same source.

All samples shown in Table 12 were washed equally as indicated by low (<0.5 wt %) and similar Na₂O levels. The washing process was developed such as to provide the required Na₂O levels.

As discussed herein the aluminium levels of the mixed metal compound are less than 10000 ppm. This level is considered suitable Al exposure for a healthy individual and is typical of pharmaceutical grade compounds (i.e. of 99% purity). In contrast, mixed metal compounds commercially available as antacids in the form of a Mg:Al mole ratio of 3:1, typically contain ten times as much Al (i.e. up to 100000 ppm aluminium) and are therefore not suitable for long term use. Renal patients are prone to aluminium accumulation it is therefore more preferred if the aluminium content is less than 2000 ppm (>99.8% purity) based on a total daily intake of 6 g/day and general regulatory guidance.

We have found that a Al level of 1000 ppm (99.9% purity) is achievable when using a large scale process for manufacture of unaged materials. For renal patients an aluminium content as low as possible is preferred and therefore a aluminium content of less than 1000 ppm is more preferable. Using our process we can typically achieve aluminum levels less than 100 ppm; therefore aluminium levels less than 100 ppm are even more preferred. By careful control of reaction conditions we can achieve aluminium levels less than 30 ppm which is most preferred.

The data of Table 12 also demonstrates that it is possible to maintain lead (Pb) levels below the detection limit of <1 ppm when precipitated at pH 9.8 and using an excess of 2.7 moles $Na_2CO_3$ in the recipe instead of precipitating the mixed metal compound at pH 10.5 and using an excess of 4.0 moles $Na_2CO_3$ even when using a more impure source of ferric sulphate. We also found that the total heavy metal content could be maintained at less than 10 ppm total heavy metals (Test Method 26) when using the preferred recipe of pH 9.8 and an excess of 2.7 moles $Na_2CO_3$.

Chromium (Cr) levels are required to be limited to <25 ppm according to the guideline of metal reagents for medicinal compounds CHMP/CWP/QWP/4446/00 Table 12 demonstrates that we have been able to lower the chromium levels from approximately 35 ppm to below the detection limit (less than 1 ppm).

All publications and patents and patent applications mentioned in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:

1. A mixed metal compound comprising at least $Mg^{2+}$ and at least $Fe^{3+}$,
   wherein
   the molar ratio of $Mg^{2+}$ to $Fe^{3+}$ is 2.5:1 to 1.5:1,
   the mixed metal compound has an aluminium content of less than 10000 ppm,
   the average crystal size of the mixed metal compound is from 10 to 20 nm (100 to 200 Å),
   and the d50 average particle size of the mixed metal compound is less than 300 μm.

2. A mixed metal compound according to claim 1 wherein the d50 average particle size of the mixed metal compound is less than 200 μm.

3. A mixed metal compound comprising at least $Mg^{2+}$ and at least $Fe^{3+}$,
   wherein
   the molar ratio of $Mg^{2+}$ to $Fe^{3+}$ is 2.5:1 to 1.5:1,
   the mixed metal compound has an aluminium content of less than 10000 ppm,
   the average crystal size of the mixed metal compound is from 10 to 20 nm (100 to 200 Å),
   and the water pore volume of the mixed metal compound is from 0.25 to 0.7 cm³/g of mixed metal compound.

4. A mixed metal compound according to claim 3 wherein water pore volume of the mixed metal compound is from 0.3 to 0.65 cm³/g of mixed metal compound.

5. A mixed metal compound according to claim 3 wherein the nitrogen pore volume of the mixed metal compound is from 0.28 to 0.56 cm³/g.

6. A mixed metal compound comprising at least $Mg^{2+}$ and at least $Fe^{3+}$,
   wherein
   the molar ratio of $Mg^{2+}$ to $Fe^{3+}$ is 2.5:1 to 1.5:1,
   the mixed metal compound has an aluminium content of less than 10000 ppm, and
   (a)(i) the average crystal size of the mixed metal compound is from 10 to 20 nm (100 to 200 Å)
   and (a)(ii) the interlayer sulphate content of the compound is from 2 to 5 wt %; or
   (b)(i) the average crystal size of the mixed metal compound is less than 20 nm (200 Å) and (b)(ii) the interlayer sulphate content of the compound is from 2.1 to 5 wt %.

7. A mixed metal compound according to claim 6 wherein the average crystal size of the mixed metal compound is from 12 to 20 nm (120 to 200 Å).

8. A mixed metal compound comprising at least $Mg^{2+}$ and at least $Fe^{3+}$,
   wherein
   the molar ratio of $Mg^{2+}$ to $Fe^{3+}$ is 2.5:1 to 1.5:1,
   the mixed metal compound has an aluminium content of less than 10000 ppm, and
   (a)(i) the average crystal size of the mixed metal compound is less than 20 nm (200 Å) and (a)(ii) the surface area is from 80 to 145 m² per gram of compound
   or
   (b)(i) the average crystal size of the mixed metal compound is from 10 to 20 nm (100 to 200 Å)
   and (b)(ii) the surface area is from 40 to 80 m² per gram of compound.

9. A mixed metal compound according to claim 8 wherein the compound has a d50 average particle size of from 10 to 350 μm.

10. A mixed metal compound according to claim 8 wherein the compound has a d50 average particle size of from 10 to 100 μm.

11. A mixed metal compound according to claim 8 wherein the compound releases magnesium in an amount less than 0.15 mmol magnesium/g compound, when the compound is mixed with 40 mM phosphate buffer solution (pH 4) at 37.5° C. and shook for 30 minutes.

12. A mixed metal compound according to claim 8 wherein the water pore volume of the mixed metal compound is from 0.25 to 0.7 cm³/g of mixed metal compound.

13. A compound according to claim 1 wherein the compound is of the formula

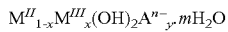

$$M^{II}_{1-x}M^{III}_{x}(OH)_2A^{n-}_{y}.mH_2O$$

wherein $M^{II}$ is one or more bivalent metals and is at least $Mg^{2+}$;
$M^{III}$ is one or more trivalent metals and is at least $Fe^{3+}$;
$A^{n-}$ is one or more n-valent anions and is at least $CO_3^{2-}$;
x/Σyn is from 1 to 1.2
0<x≤0.4,
0<y≤1 and
0<m≤10.

14. A compound according to claim 13 wherein x/Σyn is from 1.05 to 1.15.

15. A compound according to claim 13 wherein x/Σyn is 1.

16. A compound according to claim 1 wherein the compound has an aluminium content of less than 30 ppm.

17. A compound according to claim 1 wherein the interlayer sulphate content of the compound is from 2 to 5 wt %.

18. A compound according to claim 1 wherein the compound has a d50 average particle size of less than 100 μm.

19. A compound according to claim 1 wherein the compound has a d50 average particle size of 5 to 50 μm.

20. A compound according to claim 1 wherein the compound has a d50 average particle size of approximately 5 μm.

21. A compound according to claim 1 wherein the water pore volume of the mixed metal compound is from 0.25 to 0.7 cm³/g of mixed metal compound.

22. A compound according to claim 1 wherein the compound has a dry solid content of at least 20 wt %.

23. A compound according to claim 3 wherein the compound is of the formula $$M^{II}_{1-x}M^{III}_x(OH)_2A^{n-}_y \cdot mH_2O$$

wherein $M^{II}$ is one or more bivalent metals and is at least $Mg^{2+}$;
$M^{III}$ is one or more trivalent metals and is at least $Fe^{3+}$;
$A^{n-}$ is one or more n-valent anions and is at least $CO_3^{2-}$;
x/Σyn is from 1 to 1.2
0<x≤0.4,
0<y≤1 and
0<m≤10.

24. A compound according to claim 6 wherein the compound is of the formula $$M^{II}_{1-x}M^{III}_x(OH)_2A^{n-}_y \cdot mH_2O$$

wherein $M^{II}$ is one or more bivalent metals and is at least $Mg^{2+}$;
$M^{III}$ is one or more trivalent metals and is at least $Fe^{3+}$;
$A^{n-}$ is one or more n-valent anions and is at least $CO_3^{2-}$;
x/Σyn is from 1 to 1.2
0<x≤0.4,
0<y≤1 and
0<m≤10.

25. A compound according to claim 8 wherein the compound is of the formula $$M^{II}_{1-x}M^{III}_x(OH)_2A^{n-}_y \cdot mH_2O$$

wherein $M^{II}$ is one or more bivalent metals and is at least $Mg^{2+}$;
$M^{III}$ is one or more trivalent metals and is at least $Fe^{3+}$;
$A^{n-}$ is one or more n-valent anions and is at least $CO_3^{2-}$;
x/Σyn is from 1 to 1.2
0<x≤0.4,
0<y≤1 and
0<m≤10.

26. A compound according to claim 3 wherein the compound has a dry solid content of at least 20 wt %.

27. A compound according to claim 6 wherein the compound has a dry solid content of at least 20 wt %.

28. A compound according to claim 8 wherein the compound has a dry solid content of at least 20 wt %.

29. A compound according to claim 6 wherein the water pore volume of the mixed metal compound is from 0.25 to 0.7 cm³/g of mixed metal compound.

30. A pharmaceutical composition comprising a mixed metal compound as defined in claim 1 and optionally one or more pharmaceutically acceptable adjuvants, excipients, diluents or carriers.

31. A pharmaceutical composition according to claim 30 in the form of a tablet, capsule or granule.

32. A pharmaceutical composition comprising a mixed metal compound as defined in claim 3 and optionally one or more pharmaceutically acceptable adjuvants, excipients, diluents or carriers.

33. A pharmaceutical composition according to claim 32 in the form of a tablet, capsule or granule.

34. A pharmaceutical composition comprising a mixed metal compound as defined in claim 6 and optionally one or more pharmaceutically acceptable adjuvants, excipients, diluents or carriers.

35. A pharmaceutical composition according to claim 34 in the form of a tablet, capsule or granule.

36. A pharmaceutical composition comprising a mixed metal compound as defined in claim 8 and optionally one or more pharmaceutically acceptable adjuvants, excipients, diluents or carriers.

37. A pharmaceutical composition according to claim 36 in the form of a tablet, capsule or granule.

* * * * *